United States Patent
Heartlein et al.

(10) Patent No.: US 11,254,936 B2
(45) Date of Patent: Feb. 22, 2022

(54) NUCLEASE RESISTANT POLYNUCLEOTIDES AND USES THEREOF

(71) Applicant: Translate Bio, Inc., Lexington, MA (US)

(72) Inventors: Michael Heartlein, Boxborough, MA (US); Braydon Charles Guild, Concord, MA (US); Frank DeRosa, Chelmsford, MA (US)

(73) Assignee: Translate Bio, Inc., Lexington, MA (US)

( * ) Notice: Subject to any disclaimer, the term of this patent is extended or adjusted under 35 U.S.C. 154(b) by 0 days.

(21) Appl. No.: 15/983,635

(22) Filed: May 18, 2018

(65) Prior Publication Data

US 2019/0100753 A1  Apr. 4, 2019

Related U.S. Application Data

(63) Continuation of application No. 14/406,424, filed as application No. PCT/US2013/044769 on Jun. 7, 2013, now abandoned.

(60) Provisional application No. 61/657,465, filed on Jun. 8, 2012.

(51) Int. Cl.
| | | |
|---|---|---|
| C12N 15/11 | (2006.01) | |
| C07H 21/02 | (2006.01) | |
| C07H 21/00 | (2006.01) | |
| C07K 14/505 | (2006.01) | |
| C12P 21/02 | (2006.01) | |

(52) U.S. Cl.
CPC ............ *C12N 15/111* (2013.01); *C07H 21/00* (2013.01); *C07H 21/02* (2013.01); *C07K 14/505* (2013.01); *C12N 2310/3519* (2013.01); *C12N 2320/51* (2013.01); *C12P 21/02* (2013.01)

(58) Field of Classification Search
CPC .......................... C12Q 1/6804; C12N 2320/51
See application file for complete search history.

(56) References Cited

U.S. PATENT DOCUMENTS

| | | |
|---|---|---|
| 2,647,121 A | 7/1953 | Jacoby |
| 2,717,909 A | 9/1955 | Kosmin |
| 2,844,629 A | 7/1958 | William et al. |
| 3,096,560 A | 7/1963 | Liebig |
| 3,535,289 A | 10/1970 | Yoshihara et al. |
| 3,614,954 A | 10/1971 | Mirowski et al. |
| 3,614,955 A | 10/1971 | Mirowski |
| 3,656,185 A | 4/1972 | Carpentier |
| 3,805,301 A | 4/1974 | Liebig |
| 3,945,052 A | 3/1976 | Liebig |
| 3,995,623 A | 12/1976 | Blake et al. |
| 4,013,507 A | 3/1977 | Rembaum |
| 4,072,146 A | 2/1978 | Howes |
| 4,096,860 A | 6/1978 | McLaughlin |
| 4,099,528 A | 7/1978 | Sorenson et al. |
| 4,106,129 A | 8/1978 | Carpentier et al. |
| 4,134,402 A | 1/1979 | Mahurkar |
| 4,140,126 A | 2/1979 | Choudhury |
| 4,180,068 A | 12/1979 | Jacobsen et al. |
| 4,182,833 A | 1/1980 | Hicks |
| 4,227,533 A | 10/1980 | Godfrey |
| 4,284,459 A | 8/1981 | Patel et al. |
| 4,308,085 A | 12/1981 | Horhold et al. |
| 4,323,525 A | 4/1982 | Bornat |
| 4,335,723 A | 6/1982 | Patel |
| 4,339,369 A | 7/1982 | Hicks et al. |
| 4,355,426 A | 10/1982 | MacGregor |
| 4,375,817 A | 3/1983 | Engle et al. |
| 4,385,631 A | 5/1983 | Uthmann |
| 4,401,472 A | 8/1983 | Gerber |
| 4,406,656 A | 9/1983 | Hattler et al. |
| 4,475,972 A | 10/1984 | Wong |
| 4,530,113 A | 7/1985 | Matterson |
| 4,550,447 A | 11/1985 | Seiler, Jr. et al. |
| 4,562,596 A | 1/1986 | Kornberg |
| 4,568,329 A | 2/1986 | Mahurkar |
| 4,571,241 A | 2/1986 | Christopher |
| 4,601,718 A | 7/1986 | Possis et al. |
| 4,647,416 A | 3/1987 | Seiler, Jr. et al. |
| 4,662,382 A | 5/1987 | Sluetz et al. |
| 4,701,162 A | 10/1987 | Rosenberg |
| 4,710,169 A | 12/1987 | Christopher |
| 4,720,517 A | 1/1988 | Ravichandran et al. |

(Continued)

FOREIGN PATENT DOCUMENTS

| | | |
|---|---|---|
| CA | 2518132 A1 | 3/2006 |
| CA | 2807552 A1 | 2/2012 |

(Continued)

OTHER PUBLICATIONS

Dunbar et al., Gene Therapy comes of age. Science 359 (eaan4672) : 10 pages (Year: 2018).*
Herzog et al. PNAS 94:5804-5809 (Year: 1997).*
Li and Huang.Millennium Review :Nonviral gene therapy: promises and challenges. Gene Therapy 7:31-34 (Year: 2000).*
Mingozzi et al.,Review Article : Immune responses to AAV vectors: overcoming barriers to successful gene therapy. Blood 122(1) :23 (Year: 2013).*

(Continued)

*Primary Examiner* — Ethan C Whisenant
(74) *Attorney, Agent, or Firm* — Proskauer Rose LLP; Fangli Chen; Nicholas C. Prairie

(57) ABSTRACT

The invention provides, among other things, methods of stabilizing mRNA and nuclease resistant mRNA prepared in accordance with such methods. In certain embodiments, the nuclease resistant mRNA encodes a functional protein, such as enzyme, and is characterized by its resistance to nuclease digestion, increased half-life and/or its ability to produce increased amounts of the functional protein (e.g., enzyme) encoded thereby.

11 Claims, 4 Drawing Sheets
Specification includes a Sequence Listing.

(56) References Cited

U.S. PATENT DOCUMENTS

| | | |
|---|---|---|
| 4,737,323 A | 4/1988 | Martin et al. |
| 4,762,915 A | 8/1988 | Kung et al. |
| 4,782,836 A | 11/1988 | Alt |
| 4,856,521 A | 8/1989 | Irnich |
| 4,860,751 A | 8/1989 | Callaghan |
| 4,878,908 A | 11/1989 | Martin et al. |
| 4,892,540 A | 1/1990 | Vallana |
| 4,897,355 A | 1/1990 | Eppstein et al. |
| 4,920,016 A | 4/1990 | Allen et al. |
| 4,946,683 A | 8/1990 | Forssen |
| 4,946,857 A | 8/1990 | Kanehira et al. |
| 4,960,409 A | 10/1990 | Catalano |
| 4,966,945 A | 10/1990 | Drawert et al. |
| 5,024,671 A | 6/1991 | Tu et al. |
| 5,025,005 A | 6/1991 | Nomura et al. |
| 5,047,540 A | 9/1991 | Kamata et al. |
| 5,101,824 A | 4/1992 | Lekholm |
| 5,104,399 A | 4/1992 | Lazarus |
| 5,116,360 A | 5/1992 | Pinchuk et al. |
| 5,138,067 A | 8/1992 | Kamata et al. |
| 5,151,105 A | 9/1992 | Kwan-Gett |
| 5,171,678 A | 12/1992 | Behr et al. |
| 5,176,661 A | 1/1993 | Evard et al. |
| 5,194,654 A | 3/1993 | Hostetler et al. |
| 5,200,395 A | 4/1993 | Eto et al. |
| 5,223,263 A | 6/1993 | Hostetler et al. |
| 5,261,419 A | 11/1993 | Osypka |
| 5,264,618 A | 11/1993 | Felgner et al. |
| 5,279,833 A | 1/1994 | Rose |
| 5,282,824 A | 2/1994 | Gianturco |
| 5,284,491 A | 2/1994 | Sutton et al. |
| 5,300,022 A | 4/1994 | Klapper et al. |
| 5,314,430 A | 5/1994 | Bardy |
| 5,330,768 A | 7/1994 | Park et al. |
| 5,334,761 A | 8/1994 | Gebeyehu et al. |
| 5,395,619 A | 3/1995 | Zalipsky et al. |
| 5,405,363 A | 4/1995 | Kroll et al. |
| 5,405,379 A | 4/1995 | Lane |
| 5,455,352 A | 10/1995 | Huellmann et al. |
| 5,464,924 A | 11/1995 | Silvis et al. |
| 5,503,852 A | 4/1996 | Steiner et al. |
| 5,528,023 A | 6/1996 | Butturini et al. |
| 5,552,155 A | 9/1996 | Bailey et al. |
| 5,595,756 A | 1/1997 | Bally et al. |
| 5,607,385 A | 3/1997 | Francischelli et al. |
| 5,609,624 A | 3/1997 | Kalis |
| 5,610,283 A | 3/1997 | Buechler |
| 5,614,548 A | 3/1997 | Piantadosi et al. |
| 5,626,869 A | 5/1997 | Nyqvist et al. |
| 5,631,018 A | 5/1997 | Zalipsky et al. |
| 5,677,124 A | 10/1997 | DuBois et al. |
| 5,693,088 A | 12/1997 | Lazarus |
| 5,697,953 A | 12/1997 | Kroll et al. |
| 5,700,437 A | 12/1997 | Fujii et al. |
| 5,705,188 A | 1/1998 | Junichi et al. |
| 5,705,385 A | 1/1998 | Bally et al. |
| 5,736,573 A | 4/1998 | Galat |
| 5,744,335 A | 4/1998 | Wolff et al. |
| 5,772,694 A | 6/1998 | Bokros et al. |
| 5,776,165 A | 7/1998 | Ripart |
| 5,776,747 A | 7/1998 | Schinstine et al. |
| 5,783,383 A | 7/1998 | Kondo et al. |
| 5,844,107 A | 12/1998 | Hanson et al. |
| 5,874,105 A | 2/1999 | Watkins et al. |
| 5,885,613 A | 3/1999 | Holland et al. |
| 5,910,168 A | 6/1999 | Myers et al. |
| 5,916,208 A | 6/1999 | Luther et al. |
| 5,965,434 A | 10/1999 | Wolff et al. |
| 5,976,567 A | 11/1999 | Wheeler et al. |
| 5,976,569 A | 11/1999 | Milstein |
| 5,981,501 A | 11/1999 | Wheeler et al. |
| 6,055,454 A | 4/2000 | Heemels |
| 6,067,471 A | 5/2000 | Warren |
| 6,090,384 A | 7/2000 | Ra et al. |
| 6,096,070 A | 8/2000 | Ragheb et al. |
| 6,096,075 A | 8/2000 | Bokros et al. |
| 6,120,799 A | 9/2000 | McDonald et al. |
| 6,147,055 A | 11/2000 | Hobart et al. |
| 6,152,955 A | 11/2000 | KenKnight et al. |
| 6,165,763 A | 12/2000 | Brown et al. |
| 6,169,923 B1 | 1/2001 | Kroll |
| 6,176,877 B1 | 1/2001 | Buchanan et al. |
| 6,204,297 B1 | 3/2001 | Tracy et al. |
| 6,210,892 B1 | 4/2001 | Bennett et al. |
| 6,214,804 B1 | 4/2001 | Felgner et al. |
| 6,271,208 B1 | 8/2001 | Bischoff |
| 6,271,209 B1 | 8/2001 | Smith et al. |
| 6,287,591 B1 | 9/2001 | Semple et al. |
| 6,299,604 B1 | 10/2001 | Ragheb et al. |
| 6,335,199 B1 | 1/2002 | Bischoff et al. |
| 6,358,278 B1 | 3/2002 | Brendzel et al. |
| 6,370,434 B1 | 4/2002 | Zhang et al. |
| 6,371,983 B1 | 4/2002 | Lane |
| 6,417,326 B1 | 7/2002 | Cullis et al. |
| 6,485,726 B1 | 11/2002 | Blumberg et al. |
| 6,534,484 B1 | 3/2003 | Wheeler et al. |
| 6,585,410 B1 | 7/2003 | Ryan |
| 6,586,410 B1 | 7/2003 | Wheeler et al. |
| 6,670,178 B1 | 12/2003 | Selden et al. |
| 6,696,424 B1 | 2/2004 | Wheeler |
| 6,733,777 B2 | 5/2004 | Erbacher et al. |
| 6,743,823 B1 | 6/2004 | Summar et al. |
| 6,756,055 B2 | 6/2004 | McDonald et al. |
| 6,790,838 B2 | 9/2004 | Alison et al. |
| 6,815,432 B2 | 11/2004 | Wheeler et al. |
| 6,821,530 B2 | 11/2004 | Koob et al. |
| 6,835,395 B1 | 12/2004 | Semple et al. |
| 6,858,224 B2 | 2/2005 | Wheeler et al. |
| 6,858,225 B2 | 2/2005 | Semple et al. |
| 6,887,665 B2 | 5/2005 | Trulson et al. |
| 6,998,115 B2 | 2/2006 | Langer et al. |
| 7,022,214 B2 | 4/2006 | Olech |
| 7,067,697 B2 | 6/2006 | Gao |
| 7,084,303 B2 | 8/2006 | Watanabe et al. |
| 7,341,738 B2 | 3/2008 | Semple et al. |
| 7,422,902 B1 | 9/2008 | Wheeler et al. |
| 7,427,394 B2 | 9/2008 | Anderson et al. |
| 7,507,859 B2 | 3/2009 | Grinstaff et al. |
| 7,556,684 B2 | 7/2009 | Bury et al. |
| 7,803,397 B2 | 9/2010 | Heyes et al. |
| 7,901,708 B2 | 3/2011 | MacLachlan et al. |
| 7,972,435 B2 | 7/2011 | Bury et al. |
| 8,021,686 B2 | 9/2011 | Semple et al. |
| 8,071,082 B2 | 12/2011 | Zugates et al. |
| 8,101,741 B2 | 1/2012 | MacLachlan et al. |
| 8,106,022 B2 | 1/2012 | Manoharan et al. |
| 8,158,601 B2 | 4/2012 | Chen et al. |
| 8,188,263 B2 | 5/2012 | MacLachlan et al. |
| RE43,612 E | 8/2012 | Anderson et al. |
| 8,236,943 B2 | 8/2012 | Lee et al. |
| 8,278,036 B2 | 10/2012 | Kariko et al. |
| 8,287,849 B2 | 10/2012 | Langer et al. |
| 8,329,070 B2 | 12/2012 | MacLachlan et al. |
| 8,450,298 B2 | 5/2013 | Mahon et al. |
| 8,450,467 B2 | 5/2013 | Manoharan et al. |
| 8,513,403 B2 | 8/2013 | MacLachlan et al. |
| 8,557,231 B2 | 10/2013 | Langer et al. |
| 8,562,966 B2 | 10/2013 | Zugates et al. |
| 8,569,256 B2 | 10/2013 | Heyes et al. |
| 8,652,512 B2 | 2/2014 | Schmehl et al. |
| 8,691,966 B2 | 4/2014 | Kariko et al. |
| 8,748,089 B2 | 6/2014 | Kariko et al. |
| 8,802,644 B2 | 8/2014 | Chen et al. |
| 8,808,681 B2 | 8/2014 | Anderson et al. |
| 8,808,982 B2 | 8/2014 | Dahl et al. |
| 8,822,663 B2 | 9/2014 | Schrum et al. |
| 8,828,956 B2 | 9/2014 | Manoharan et al. |
| 8,835,108 B2 | 9/2014 | Kariko et al. |
| 8,846,348 B2 | 9/2014 | Jendrisak et al. |
| 8,853,377 B2 | 10/2014 | Guild et al. |
| 8,859,229 B2 | 10/2014 | Rabinovich et al. |
| 8,883,202 B2 | 11/2014 | Manoharan et al. |
| 8,936,942 B2 | 1/2015 | Heyes et al. |
| 8,969,353 B2 | 3/2015 | Mahon et al. |

(56) References Cited

U.S. PATENT DOCUMENTS

| | | |
|---|---|---|
| 8,999,351 B2 | 4/2015 | Manoharan et al. |
| 8,999,950 B2 | 4/2015 | MacLachlan et al. |
| 9,005,930 B2 | 4/2015 | Jendrisak et al. |
| 9,012,219 B2 | 4/2015 | Kariko et al. |
| 9,012,498 B2 | 4/2015 | Manoharan et al. |
| 9,018,187 B2 | 4/2015 | Heyes et al. |
| 9,040,256 B2 | 5/2015 | Grunenwald et al. |
| 9,051,567 B2 | 6/2015 | Fitzgerald et al. |
| 9,061,021 B2 | 6/2015 | Guild et al. |
| 9,074,208 B2 | 7/2015 | MacLachlan et al. |
| 9,080,211 B2 | 7/2015 | Grunenwald et al. |
| 9,085,801 B2 | 7/2015 | Grunenwald et al. |
| 9,254,311 B2 | 2/2016 | Bancel et al. |
| 9,295,689 B2 | 3/2016 | de Fougerolles et al. |
| 9,301,993 B2 | 4/2016 | Chakraborty et al. |
| 9,303,079 B2 | 4/2016 | Chakraborty et al. |
| 9,334,328 B2 | 5/2016 | Schrum et al. |
| 9,345,780 B2 | 5/2016 | Manoharan et al. |
| 9,352,042 B2 | 5/2016 | Heyes et al. |
| 9,352,048 B2 | 5/2016 | Manoharan et al. |
| 9,464,124 B2 | 10/2016 | Bancel et al. |
| 9,533,047 B2 | 1/2017 | de Fougerolles et al. |
| 9,701,965 B2 | 7/2017 | Schrum et al. |
| 2002/0022721 A1 | 2/2002 | Trulson et al. |
| 2002/0094528 A1 | 7/2002 | Salafsky |
| 2002/0192651 A1 | 12/2002 | Wheeler et al. |
| 2002/0192721 A1 | 12/2002 | Rizzuto et al. |
| 2002/0193622 A1 | 12/2002 | Watanabe et al. |
| 2003/0082154 A1 | 5/2003 | Leamon |
| 2003/0083272 A1 | 5/2003 | Wiederholt et al. |
| 2003/0104044 A1 | 6/2003 | Semple et al. |
| 2003/0215395 A1 | 11/2003 | Yu et al. |
| 2004/0110709 A1 | 6/2004 | Li et al. |
| 2004/0132683 A1 | 7/2004 | Felgner et al. |
| 2004/0224912 A1 | 11/2004 | Dobie et al. |
| 2004/0235982 A1 | 11/2004 | Rabasco et al. |
| 2005/0004058 A1 | 1/2005 | Benoit et al. |
| 2005/0008689 A1 | 1/2005 | Semple et al. |
| 2005/0032730 A1 | 2/2005 | Von Der Mulbe et al. |
| 2005/0054026 A1 | 3/2005 | Atsushi et al. |
| 2005/0059005 A1 | 3/2005 | Tuschl et al. |
| 2005/0059624 A1 | 3/2005 | Hoerr et al. |
| 2005/0065107 A1 | 3/2005 | Hobart et al. |
| 2005/0069590 A1 | 3/2005 | Buehler et al. |
| 2005/0079212 A1 | 4/2005 | Wheeler et al. |
| 2005/0143332 A1 | 6/2005 | Monahan et al. |
| 2005/0148786 A1 | 7/2005 | Ikeda et al. |
| 2005/0158302 A1 | 7/2005 | Faustman et al. |
| 2005/0244961 A1 | 11/2005 | Short et al. |
| 2005/0250723 A1 | 11/2005 | Hoerr et al. |
| 2006/0008910 A1 | 1/2006 | MacLachlan et al. |
| 2006/0059576 A1 | 3/2006 | Pasinetti et al. |
| 2006/0069225 A1 | 3/2006 | Wintermantel et al. |
| 2006/0083780 A1 | 4/2006 | Heyes et al. |
| 2006/0172003 A1 | 8/2006 | Meers et al. |
| 2006/0204566 A1 | 9/2006 | Smyth-Templeton et al. |
| 2006/0216343 A1 | 9/2006 | Panzner et al. |
| 2006/0223939 A1 | 10/2006 | Lange et al. |
| 2006/0228404 A1 | 10/2006 | Anderson et al. |
| 2006/0241071 A1 | 10/2006 | Grinstaff et al. |
| 2007/0142628 A1 | 6/2007 | Ghoshal et al. |
| 2007/0172950 A1 | 7/2007 | Wheeler et al. |
| 2007/0252295 A1 | 11/2007 | Panzner et al. |
| 2007/0275923 A1 | 11/2007 | Chen et al. |
| 2007/0281336 A1 | 12/2007 | Jendrisak et al. |
| 2008/0145338 A1 | 6/2008 | Anderson et al. |
| 2008/0160048 A1 | 7/2008 | Fuller |
| 2008/0242626 A1 | 10/2008 | Zugates et al. |
| 2008/0260706 A1 | 10/2008 | Rabinovich et al. |
| 2009/0023673 A1 | 1/2009 | Manoharan et al. |
| 2009/0093433 A1 | 4/2009 | Woolf et al. |
| 2009/0163705 A1 | 6/2009 | Manoharan et al. |
| 2009/0186805 A1 | 7/2009 | Tabor et al. |
| 2009/0221684 A1 | 9/2009 | Grinstaff et al. |
| 2009/0263407 A1 | 10/2009 | Dande et al. |
| 2009/0270481 A1 | 10/2009 | MacLachlan et al. |
| 2009/0286852 A1 | 11/2009 | Kariko et al. |
| 2009/0326051 A1 | 12/2009 | Corey et al. |
| 2010/0028943 A1 | 2/2010 | Thomas et al. |
| 2010/0035249 A1 | 2/2010 | Hayashizaki et al. |
| 2010/0036084 A1 | 2/2010 | Langer et al. |
| 2010/0041152 A1 | 2/2010 | Wheeler et al. |
| 2010/0120129 A1 | 5/2010 | Amshey et al. |
| 2010/0178699 A1 | 7/2010 | Gao et al. |
| 2010/0189729 A1 | 7/2010 | Hoerr et al. |
| 2010/0267806 A1 | 10/2010 | Bumcrot et al. |
| 2010/0323356 A1 | 12/2010 | Inoue et al. |
| 2010/0331234 A1 | 12/2010 | Mahon et al. |
| 2011/0009466 A1* | 1/2011 | Schier ............... C12N 15/111 |
| | | 514/44 A |
| 2011/0009641 A1 | 1/2011 | Anderson et al. |
| 2011/0038941 A1 | 2/2011 | Lee et al. |
| 2011/0092739 A1 | 4/2011 | Chen et al. |
| 2011/0143397 A1 | 6/2011 | Kariko et al. |
| 2011/0171287 A1* | 7/2011 | Saarma ............... C12N 15/111 |
| | | 424/450 |
| 2011/0200582 A1 | 8/2011 | Baryza et al. |
| 2011/0244026 A1 | 10/2011 | Guild et al. |
| 2011/0256175 A1 | 10/2011 | Hope et al. |
| 2011/0287435 A1 | 11/2011 | Grunenwald et al. |
| 2011/0293703 A1 | 12/2011 | Mahon et al. |
| 2011/0311583 A1 | 12/2011 | Manoharan et al. |
| 2012/0007803 A1 | 1/2012 | Takatsuka |
| 2012/0009222 A1 | 1/2012 | Nguyen et al. |
| 2012/0065252 A1 | 3/2012 | Schrum et al. |
| 2012/0065358 A1 | 3/2012 | Langer et al. |
| 2012/0114831 A1 | 5/2012 | Semple et al. |
| 2012/0128760 A1 | 5/2012 | Manoharan et al. |
| 2012/0129910 A1 | 5/2012 | Thompson et al. |
| 2012/0142756 A1 | 6/2012 | Guild et al. |
| 2012/0195936 A1 | 8/2012 | Rudolph et al. |
| 2012/0237975 A1 | 9/2012 | Schrum et al. |
| 2012/0251560 A1 | 10/2012 | Dahlman et al. |
| 2012/0251618 A1 | 10/2012 | Schrum et al. |
| 2013/0017223 A1 | 1/2013 | Hope et al. |
| 2013/0158021 A1 | 6/2013 | Dong et al. |
| 2013/0195967 A1 | 8/2013 | Guild et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2013/0302401 A1 | 11/2013 | Ma et al. |
| 2014/0010861 A1 | 1/2014 | Bancel et al. |
| 2014/0044772 A1 | 2/2014 | MacLachlan et al. |
| 2014/0094399 A1 | 4/2014 | Langer et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0161830 A1 | 6/2014 | Anderson et al. |
| 2014/0162897 A1 | 6/2014 | Grunenwald et al. |
| 2014/0171485 A1 | 6/2014 | Bancel et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200163 A1 | 7/2014 | Mikkelsen et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221248 A1 | 8/2014 | Jendrisak et al. |
| 2014/0221465 A1 | 8/2014 | Bancel et al. |
| 2014/0227300 A1 | 8/2014 | Chin et al. |
| 2014/0243399 A1 | 8/2014 | Schrum et al. |

(56) References Cited

U.S. PATENT DOCUMENTS

| | | |
|---|---|---|
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0288160 A1 | 9/2014 | Guild et al. |
| 2014/0294937 A1 | 10/2014 | MacLachlan et al. |
| 2014/0294938 A1 | 10/2014 | Guild et al. |
| 2014/0294939 A1 | 10/2014 | Guild et al. |
| 2014/0294940 A1 | 10/2014 | Guild et al. |
| 2014/0329884 A1 | 11/2014 | Dong et al. |
| 2014/0343129 A1 | 11/2014 | de Fougerolles et al. |
| 2014/0363876 A1 | 12/2014 | Jendrisak et al. |
| 2015/0004217 A1 | 1/2015 | Guild et al. |
| 2015/0005372 A1 | 1/2015 | Hoge et al. |
| 2015/0011615 A1 | 1/2015 | Manoharan et al. |
| 2015/0011633 A1 | 1/2015 | Shorr et al. |
| 2015/0017211 A1 | 1/2015 | de Fougerolles et al. |
| 2015/0038556 A1 | 2/2015 | Heartlein et al. |
| 2015/0038558 A1 | 2/2015 | Kariko et al. |
| 2015/0044277 A1 | 2/2015 | Chakraborty et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0110857 A1 | 4/2015 | DeRosa et al. |
| 2015/0110858 A1 | 4/2015 | DeRosa et al. |
| 2015/0110859 A1 | 4/2015 | Heartlein et al. |
| 2015/0111945 A1 | 4/2015 | Geisbert et al. |
| 2015/0119444 A1 | 4/2015 | Manoharan et al. |
| 2015/0119445 A1 | 4/2015 | Manoharan et al. |
| 2015/0157565 A1 | 6/2015 | Heartlein et al. |
| 2015/0166465 A1 | 6/2015 | Chen et al. |
| 2015/0190515 A1 | 7/2015 | Manoharan et al. |
| 2015/0191760 A1 | 7/2015 | Jendrisak et al. |
| 2016/0095924 A1 | 4/2016 | Hope et al. |
| 2016/0114011 A1 | 4/2016 | Bancel et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |
| 2016/0151284 A1 | 6/2016 | Heyes et al. |
| 2016/0158385 A1 | 6/2016 | Bancel et al. |

FOREIGN PATENT DOCUMENTS

| | | |
|---|---|---|
| CN | 1399561 | 2/2003 |
| CN | 100569877 C | 12/2009 |
| CN | 101863544 A | 10/2010 |
| DE | 24 30 998 A1 | 1/1975 |
| DE | 25 20 814 A1 | 11/1976 |
| DE | 37 28 917 A1 | 3/1989 |
| EP | 6 73 637 A1 | 9/1995 |
| EP | 0783297 A1 | 7/1997 |
| EP | 0853123 A1 | 7/1998 |
| EP | 0959092 A1 | 11/1999 |
| EP | 2449106 A1 | 11/1999 |
| EP | 1519714 B1 | 4/2005 |
| EP | 1979364 A2 | 10/2008 |
| EP | 2045251 A1 | 4/2009 |
| EP | 2338478 B1 | 6/2011 |
| EP | 2532649 A1 | 12/2012 |
| EP | 2578685 A2 | 4/2013 |
| EP | 2823809 A1 | 1/2015 |
| FR | 1 378 382 A | 11/1964 |
| FR | 2 235 112 A1 | 1/1975 |
| GB | 1072118 A | 6/1967 |
| GB | 1602085 A | 11/1981 |
| JP | H07-053535 | 2/1955 |
| JP | S48-022365 | 3/1973 |
| JP | S49-127908 A | 12/1974 |
| JP | S51-023537 | 2/1976 |
| JP | 51-125144 | 11/1976 |
| JP | S52-010847 | 1/1977 |
| JP | 63-125144 | 5/1988 |
| JP | 63-154788 | 6/1988 |
| JP | H09-505593 | 6/1997 |
| JP | H10-197978 | 7/1998 |
| JP | 11-005786 A | 1/1999 |
| JP | 11-080142 | 3/1999 |
| JP | 2001-523215 A | 11/2001 |
| JP | 2002-167368 A | 6/2002 |
| JP | 2003-519199 A | 6/2003 |
| JP | 4-108173 B2 | 6/2008 |
| JP | 2008-247749 | 10/2008 |
| JP | 50-24216 B2 | 9/2012 |
| WO | WO-90/11092 A1 | 10/1990 |
| WO | WO-93/18229 A1 | 9/1993 |
| WO | WO-93/18754 A1 | 9/1993 |
| WO | WO-95/11004 A1 | 4/1995 |
| WO | WO-95/14651 A1 | 6/1995 |
| WO | WO-95/27478 A1 | 10/1995 |
| WO | WO-96/18372 A2 | 6/1996 |
| WO | WO-96/26179 A1 | 8/1996 |
| WO | WO-96/37211 A1 | 11/1996 |
| WO | WO-96/40964 A2 | 12/1996 |
| WO | WO-97/46223 A1 | 12/1997 |
| WO | WO-98/10748 A1 | 3/1998 |
| WO | WO-98/16202 A2 | 4/1998 |
| WO | WO-98/51278 A2 | 11/1998 |
| WO | WO-99/14346 A2 | 3/1999 |
| WO | WO-00/03044 A1 | 1/2000 |
| WO | WO-00/062813 A2 | 10/2000 |
| WO | WO-00/64484 A2 | 11/2000 |
| WO | WO-00/69913 A1 | 11/2000 |
| WO | WO-01/05375 A1 | 1/2001 |
| WO | WO-01/07599 A1 | 2/2001 |
| WO | WO-02/22709 A1 | 3/2002 |
| WO | WO-02/31025 A2 | 4/2002 |
| WO | WO-02/34236 A2 | 5/2002 |
| WO | WO-02/42317 A2 | 5/2002 |
| WO | WO-03/040288 A2 | 5/2003 |
| WO | WO-03/070735 A2 | 8/2003 |
| WO | WO-2004/011647 A1 | 2/2004 |
| WO | WO-2004/043588 A2 | 5/2004 |
| WO | WO-2004/048345 A2 | 6/2004 |
| WO | WO-2004/106411 A2 | 12/2004 |
| WO | WO-2005/026372 A1 | 3/2005 |
| WO | WO-2005/028619 A2 | 3/2005 |
| WO | WO-2005/037226 A2 | 4/2005 |
| WO | WO-2005/115481 A2 | 12/2005 |
| WO | WO-2005/121348 A1 | 12/2005 |
| WO | WO-2006/000448 A2 | 1/2006 |
| WO | WO-2006/016097 A2 | 2/2006 |
| WO | WO-2006/082088 A1 | 8/2006 |
| WO | WO-2006/105043 A2 | 10/2006 |
| WO | WO-2006/138380 A2 | 12/2006 |
| WO | WO-2007/024708 A2 | 3/2007 |
| WO | WO-2007/031091 A2 | 3/2007 |
| WO | WO-2007/120863 A2 | 10/2007 |
| WO | WO-2007/126386 A1 | 11/2007 |
| WO | WO-2007/143659 A2 | 12/2007 |
| WO | WO-2008/011561 A2 | 1/2008 |
| WO | WO-2008/042973 A2 | 4/2008 |
| WO | WO-2008/045548 A2 | 4/2008 |
| WO | WO-2008/083949 A2 | 7/2008 |
| WO | WO-2008/113364 A2 | 9/2008 |
| WO | WO-2009/046220 A2 | 4/2009 |
| WO | WO-2009/127060 A1 | 10/2009 |
| WO | WO-2009/127230 A1 | 10/2009 |
| WO | WO-2010/042877 A1 | 4/2010 |
| WO | WO-2010/045512 A2 | 4/2010 |
| WO | WO-2010/053572 A2 | 5/2010 |
| WO | WO-2010/054401 A1 | 5/2010 |
| WO | WO-2010/054405 A1 | 5/2010 |
| WO | WO-2010/056403 A1 | 5/2010 |
| WO | WO-2010/099387 A1 | 9/2010 |
| WO | WO-2010/114789 A1 | 10/2010 |
| WO | WO-2010/119256 A1 | 10/2010 |
| WO | WO-2010/129709 A1 | 11/2010 |
| WO | WO-2010/144740 A1 | 12/2010 |

(56) References Cited

FOREIGN PATENT DOCUMENTS

| | | |
|---|---|---|
| WO | WO-2010/147992 A1 | 12/2010 |
| WO | WO-2010/148013 A2 | 12/2010 |
| WO | WO-2011/012316 A2 | 2/2011 |
| WO | WO-2011/012746 A2 | 2/2011 |
| WO | WO-2011/039144 A1 | 4/2011 |
| WO | WO-2011/068810 A1 | 6/2011 |
| WO | WO-2011/075656 A1 | 6/2011 |
| WO | WO-2011/141705 A1 | 11/2011 |
| WO | WO-2012/019168 A2 | 2/2012 |
| WO | WO-2012/019630 A1 | 2/2012 |
| WO | WO-2012/019780 A1 | 2/2012 |
| WO | WO-2012/027675 A2 | 3/2012 |
| WO | WO-2012/045075 A1 | 4/2012 |
| WO | WO-2012/045082 A2 | 4/2012 |
| WO | WO-2012/075040 A2 | 6/2012 |
| WO | WO-2012/133737 A1 | 10/2012 |
| WO | WO-2012/135025 A2 | 10/2012 |
| WO | WO-2012/135805 A2 | 10/2012 |
| WO | WO-2012/170889 A1 | 12/2012 |
| WO | WO-2012/170930 A1 | 12/2012 |
| WO | WO-2013/039857 A1 | 3/2013 |
| WO | WO-2013/039861 A1 | 3/2013 |
| WO | WO-2013/063468 A1 | 5/2013 |
| WO | WO-2013/101690 A1 | 7/2013 |
| WO | WO-2013/102203 A1 | 7/2013 |
| WO | WO-2013/126803 A1 | 8/2013 |
| WO | WO-2013/149140 A1 | 10/2013 |
| WO | WO-2013/149141 A1 | 10/2013 |
| WO | WO-2013/151663 A1 | 10/2013 |
| WO | WO-2013/151664 A1 | 10/2013 |
| WO | WO-2013/151666 A2 | 10/2013 |
| WO | WO-2013/151667 A1 | 10/2013 |
| WO | WO-2013/151668 A2 | 10/2013 |
| WO | WO-2013/151670 A2 | 10/2013 |
| WO | WO-2013/151671 A1 | 10/2013 |
| WO | WO-2013/151672 A2 | 10/2013 |
| WO | WO-2013/151736 A2 | 10/2013 |
| WO | WO-2013/182683 A1 | 12/2013 |
| WO | WO-2013/185067 A1 | 12/2013 |
| WO | WO-2013/185069 A1 | 12/2013 |
| WO | WO-2014/028487 A1 | 2/2014 |
| WO | WO-2014/089486 A1 | 6/2014 |
| WO | WO-2014/113089 A2 | 7/2014 |
| WO | WO-2014/144039 A1 | 9/2014 |
| WO | WO-2014/144196 A1 | 9/2014 |
| WO | WO-2014/144711 A1 | 9/2014 |
| WO | WO-2014/144767 A1 | 9/2014 |
| WO | WO-2014/152027 A1 | 9/2014 |
| WO | WO-2014/152030 A1 | 9/2014 |
| WO | WO-2014/152031 A1 | 9/2014 |
| WO | WO-2014/152211 A1 | 9/2014 |
| WO | WO-2014/152513 A1 | 9/2014 |
| WO | WO-2014/152540 A1 | 9/2014 |
| WO | WO-2014/152659 A1 | 9/2014 |
| WO | WO-2014/152673 A1 | 9/2014 |
| WO | WO-2014/152774 A1 | 9/2014 |
| WO | WO-2014/152940 A1 | 9/2014 |
| WO | WO-2014/152966 A1 | 9/2014 |
| WO | WO-2014/153052 A2 | 9/2014 |
| WO | WO-2014/158795 A1 | 10/2014 |
| WO | WO-2014/159813 A1 | 10/2014 |
| WO | WO-2014/179562 A1 | 11/2014 |
| WO | WO-2014/210356 A1 | 12/2014 |
| WO | WO-2015/006747 A2 | 1/2015 |
| WO | WO-2015/011633 A1 | 1/2015 |
| WO | WO-2015/048744 A2 | 4/2015 |
| WO | WO-2015/051169 A2 | 4/2015 |
| WO | WO-2015/051173 A2 | 4/2015 |
| WO | WO-2015/058069 A1 | 4/2015 |
| WO | WO-2016/054421 A1 | 4/2016 |
| WO | WO-2016/071857 A1 | 5/2016 |
| WO | WO-2016/077123 A1 | 5/2016 |
| WO | WO-2016/077125 A1 | 5/2016 |

OTHER PUBLICATIONS

Orkin et al.,Report and Recommendations of the Panel to Assess the NIH Nvestment in Research on Gene Therapy. (Year: 1996).*
Ulrich-Vintlher. Acta orthopeadica Suppllementum 78(325 : 64 pages (Year: 2007).*
U.S. Appl. No. 61/494,882.
Adami, R.C. et al., An amino acid-based amphoteric liposomal delivery system for systemic administration of siRNA. Molecular Therapy 19(6):1141-1151 (2011).
Akinc, A. et al., A combinatorial library of lipid-like materials for delivery of RNAi therapeutics. Nature Biotechnology 26(5):561-569 (2008).
Akinc, A. et al., Development of lipidoid-siRNA formulations for systemic delivery to the liver. Molecular Therapy 17(5):872-879 (2009).
Alton et al., Cationic Lipid-Mediated CFTR Gene Transfer to the Lungs and Nose of Patients with Cystic Fibrosis: a Double-Blind Placebo-Controlled Trial, Lancet, 353: 947-954 (1999).
Anderson, D.G. et al., Structure/property studies of polymeric gene delivery using a library of poly(beta-amino esters). Molecular Therapy 11(3):426-434 (2005).
Anderson, D.M. et al., Stability of mRNA/Cationic Lipid Lipoplexes in Human and Rat Cerebrospinal Fluid: Methods and Evidence for Nonviral mRNA Gene Delivery to the Central Nervous System, Human Gene Therapy, 14:191-202 (2003).
Anderson, J. Biological Responses to Materials. Annual Review of Materials Research 31:81-110(2001).
Anderson, W. French, Human gene therapy, Nature, 392, 25-30 (1998).
Andries et al., Comparison of the Gene Transfer Efficiency of mRNA/GL67 and pDNA/GL67 Complexes in Respiratory Cells, Mol. Pharmaceut., 9: 2136-2145 (2012).
Auffray, C. et al., Purification of Mouse Immunoglubulin Heavy-Chain Messenger RNAs from Total Myeloma Tumor RNA, European Journal of Biochemistry, 107(2):303-314 (1980).
Author Unknown, Blood Proteins, published by WikiPedia, San Francisco, CA, 2 pages, <http://en.wikipedia.org/wiki/Biood_proteins> downloaded May 17, 2015.
Bahlke, M. A. et al., Progress towards in vivo use of siRNAs, Molecular Therapy, 13:644-670 (2006).
Bajaj, A. et al., Synthesis and gene transfection efficacies of PEI-cholesterol-based lipopolymers. Bioconjugate Chemistry 19(8):1640-516511 (2008).
Barreau, C. et al., Liposome-mediated RNA transfection should be used with caution, RNA, 12:1790-1793 (2006).
Behr et al., Efficient Gene Transfer into Mammalian Primary Endocrine Cells with Lipo Polyamine-Coated DNA, Proc. Nat.'l Acad. Sci., 86: 6982-6986 (1989).
Bennett, J. Immune response following intraocular delivery of recombinant viral vectors, Gene Therapy, 10: 977-982 (2003).
Bhaduri, S. et al., Procedure for the preparation of milligram quantities of adenovirus messenger ribonucleic acid, J. Virol., 10(6): 1126-1129 (1972).
Bloomfield, V.A., Quasi-Elastic Light Scattering Applications in Biochemistry and Biology, Ann. Rev. Biophys. Bioeng. 10:421-450 (1981).
Boussif, O. et al., A versatile vector for gene and oligonucleotide transfer into cells in culture and in vivo: polyethylenimine. Proceedings of the National Academy of Sciences of the USA. 92(16):7297-7301 (1995).
Braun, C.S. et al., Structure/function relationships of polyamidoamine/DNA dendrimers as gene delivery vehicles. Journal of Pharmaceutical Sciences 94(2):423-436 (2005).
Breunig, M. et al., Breaking up the correlation between efficacy and toxicity for nonviral gene delivery. Proceedings of the National Academy of Sciences of the U S A. 104(36): 14454-14459 (2007).
Breunig, M. et al., Mechanistic investigation of poly(ethylene imine)-based siRNA delivery: disulfide bonds boost intracellular release of the cargo. Journal of Controlled Release 130(1):57-63 (2008).

(56) References Cited

OTHER PUBLICATIONS

Brey, D.M. et al., Controlling poly(beta-amino ester) network properties through macromer branching. Acta Biomaterialia 4(2):207-217 (2008).
Brey, D.M. et al., Influence of macromer molecular weight and chemistry on poly(beta-amino ester) network properties and initial cell interactions. Journal of Biomedical Materials Research Part A 85(3):731-741 (2007).
Budker, V. et al., Protein/Amphipathic Polyamine Complexes Enable Highly Efficient Transfection with Minimal Toxicity, BioTechniques, 23: 139-147 (1997).
Burnett, J.C. et al., Current progress of siRNA/shRNA therapeutics in clinical trials. Biotechnology Journal 6(9):1130-1146 (2011).
Byk, G. et al., Synthesis, activity, and structure-activity relationship studies of novel cationic lipids for DNA transfer. Journal of Medical Chemistry 41(2):224-235 (1998).
Caplen, N.J. et al., In vitro liposome-mediated DNA transfection of epithelial cell lines using the cationic liposome DC-Chol/DOPE, Gene Therapy, 2:603-613 (1995).
Cassiman, D. Gene transfer for inborn errors of metabolism of the liver: the clinical perspective, Current Pharmaceutical Design, 17(24):2550-2557 (2011).
Castanotto, D. et al., The promises and pitfalls of RNA-interference-based therapeutics. Nature 457(7228):426-433 (2009).
Chakraborty, C. Potentiality of Small Interfering RNAs (siRNA) as Recent Therapeutic Targets for Gene-Silencing. Current Drug Targets 8(3):469-82 (2007).
Chandler, R. et al., Liver-directed adeno-associated virus serotype 8 gene transfer rescues a lethal murine model of citrullinemmia type 1, Gene Therapy, 20:1188-1191 (2013).
Chau, Y. et al., Investigation of targeting mechanism of new dextran-peptide-methotrexate conjugates using biodistribution study in matrix-metalloproteinase-overexpressing tumor xenograft model, J. Pharm. Sci., 95(3): 542-551 (2006).
Chen, D. et al., Rapid discovery of potent siRNA-containing lipid nanoparticles enabled by controlled microfluidic formulation. Journal of the American Chemical Society 134(16):6948-6951 (2012).
Chen, Y. and Huang, L., Tumor-targeted delivery of siRNA by non-viral vector: safe and effective cancer therapy. Expert Opinion on Drug Delivery 5(12):1301-1311 (2008).
Chiou, H.C. et al., Enhanced resistance to nuclease degradation of nucleic acids complexed to; asialoglycoprotein-polylysine carriers, Nucleic Acids Research, 22(24):5439-46 (1994).
Christensen, U.B. et al., Intercalating nucleic acids containing insertions of 1-O-(1-pyrenylmethyl)glycerol: stabilisation of dsDNA and discrimination of DNA over RNA, Nucl. Acids. Res., 30(22):4918-4925 (2002).
Conese et al., Gene and Cell Therapy for Cystic Fibrosis: From Bench to Bedside, J. Cyst. Fibros., 10 Suppl 2: S114-S128 (2011).
Cotten, M. et al., Receptor-mediated transport of DNA into eukaryotic cells. Methods in Enzymology 217 (H):618-644 (1993).
Cowling, V.H., Regulation of mRNA cap methylation, Biochemical Journal, 425:295-302 (2010).
Creusat, G. et al., Proton sponge trick for pH-sensitive disassembly of polyethylenimine-based siRNA delivery systems. Bioconjugate Chemistry 21(5):994-1002 (2010).
Crooke, S.T. Molecular mechanisms of action of antisense drugs. Biochimica et Biophysica Acta 1489(1):31-44. Review (1999).
Crystal, R.G. Transfer of genes to humans: early lessons and obstacles to success. Science 270(5235):404-410. Review (1995).
Damen, M. et al., Delivery of DNA and siRNA by novel gemini-like amphiphilic peptides. Journal of Controlled Release 145(1):33-39 (2010).
Dande, P. et al., Improving RNA interference in mammalian cells by 4'-thio-modified small interfering RNA (siRNA): effect on siRNA activity and nuclease stability when used in combination with 2'-0-alkyl modifications, Journal of Medicinal Chemistry, 49(5):1624-1634 (2006).

Davis, M. E., The first targeted delivery of siRNA in humans via a self-assembling, cyclodextrin polymer-based nanoparticle: from concept to clinic. Molecular Pharmacuetics 6(3):659-668 (2009).
Davis, M.E. et al., Evidence of RNAi in humans from systemically administered siRNA via targeted nanoparticles. Nature 464(7291):1067-1070 (2010).
Debus et al., Delivery of Messenger RNA Using Poly(ethylene imine)-poly(ethylene glycol)-Copolymer Blends for Polyplex Formation: Biophysical Characterization and In Vitro Transfection Properties, J. Control. Rel., 148: 334-343 (2010).
Decher, G. Fuzzy Nanoassemblies: Toward Layered Polymeric Multicomposites. Science 277: 1232-1237 (1997).
Demeshkina, N. et al., Interactions of the ribosome with mRNA and tRNA, Current Opinion in Structural Biology, 20(3):325-332 (2010).
Denardo, S.J. et al., Enhanced Therapeutic Index of Radioimmunotherapy (RIT) in Prostate Cancer Patients Comparison of Radiation Dosimetry for 1,4,7,10-Tetraazacyclododecane-N,N',N'',N'''-Tetraacetic Acid (DOTA)-Peptide versus 2IT-DOTA Monoclonal Antibody Linkage for RIT1, Clin. Cancer Res., 9: 3665s (2003).
Dern, R.J. et al., Toxicity studies of pyrimethamine (daraprim). The American Journal of Tropical Medicine and Hygiene 4(2):217-220 (1955).
Deshmukh, H. M and Huang, L., Liposome and polylysine mediated gene therapy. New Journal of Chemistry 21:113-124 (1997).
Discher, B.M. et al., Polymersomes: tough vesicles made from diblock copolymers. Science 284(5417):1143-1146 (1999).
Discher, D.E. and Eisenberg, A., Polymer vesicles. Science 297(5583):967-973. Review (2002).
Dong, Y. et al., Lipopeptide nanoparticles for potent and selective siRNA delivery in rodents and nonhuman primates, Proceedings of the National Academy of Sciences, 111(11): 3955-3960 (2014).
Drummond, D.C. et al., Optimizing Liposomes for Delivery of Chemotherapeutic Agents to Solid Tumors, Pharmacological Reviews, 51(4): 691-743 (1999).
Dwarki, V. et al., Cationic liposome-mediated RNA transfection, Methods in Enzymology, 217:644-654 (1993).
Elbashir, S.M. et al., RNA interference is mediated by 21- and 22-nucleotide RNAs. Genes & Development 15: 188-200 (2001).
Elton, C., The Next Next Big Thing, Boston Magazine, pp. 106-118 (Mar. 2013).
Emlen, W. et al., Effect of DNA size and strandedness on the in vivo clearance and organ localization of DNA, Clinical & Experimental Immunology, 56:185-192 (1984).
Eon-Duval, A. et al., Removal of RNA impurities by tangential flow filtration in an RNase-free plasmid DNA purification process, Analytical Biochemistry, 316(1):66-73 (2003).
Ernst et al., Interaction of Liposomal and Polycationic Transfection Complexes with Pulmonary Surfactant, J. Gene. Med., 1: 331-340 (1999).
Estimated Number of Animal and Plant Species on Earth, http://www.factmonster.com/ipka/A0934288.html, 2000-2014, 3 pages, (Retreived Aug. 2, 2014).
Ewert, K. et al., Cationic lipid-DNA complexes for gene therapy: understanding the relationship between complex structure and gene delivery pathways at the molecular level. Current Medicinal Chemistry 11(2): 133-149 (2004).
Fath, S. et al., Multiparameter RNA and Codon Optimization: A Standardized Tool to Assess and Enhance Autologous Mammalian Gene Expression, PLoS One, 6(3):e17596 (14 pages) 2011.
Fechter, P. et al., Recognition of mRNA cap structures by viral and cellular proteins, Journal of General Virology, 86:1239-1249 (2005).
Feigner et al., Lipofection: A Highly Efficient, Lipid-Mediated DNA-Transfection Procedure, Proc. Natl. Acad., 84: 7413-7417 (1987).
Felgner, P.L. and Ringold, G.M., Cationic liposome-mediated transfection, Nature, 337(6205):387-388 (1989).
Fenske, D.B. and Cullis, P., Liposomal nanomedicines. Expert Opinion on Drug Delivery 5(1):25-44 (2008).
Fernandez, V. et al., Cross Flow Filtration of RNA Extracts by Hollow Fiber Membrane, Acta Biotechnologica, 12(1):49-56 (1992).
Ferruti, P.F. and Barbucci, R., Linear amino polymers: Synthesis, protonation and complex formation. Advances in Polymer Science 58:55-92 (1984).

(56) References Cited

OTHER PUBLICATIONS

Ferruti, P.F. et al., A novel modification of poly(l-lysine) leading to a soluble cationic polymer with reduced toxicity and with potential as a transfection agent. Macromolecular Chemistry and Physics 199:2565-2575 (1998).
Fischer, D. et al., Effect of poly(ethylene imine) molecular weight and pegylation on organ distribution and pharmacokinetics; of polyplexes with oligodeoxynucleotides in mice, Drug Metabolism and Disposition, 32(9):983-92 (2004).
Fire, A. et al., Potent and specific genetic interference by double-stranded RNA in Caenorhabditis elegans. Nature 391(6669):806-811 (1998).
Fumoto et al., Targeted Gene Delivery: Importance of Administration Routes, Novel Gene Therapy Approaches, 3-31 (2013).
Furgeson, D.Y. et al., Modified linear polyethylenimine-cholesterol conjugates for DNA complexation. Bioconjugate Chemistry 14(4):840-847 (2003).
Furgeson, D.Y. et al., Novel water insoluble lipoparticulates for gene delivery. Pharmaceutical Research 19(4): 382-390 (2002).
Galipon, J. et al., Stress-induced lncRNAs evade nuclear degradation and enter the translational machinery, Genes to Cells, 18(5):353-368 (2013).
Gao, X. et al., A novel cationic liposome reagent for efficient transfection of mammalian cells, Biochemical and Biophysical Research Communications, 179(1):280-285 (1991).
Garbuzenko, O.B. et al., Intratracheal Versus Intravenous Liposomal Delivery of siRNA, Antisense Oligonucleotides and Anticancer Drug, Pharmaceutical Research, 26(2):382-394 (2009).
Geraerts, M. et al., Upscaling of lentiviral vector production by tangential flow filtration, Journal of Gene Medicine, 7(10):1299-1310 (2005).
Godbey, W.T. et al., Size matters: molecular weight affects the efficiency of poly(ethylenimine) as a gene delivery vehicle. Journal of Biomedical Materials Research 45(3):268-275 (1998).
Gonzalez, H. et al., New class of polymers for the delivery of macromolecular therapeutics. Bioconjugate Chemistry 10(6):1068-1074 (1999).
Gonzalez-Aseguinolaza, G. et al., Gene therapy of liver diseases: A 2011 perspective, Clinics and Research in Hepatology and Gastroenterology, 35(11):699-708 (2011).
Gordon, N. Ornithine transcarbamylase deficiency: a urea cycle defect, European Journal of Paediatric Neurology, 7:115-121 (2003).
Grayson, A.C.R. et al., Biophysical and structural characterization of polyethylenimine-mediated siRNA delivery in vitro. Pharmaceutical Research 23(8): 1868-1876 (2006).
Grudzien, E. et al., Novel cap analogs for in vitro synthesis of mRNAs with high translational efficiency, RNA Biology, 10(9):1479-1487 (2004).
Grunlan, M.A. et al., Synthesis of 1,9-bis[glycidyloxypropyl]penta(1'H, 1'H, 2'H, 2'H-perfluoroalkylmethylsiloxane)s and copolymerization with piperazine. Polymer 45:2517-2523 (2004).
Gupta, U. et al., A review of in vitro-in vivo investigations on dendrimers: the novel nanoscopic drug carriers. Nanomedicine: Nanotechnology, Biology, and Medicine 2(2):66-73 (2006).
Guttman, M. et al., Chromatin signature reveals over a thousand highly conserved large non-coding RNAs in mammals, Nature, 458:223-227 (2009).
Haensler, J. and Szoka, F., Polyamidoamine cascade polymers mediate efficient transfection of cells in culture. Bioconjugate Chemistry 4(5):372-379 (1993).
Harada-Shiba, M. et al., Polyion complex micelles as vectors in gene therapy—pharmacokinetics and in vivo; gene transfer, Gene Therapy, 9(6):407-14 (2002).
Harpe, A. Characterization of commercially available and synthesized polyethylenimines for gene delivery. Journal of Controlled Release 69:309-322 (2000).
Haskins M., Gene Therapy for Lysosomal Storage Disorders (LDSs) in Large Animal Models, ILAR J., 50(2):112-121 (2009).
Hata, A. et al., Isolation and Characterization of the Human Ornithine Transcarbamylase Gene: Structure of the 5'-End Region, Journal of Biochemistry, 100:717-725 (1986).
Hecker, J. et al., Advances in Self-Limited Gene Expression of Protective Intracellular Proteins In-Vivo in Rat Brain Using mRNA / Cationic Lipid Complexes, Anesthesia and Analgesia, 86(2S):346S (1994).
Heidenreich, O. et al., High Activity and Stability of Hammerhead Ribozymes Containing 2'-Modified Pyrimidine Nucleosides and Phosphorothioates, The Journal of Biological Chemistry, 269(3):2131-2138 (1994).
Henkin, R. I. et al., Inhaled Insulin—Intrapulmonary, intranasal, and other routes of administration: Mechanisms of action, Nutrition, 26: 33-39 (2010).
Hess et al., Vaccination with mRNAs Encoding Tumor-Associated Antigens and Granulocyte-Macrophage Colony-Stimulating Factor Efficiently Primes CTL Responses, but is Insufficient to Overcome Tolerance to a Model Tumor/Self Antigen, Cancer Immunology, Immunotherapy: CII, 55(6): 672-83 (2006).
Heyes, J. et al., Cationic lipid saturation influences intracellular delivery of encapsulated nucleic acids, Journal of Controlled Release, 107:276-287 (2005).
Higman, M.A. et al., The mRNA (Guanine-7-)methyltransferase Domain of the Vaccinia Virus mRNA Capping Enzyme, The Journal of Biological Chemistry, 269(21):14974-14981 (1994).
Hill, I.R.C. et al., In vitro cytotoxicity of poly(amidoamine)s: relevance to DNA delivery. Biochimica et Biophysica Acta 1427: 161-174 (1999).
Hill, J.G. et al., Enantioselective Epoxidation of Allylic Alcohols: (2S,3S)-3-Propyloxiranemethanol. Organic Syntheses Collection 7: 461 (1990) and 63: 66 (1985) (8 pages).
Hillery, A.M. et al., Drug Delivery and Targeting for Pharmacists and Pharmaceutical Scientists, Taylor and Francis (2005).
Hoerr et al., In Vivo Application of RNA Leads to Induction of Specific Cytotoxic T Lymphocytes and Antibodies, European Journal of Immunology, 30(1): 1-7 (2000).
Hofland, H.E.J et al., Formation of stable cationic lipid/DNA complexes for gene transfer. Proceedings of the National Academy of Sciences of the USA 93 (14): 7305-7309 (1996).
*Homo sapiens* galactosidase, alpha (GLA) mRNA, NCBI Reference Seguence NM_000169.1, Modification Date: Nov. 17, 2006.
Hope, M.J. et al., Cationic Lipids, Phosphatidylethanolamine and the Intracellular Delivery of Polymeric, Nucleic Acid-Based Drugs. Molecular Membrane Technology 15:1-14 (1998).
Hope, M.J. et al., Reduction of Liposome Size and Preparation of Unilamellar Vesicles by Extrusion Technigues, In: Liposome Technology, 1:123-139 (1993).
Hornung, V. et al., Quantitative expression of toll-like receptor 1-10 mRNA in cellular subsets of human peripheral blood mononuclear cells and sensitivity to CpG oligodeoxynucleotides. The Journal of Immunology 168: 4531-4537 (2002).
Horwich, A.L. et al., Structure and Expression of a Complementary DNA for the Nuclear Coded Precursor of Human Mitochondrial Ornithine Transcarbamylase, Science, 224(4653): 1068-1074 (1984).
Horwich, A.L. et al., Targeting of Pre-Ornithine Transcarbamylase to Mitochondria: Definition of Critical Regions and Residues in the Leader Peptide, Cell, 44:451-459 (1986).
Howard, K.A. Delivery of RNA interference therapeutics using polycation-based nanoparticles. Advanced Drug Delivery Reviews 61: 710-720 (2009).
Huang, Z. et al., Thiocholesterol-based lipids for ordered assembly of bioresponsive gene carriers, Molecular Therapy, 11(3):409-417 (2005).
Huttenhofer, A. and Noller, H., Footprinting mRNA-ribosome complexes with chemical probes, The EMBO Journal, 13(16):3892-3901 (1994).
Incani, V. et al., Lipid and hydrophobic modification of cationic carriers on route to superior gene vectors. Soft Matter 6: 2124-2138 (2010).
International Preliminary Report on Patentability for PCT/US2010/058457, 12 pages (dated Jun. 14, 2012).
International Search Report for PCT/US2010/058487, 4 pages (dated May 6, 2011).

(56) References Cited

OTHER PUBLICATIONS

International Search Report for PCT/US2011/062459, 3 pages (dated Apr. 11, 2012).
International Search Report for PCT/US2012/041663, 4 pages (dated Oct. 8, 2012).
International Search Report for PCT/US2012/041724, 5 pages (dated Oct. 25, 2012).
International Search Report for PCT/US2013/034602, 2 pages (dated Jun. 17, 2013).
International Search Report for PCT/US2013/034604, 4 pages (dated Jun. 17, 2013).
International Search Report for PCT/US2013/044769, 4 pages (dated Nov. 12, 2013).
International Search Report for PCT/US2013/044771, 6 pages (dated Nov. 1, 2013).
International Search Report for PCT/US2013/073672, 6 pages (dated Mar. 3, 2014).
International Search Report for PCT/US2014/027422, 5 pages (dated Jul. 31, 2014).
International Search Report for PCT/US2014/027585, 3 pages (dated Jul. 14, 2014).
International Search Report for PCT/US2014/027587, 6 pages (dated Jul. 24, 2014).
International Search Report for PCT/US2014/027602, 6 pages (dated Jul. 28, 2014).
International Search Report for PCT/US2014/027717, 5 pages (dated Jul. 16, 2014).
International Search Report for PCT/US2014/028330, 5 pages (dated Jul. 22, 2014).
International Search Report for PCT/US2014/028441, 6 pages (dated Jul. 22, 2014).
International Search Report for PCT/US2014/028498, 5 pages (dated Jul. 28, 2014).
International Search Report for PCT/US2014/028849, 6 pages (dated Jul. 17, 2015).
International Search Report for PCT/US2014/061786, 6 pages (dated Feb. 6, 2015).
International Search Report for PCT/US2014/061793, 4 pages (dated Feb. 6, 2015).
International Search Report for PCT/US2014/061830, 5 pages (dated Feb. 4, 2015).
International Search Report for PCT/US2014/061841, 6 pages (dated Feb. 24, 2015).
International Search Report for PCT/US2015/021403, 4 pages (dated Jun. 15, 2015).
International Search Report for PCT/US2015/027563, 5 pages (dated Sep. 18, 2015).
International Search Report for PCT/US2015/039004, 4 pages (dated Oct. 6, 2015).
Jakobsen, K. et al., Purification of MRNA Directly From Crude Plant Tissues in 15 Minutes Using Magnetic Oligo DT Microsheres, Nucleic Acids Research, 18(12):3669 (1990).
Jeffs, L.B. et al., A scalable, extrusion-free method for efficient liposomal encapsulation of plasmid DNA, Pharmacol. Res., 22(3): 362-372 (2005).
Jemielity, J. et al., Novel "anti-reverse" cap analogs with superior translational properties, Cold Spring Harbor Laboratory Press, 9(9):1108-1122 (2003).
Jiang, G. et al., Hyaluronic acid-polyethyleneimine conjugate for target specific intracellular delivery of siRNA. Biopolymers 89 (7): 635-642 (2008).
Jiang, M. et al., Electrochemically controlled release of lipid/DNA complexes: a new tool for synthetic gene delivery system. Electrochemistry Communications (6): 576-582 (2004).
Jiang, S. and Cao, Z., Ultralow-fouling, functionalizable, and hydrolyzable zwitterionic materials and their derivatives for biological applications. Advanced Materials 22(9):920-932 (2010).
Jolck, R.I. et al., Solid-phase synthesis of PEGylated lipopeptides using click chemistry. Bioconjugate Chemistry 21(5):807-810 (2010).
Jon, S. et al., Degradable poly(amino alcohol esters) as potential DNA vectors with low cytotoxicity. Biomacromolecules 4(6):1759-1762 (2003).
Jones, G. et al., Duplex- and Triplex-Forming Properties of 4'-Thio-Modified Oligodeoxynucleotides, Bioorganic & Medicinal Chemistry Letters, 7(10):1275-1278 (1997).
Kabanov, A.V. and Kabanov, V.A., DNA complexes with polycations for the delivery of genetic material into cells. Bioconjugate Chemistry 6(1): 7-20 (1995).
Kamath, S. et al., Surface chemistry influences implant-mediated host tissue responses. Journal of Biomedical Materials Research A 86(3):617-626 (2007).
Kariko, K. et al., Incorporation of Pseudouridine Into mRNA Yields Superior Nonimmunogenic Vector With Increased Translational Capacity and Biological Stability, Molecular Therapy, 16(11): 1833-1840 (2008).
Kariko, K. et al., In vivo protein expression from mRNA delivered into adult rat brain, Journal of Neuroscience Methods, 105:77-86 (2001).
Kasuya, T. et al., In Vivo Delivery of Bionanocapsules Displaying *Phaseolus vulgaris* Agglutinin-$L_4$ Isolectin to Malignant Tumors Overexpressing N-Acetylglucosaminyltransferase V, Human Gene Therapy, 19:887-895 (2008).
Kaur, N. et al., A delineation of diketopiperazine self-assembly processes: understanding the molecular events involved in Nepsilon-(fumaroyl)diketopiperazine of L-Lys (FDKP) interactions. Molecular Pharmaceutics 5(2):294-315 (2007).
Kaur, T. et al., Addressing the Challenge: Current and Future Directions in Ovarian Cancer THerapy, Current Gene Therapy, 9: 434-458 (2009).
Kiew, L.V. et al., Effect of antisense oligodeoxynucleotides for ICAM-1 on renal ischaemia-reperfusion injury in the anaesthetised rat, The Journal of Physiology, 557(3):981-989 (2004).
Kim, S.H. et al., Comparative evaluation of target-specific GFP gene silencing efficiencies for antisense ODN, synthetic siRNA, and siRNA plasmid complexed with PEI-PEG-FOL conjugate. Bioconjugate Chemistry 17(1): 241-244 (2006).
Kim, T. et al., Synthesis of biodegradable cross-linked poly(beta-amino ester) for gene delivery and its modification, inducing enhanced transfection efficiency and stepwise degradation. Bioconjugate Chemistry 16(5):1140-1148 (2005).
Klibanov, A. et al., Amphipathic polyethyleneglycols effectively prolong the circulation time of liposomes. Federation of European Biochemical Societies 268 (1): 235-237 (1990).
Kober et al., Optimized Signal Peptides for the Development of High Expressing CHO Cell Lines, Biotechnol. Bioeng., 110: 1164-1173 (2012).
Kodama, K. et al., The Features and Shortcomings for Gene Delivery of Current Non-Viral Carriers, Current Medicinal Chemistry, 13: 2155-2161 (2006).
Kore, A. and Charles, I., Synthesis and evaluation of 2'-O-allyl substituted dinucleotide cap analog for mRNA translation, Bioorganics & Medicinal Chemistry, 18:8061-8065 (2010).
Kore, A. and Shanmugasundaram, M., Synthesis and biological evaluation of trimethyl-substituted cap analogs, Bioorganic & Medicinal Chemistry, 18:880-884 (2008).
Kormann, M.S.D et al., Expression of therapeutic proteins after delivery of chemically modified mRNA in mice, Nature Biotechnology, 29(2):154-157 (2011).
Kozak, M. An analysis of 5'-noncoding sequences from 699 vertebrate messenger RNAs, Nucleic Acid Research, 15(20):8125-8148 (1987).
Krieg, P.A. et al., In vitro RNA synthesis with SP6 RNA polymerase, Methods in Enzymology, 155:397-415 (1987).
Kvasnica, M. et al., Platinum(II) complexes with steroidal esters of L-methionine and L-histidine: Synthesis, characterization and cytotoxic activity, Bioorganic & Medicinal Chemistry, 16:3704-3713 (2008).
Lam, J.K.W et al., Pulmonary delivery of therapeutic siRNA, Advanced Drug Delivery Reviews (2011).
Lasic, D.D. et al., Gelation of liposome interior: A novel method for drug encapsulation, FEBS, 312(2,3):255-258 (1992).
Lasic, D.D. Novel applications of liposomes, Trends in Biotechnology, 16:307-321 (1998).

(56) References Cited

OTHER PUBLICATIONS

Lee, S. et al., Stability and cellular uptake of polymerized siRNA (poly-siRNA)/polyethylenimine (PEI) complexes for efficient gene silencing. Journal of Controlled Release 141: 339-346 (2010).
Li, L. et al., Preparation and Gene Delivery of Alkaline Amino Acids-Based Cationic Liposomes, Archives of Pharmaceutical Research, 31(7):924-931 (2008).
Li, S. et al., In vivo gene transfer via intravenous administration of cationic lipid-protamine-DNA (LPD) complexes, Gene Therapy, 4:891-900 (1997).
Li, W. et al., Lipid-based Nanoparticles for Nucleic Acid Delivery, Pharmaceutical Research, 24(3):438-449 (2007).
Liebhaber, S.A. et al., Translation inhibition by an mRNA coding region secondary structure is determined by its proximity to the AUG initiation codon, Journal of Molecular Biology, 226(3):609-621 (1992).
Lim, Y. et al., A self-destroying polycationic polymer: biodegradable poly(4-hydroxy-l-proline ester). Journal of American Chemical Society 121: 5633-5639 (1999).
Lindgren, V. et al., Human Ornithine Transcarbamylase Locus Mapped to Band Xp21.1 Near the Duchenne Muscular Dystrophy Locus, Science, 226(2675):698-700 (1984).
Liu et al., COStar: a D-star Lite-based Dynamic Search Algorithm for Codon Optimization, Journal of Theoretical Biology, 344: 19-30 (2014).
Liu, Y. et al., Designer Lipids Advance Systemic siRNA Delivery, Molecular Therapy, 18(4):669-670 (2010).
Liu, Y. et al., Factors influencing the efficiency of cationic liposome-mediated intravenous gene delivery, Nature Biotechnology, 15:167-173 (1997).
Lo, K-M et al., High level expression and secretion of Fc-X fusion proteins in mammalian cells, Protein Engineering, 11(6):495-500 (1998).
Lorenzi, J. C. C. et al., Intranasal Vaccination with Messenger RNA as a New Approach in Gene Therapy: Use Against Tuberculosis, BMC Biotechnology, 10(77):1-11 (2010).
Love, K.T. et al., Lipid-like materials for low-dose, in vivo gene silencing. Proceedings of the National Academy of Sciences of the USA 107 (5): 1864-1869 (2010).
Lu, D. et al., Optimization of methods to achieve mRNA-mediated transfection of tumor cells in vitro and in vivo employing cationic liposome vectors, Cancer Gene Therapy, 1(4):245-52 (1994).
Lukyanov, A.N. and Torchilin, V.P., Micelles from lipid derivatives of water-soluble polymers as delivery systems for poorly soluble drugs. Advanced Drug Delivery Reviews 56: 1273-1289 (2004).
Luo, D. and Saltzman, M., Synthetic DNA delivery systems. Nature Biotechnology 18: 33-37. Review (2000).
Lynn, D.M. and Langer, R., Degradable Poly(β-amino esters):? Synthesis, Characterization, and Self-Assembly with Plasmid DNA. Journal of American Chemical Society 122(44): 10761-10768 (2000).
Lynn, D.M. et al., Accelerated discovery of synthetic transfection vectors: parallel synthesis and screening of a degradable polymer library. Journal of American Chemical Society 123(33): 8155-8156 (2001).
Lynn, D.M. et al., pH-Responsive Polymer Microspheres: Rapid Release of Encapsulated Material within the Range of Intracellular pH. Angewandte Chemie International Edition 40(9): 1707-1710 (2001).
Ma, M. et al., Developlment of Cationic Polymer Coatings to Regulate Foreign Body Responses. Advanced Healthcare Materials 23: H189-H194. Reviews (2011).
Maclachlan, I., Lipid nanoparticle-mediated delivery of messenger RNA, 1st International mRNA Health Conference; Tubingen Germany, (Oct. 24, 2013) Retrieved from the Internet: URL: <http://files.shareholder.com/downloads/ABEA-50QJTB/2628241206x0x699789/47543d12-db34-4e6e-88a9-f3ae5d97b1d2/MacLachlan_mRNA_Conf_2013>.
Maeda-Mamiya, R et al., In vivo gene delivery by cationic tetraamino; fullerene. Proceedings of National Academy of Sciences U S A, 107(12):5339-44 (2010).
Malone, R.W., et al., Cationic liposome-mediated RNA transfection, PNAS, 86:6077-6081 (1989).
Mammal, http://en.wikipedia.org/wiki/Mammal, 2007, Pearson Education, NY, NY, Author unkown (Source: The international union for conservation of nature and natural resources), 2 pages, (Retreived Aug. 2, 2014).
Mansour, H.M. et al., Nanomedicine in pulmonary delivery, International Journal of Nanomedicine, 4:299-319 (2009).
Margus, H. et al., Cell-penetrating peptides as versatile vehicles for oligonucleotide delivery. Molecular Therapy 20 (3): 525-533 (2012).
Martell, A.E. and Chaberek, S., The Preparation and the Properties of Some N,N'-Disubstituted-ethylenediaminedipropionic Acids. Journal of the American Chemical Society 72: 5357-5361 (1950).
Martinon et al., Induction of Virus-Specific Cytotoxic T Lymphocytes in Vivo by Liposome-Entrapped mRNA, European Journal of Immunology, 23(7): 1719-22 (1993).
Mathiowitz, E. and Langer, R., Polyanhydride microspheres as drug carriers I. Hot-melt microencapsulation. Journal of Controlled Release 5: 13-22 (1987).
Mathiowitz, E. et al., Novel microcapsules for delivery systems. Reactive Polymers 6: 275-283 (1987).
Mathiowitz, E. et al., Polyanhydride microspheres as drug carriers II. Microencapsulation by solvent removal. Journal of Applied Polymer Sciences 35: 755-774 (1988).
McCracken, S. et al., 5'-Capping Enzymes are Targeted to Pre-MRNA by Binding to the Phosphorylated Carboxy-Terminal Domain of RNA Polymerase II, Genes and Development, 22(24):3306-3318 (1997).
McIvor, R. S., Therapeutic Delivery of mRNA: The Medium is the Message, Molecular Therapy, 19(5):822-823 (2011).
Melton, D.A. et al., Efficient in vitro synthesis of biologically active RNA and RNA hybridization probes from; plasmids containing a bacteriophage SP6 promoter, Nucleic Acids Research, 12(18):7035-56 (1984).
Mendelsohn, J.D. et al., Rational design of cytophilic and cytophobic polyelectrolyte multilayer thin films. Biomacromolecules 4(1): 96-106 (2003).
Merkel, O.M. et al., Nonviral Pulmonary Delivery of siRNA, Accounts of Chemical Research, 10 pages (2011).
Merten, O. et al., Large-Scale Manufacture and Characterization of a Lentiviral Vector Produced for Clinical Ex Vivo Gene Therapy Application, Human Gene Therapy, 22(3):343-356 (2011).
Miller, A. Cationic Liposomes for Gene Therapy. Angewandte Chemie International Edition 37: 1768-1785(1998).
Monia, B.P. et al., Evaluation of 2'-Modified Oligonucleotides Containing 2'-Deoxy Gaps as Antisense Inhibitors of Gene Epression, The Journal of Biological Chemistry, 268(19):14514-14522 (1993).
Morrissey et al., Potent and Persistent in vivo Anti-HBV Activity of Chemically Modified siRNAs, Nat. Biotechnol., 23(8): 1003-1007 (2005).
Narang, A.S. et al., Cationic lipids with increased DNA binding affinity for nonviral gene transfer in dividing and nondividing cells. Bioconjugate Chemistry 16(1): 156-168 (2005).
Navarro, G. et al., Phospholipid-polyethylenimine conjugate-based micelle-like nanoparticles for siRNA delivery. Drug Delivery and Translational Research 1: 25-33 (2011).
Neamnark, A. et al., Aliphatic lipid substitution on 2 kDa polyethylenimine improves plasmid delivery and transgene expression. Molecular Pharmaceutics 6(6): 1798-1815 (2009).
Ng, J. et al., LincRNAs join the pluripotency alliance, Nature Genetics, 42:1035-1036 (2010).
Nguyen, D.N. et al., A novel high-throughput cell-based method for integrated quantification of type I interferons and in vitro screening of immunostimulatory RNA drug delivery. Biotechnology and Bioengineering 103(4): 664-675 (2009).
Nguyen, D.N. et al., Drug delivery-mediated control of RNA immunostimulation. Molecular Therapy 17(9): 1555-1562 (2009).
Nojima, T. et al., The Interaction between Cap-binding Complex and RNA Export Factor is Required for Intronless mRNA Export, Journal of Biological Chemistry, 282(21):15645-15651 (2007).

(56) References Cited

OTHER PUBLICATIONS

Nori, A. et al., Tat-conjugated synthetic macromolecules facilitate cytoplasmic drug delivery to human ovarian carcinoma cells, Bioconj. Chern., 14(1): 44-50 (2003).
Okumura, K. et al., Bax mRNA therapy using cationic liposomes for human malignant melanoma, The Journal of Gene Medicine, 10:910-917 (2008).
Otsuka, Y. et al., Identification of a Cytoplasmic Complex That Adds a Cap onto 5'-Monophosphate RNA, Molecular and Cellular Biology, 29(8):2155-2167 (2009).
Ozer, A., Alternative applications for drug delivery: nasal and pulmonary routes, Nanomaterials and Nanosystems for Biomedical Applications, M.R. Mozafari (ed.): 99-112 (2007).
Painter et al., Topical Delivery of mRNA to the Murine Lung and Nasal Epithelium, Molecular Therapy, 9: S187 (2004).
Painter, An Investigation of mRNA as a Gene Transfer Agent, Gene Medicine Research Group Nuffield Department of Clinical Laboratory Sciences and Merton College, University of Oxford, 1-282 (2007).
Painter, An Investigation of mRNA as a Gene Transfer Agent, Oxford University GeneMedicine, Abstract Only, 1 page (2007).
Palu, et al., In pursuit of new developments for gene therapy of human diseases, Journal of Biotechnology, vol. 68:1-13 (1999).
Parrish, D.A. and Mathias, L.J., Five- and six-membered ring opening of pyroglutamic diketopiperazine. Journal of Organic Chemistry 67(6): 1820-1826 (2002).
Paulus, C. and Nevels, M., The Human Cytomegalovirus Major Immediate-Early Proteins as Antagonists of Intrinsic and Innate Antiviral Host Responses, Viruses, 1:760-779 (2009).
Peppas, N.A. et al., Hydrogels in Biology and Medicine: From Molecular Principles to Bionanotechnology. Advanced Materials 18: 1345-1360 (2006).
Philipp, A. et al., Hydrophobically modified oligoethylenimines as highly efficient transfection agents for siRNA delivery. Bioconjugate Chemistry 20(11): 2055-2061 (2009).
Pons, M. et al., Liposomes obtained by the ethanol injection method, Int. J. Pharm., 95: 51-56. (1993).
Prata, C.A. et al., Lipophilic peptides for gene delivery. Bioconjugate Chemistry 19(2): 418-420 (2008).
Probst, J. et al., Spontaneous cellular uptake of exogenous messenger RNA in vivo is nucleic acid-specific, saturable and ion dependent, Gene Therapy, 14:1175-1180 (2007).
Promega, PolyATtract mRNA Isolation Systems, Instructions for Use of Products Z5200, Z5210, Z2300 and Z5310, Technical Manual (2012).
Politz, et al., Characterization of hybridization between synthetic oligodeoxynucleotides and RNA in living cells, Nucleic Acids Research, vol. 23, No. 24: 4946-4953 (1995).
Putnam, D. Polymers for gene delivery across length scales. Nature Materials 5: 439-451 (2006).
Putnam, D. and Langer, R., Poly(4-hydroxy-l-proline ester): Low-Temperature Polycondensation and Plasmid DNA Complexation. Macromolecules 32(11): 3658-3662 (1999).
Qiagen, Oligotex Handbook, Second Edition (2002).
Rabinovich, P.M. et al., Synthetic Messenger RNA as a Tool for Gene Therapy, Human Gene Therapy, 17:1027-1035 (2006).
Raper, S.E. et al., Developing adenoviral-mediated in vivo gene therapy for ornithine transcarbamylase deficiency, Journal of Inherited Metabolic Disease, 21:119-137 (1998).
Ratajczak, J. et al., Membrane-derived microvesicles: important and underappreciated mediators of cell-to-cell communication, Leukemia, 20:1487-1495 (2006).
Ratner, B.D. and Bryant, S., Biomaterials: where we have been and where we are going. Annual Review of Biomedical Engineering 6: 41-75 (2004).
Rejman, J. et al., Characterization and transfection properties of lipoplexes stabilized with novel exchangeable polyethylene glycol-lipid conjugates, Biochimica et Biophysica Acta, 1660:41-52 (2004).
Romano, et al., Biochemical and Molecular Characterization of Hereditary Myeloperoxidase Deficiency, Blood, vol. 90, No. 10: 4126-4134 (1997).
Rosenecker et al., Gene Therapy for Cystic Fibrosis Lung Disease: Current Status and Future Perspectives, Curr. Opin. Mol. Ther., 8: 439-445 (2006).
Rosenecker et al., Interaction of Bronchoalveolar Lavage Fluid with Polyplexes and Lipoplexes: Analysing the Role of Proteins and Glycoproteins, J. Gene. Med., 5: 49-60 (2003).
Rowe et al., Cystic Fibrosis, New Engl. J. Med. 352: 1992-2001 (2005).
Ryng, S. et al., Synthesis and structure elucidation of 5-aminomethinimino-3-methyl-4-isoxazolecarboxylic acid phenylamides and their immunological activity. Arch. Pharm. Pharm. Med. Chem 330(11):319-26 (1997).
Sahay, G. et al., Endocytosis of nanomedicines. Journal of Controlled Release 145: 182-195 (2010).
Sakiyama-Elbert, S.E. and Hubbell, J.A., Functional Biomaterials: Design of Novel Biomaterials. Annual Review of Materials Research 31: 183-201 (2001).
Schnierle, B.S. et al., Cap-specific mRNA (nucleoside-O2'-)-methyltransferase and poly(A) polymerase stimulatory activities of vaccinia virus are mediated by a single protein, Proceedings of the National Academy of Sciences, 89:2897-2901 (1992).
Schreier, H., The new frontier: gene and oligonucleotide therapy, Pharmaceutica Acta Helvetiae, 68(3):145-159 (1994).
Semple, S. et al., Rational design of cationic lipids for siRNA delivery, Nature Biotechnology, 28(2):172-178 (2010).
Shchori E., Poly(secondary Amine)s from Diacrylates and Diamines. Journal of Polymer Science 21(6):413-15 (1983).
Sherwood, R.F. Advanced drug delivery reviews: enzyme prodrug therapy, Adv. Drug Del. Rev., 22: 269-288 (1996).
Shimada, A. et al., Translocation Pathway of the Intratracheally Instilled Ultrafine Particles from the Lung into the Blood Circulation in the Mouse, Toxicologic Pathology, 34:949-957 (2006).
Siegwart, D.J. et al., Combinatorial synthesis of chemically diverse core-shell nanoparticles for intracellular delivery. Proceedings of the National Academy of the Sciences of the USA 108(32):12996-123001 (2011).
Simonova, O. et al., Enhanced cellular binding of concatemeric oligonucleotide complexes. Biochimica et Biophysica Acta 1758:413-418 (2006).
Smisterova, J. et al., Molecular Shape of the Cationic Lipid Controls the Structure of Cationic Lipid/Dioleylphosphatidylethanolamine-DNA Complexes and the Efficiency of Gene Delivery, The Journal of Biological Chemistry, 276(50):47615-47622 (2001).
Stern, L. et al., A novel antitumor prodrug platform designed to be cleaved by the endoprotease legumain, Bioconj. Chem., 20: 500-510 (2009).
Su, X. et al., Cytosolic Delivery Mediated Via Electrostatic Surface Binding of mRNA To Degradable Lipid-Coated Polymeric Nanoparticles, Polymer Preprints, 51(2):668-669 (2010).
Su, X. et al., In Vitro and in Vivo mRNA Delivery Using Lipid-Enveloped pH-Responsive Polymer Nanoparticles, Molecular Pharmaceutics, 8(3):774-787 (2011).
Szoka, F. and Papahadjopoulos, D., Comparative properties and methods of preparation of lipid vesicles (liposomes). Annual Review of Biophysics Bioengineering 9: 467-508 (1980).
Tagawa, M. et al., Gene expression and active virus replication in the liver after injection of duck hepatitis B virus DNA into the peripheral vein of ducklings, Journal of Hepatology, 24:328-334(1996).
Takahashi, Y. et al., Development of safe and effective nonviral gene therapy by eliminating CpG motifs from plasmid DNA vector, Frontiers in Bioscience, S4: 133-141 (2012).
Tan, S. et al., Engineering Nanocarriers for siRNA Delivery. Small 7(7): 841-856 (2011).
Tang, F. and Hughes, J. et al., Introduction of a Disulfide Bond into a Cationic Lipid Enhances Transgene Expression of Plasmid DNA, Biochemical and Biophysical Research Communications, 242(1):141-145 (1998).
Tang, M.X. et al., In vitro gene delivery by degraded polyamidoamine dendrimers. Bioconjugate Chemistry 7(6): 703-714 (1996).

(56) References Cited

OTHER PUBLICATIONS

Tarcha, P.J. et al., Synthesis and characterization of chemically condensed oligoethylenimine containing beta-aminopropionamide linkages for siRNA delivery. Biomaterials 28: 3731-3740 (2007).
Tavernier, G. et al., mRNA as gene therapeutic: How to control protein expression, Journal of Controlled Release, 150:238-247 (2011).
Tcherepanova, I. et al., Ectopic expression of a truncated CD40L protein from synthetic post-transcriptionally capped RNA in dendritic cells induces high levels of IL-12 secretion, BMC Molecular Biology, 9(1):pp. 1-13 (2008).
Theus, S. and Liarakos, C., A Simple Assay for Determining the Capping Efficiencies of RNA Polymerases Used for In Vitro Transcription, BioChromatography, 9(5):610-614 (1990).
Third Party Preissuance Submission Under 37 CFR § 1.290 (Oct. 25, 2013).
Thomas, C. E. et al., Progress and problems with the use of viral vectors for gene therapy, Nature Reviews/Genetics, 4: 346-358 (2003).
Thompson, P.E. et al., Antiamebic action of 5-chloro-7-diethylaminomethyl-8-quinolinol and of other substituted 8-quinolinols in vitro and in experimental animals. American Journal of Tropical Medicine and Hygiene 2(4): 224-248 (1955).
Toki, B.E. et al., Protease-mediated fragmentation of p-amidobenzyl ethers: a new strategy for the activation of anticancer prodrugs, J. Org. Chem., 67(6): 1866-1872 (2002).
Tranchant, I. et al., Physicochemical optimisation of plasmid delivery by cationic lipids. Journal of Gene Medicine 6: S24-S35 (2004).
Tsui, N.B. et al., Stability of endogenous and added RNA in blood specimens, serum, and plasma, Clinical Chemistry, 48(10):1647-53 (2002).
Tsvetkov, D.E. et al., Neoglycoconjugates based on dendrimeric poly(aminoamides). Russian Journal of Bioorganic Chemistry 28(6): 470-486 (2002).
Tuschl, T. et al., Targeted mRNA degradation by double-stranded RNA in vitro, Genes and Development, 13(24):3191-7 (1999).
Urban-Klein, B. et al., RNAi-mediated gene-targeting through systemic application of polyethylenimine (PEI)-complexed siRNA in vivo. Gene Therapy 12(5): 461-466 (2005).
Van Balen, G.P. et al., Liposome/water lipophilicity: methods, information content, and pharmaceutical applications. Medicinal Research Reviews 24(3): 299-324 (2004).
Van Der Gun, B.T.F et al., Serum insensitive, intranuclear protein delivery by the multipurpose cationic lipid Saint-2, Journal of Controlled Release, 123:228-238 (2007).
Van De Wetering, P. et al., Structure-activity relationships of water-soluble cationic methacrylate/methacrylamide polymers for nonviral gene delivery. Bioconjugate Chemistry 10(4): 589-597 (1999).
Vandenbroucke, R.E. et al., Prolonged gene silencing in hepatoma cells and primary hepatocytes after small interfering RNA delivery with biodegradable poly(beta-amino esters). Journal of Gene Medicine 10: 783-794 (2008).
Van Tendeloo, V.F.I et al., mRNA-based gene transfer as a tool for gene and cell therapy, Current Opinion in Molecular Therapeutics, 9(5):423-431 (2007).
Varambally, S. et al., Genomic Loss of microRNA-101 Leads to Overexpression of Histone Methyltransferase EZH2 in Cancer, Science, 322:1695-1699 (2008).
Verma, et al., Gene therapy—promises, problems and prospects, Nature, 389 (6648):239-242 (1997).
Veronese, F.M. et al., PEG-doxorubicin conjugates: influence of polymer structure on drug release, in vitro cytotoxicity, biodistribution, and antitumor activity, Bioconj. Chem., 16(4): 775-784 (2005).
Vester, et al., LNA (Locked Nucleic Acid): High-Affinity Targeting of Complementary RNA and DNA, Biochemistry, vol. 43, No. 42: 13233-13241 (2004).
Viecelli, H. et al., Gene Therapy for Hepatic Diseases Using Non-Viral Minicircle-DNA Vector, Journal of Inherited Metabolic Disease, 35(1):S144 (2012).
Viecelli, H. et al., Gene therapy for liver diseases using non-viral minicircle-DNA vector, Human Gene Therapy, 23(10):A145 (2012).
Viecelli, H. et al., Gene therapy for liver diseases using non-viral minicircle-DNA vector, Molecular Therapy, 21(1):S136 (2013).
Vomelova, I. et al., Methods of RNA Purification. All Ways (Should) Lead to Rome, Folia Biologica, 55(6):242-251 (2009).
Von Harpe et al., Characterization of commercially available and synthesized polyethylenimines for gene delivery. Journal of Controlled Release 69(2):309-322 (2000).
Walde, P. et al., Preparation of Vesicles (Liposomes). Encyclopedia of Nanoscience and Nanotechnology. Nalwa, ed. American Scientific Publishers, Los Angeles 9:43-79 (2004).
Wang, H. et al., N-acetylgalactosamine functionalized mixed micellar nanoparticles for targeted delivery of siRNA to liver, Journal of Controlled Release, 166(2):106-114 (2013).
Wang, Y. et al., Systemic delivery of modified mRNA encoding herpes simplex virus 1 thymidine kinase for targeted cancer gene therapy, Molecular Therapy, 21(2):358-367 (2013).
Webb, M. et al., Sphinogomyeline-cholesterol liposomes significantly enhance the pharmacokinetic and therapeutic properties of vincristine in murine and human tumour models, British Journal of Cancer, 72(4):896-904 (1995).
Werth, S. et al., A low molecular weight fraction of polyethylenimine (PEI) displays increased transfection efficiency of DNA and siRNA in fresh or lyophilized complexes. Journal of Controlled Release 112: 257-270 (2006).
Wetzer, B. et al., Reducible cationic lipids for gene transfer, Biochem. J., 356:747-756 (2001).
White, J.E. et al., Poly(hydroxyaminoethers): A New Family of Epoxy-Based Thermoplastics. Advanced Materials 12(23): 1791-1800 (2000).
White, J.E. et al., Step-growth polymerization of 10,11-epoxyundecanoicacid. Synthesis and properties of a new hydroxy-functionalized thermopastic polyester. Advanced Materials 48: 3990-3998 (2007).
Whitehead, K.A. et al., Knocking down barriers: advances in siRNA delivery. Nature Reviews Drug Discovery 8(2): 129-139 (2009).
Wiehe, J.M. et al., mRNA-mediated gene delivery into human progenitor cells promotes highly efficient protein expression, Journal of Cellular and Molecular Medicine, 11(3):521-530 (2007).
Williams, D. et al., A simple, highly efficient method for heterologous expression in mammalian primary neurons using cationic lipid-mediated mRNA transfection, Frontiers in Neuroscience, 4(181):1-20 (2010).
Wolf, J.A. et al., Protein/Amphipathic Polyamine Complexes Enable Highly Efficient Transfection with Minimal Toxicity, BioTechniques, 23:139-147 (1997).
Written Opinion for PCT/US2010/058457, 14 pages (dated May 6, 2011).
Written Opinion for PCT/US2011/062459, 9 pages (dated Apr. 11, 2012).
Written Opinion for PCT/US2012/041663, 7 pages (dated Oct. 8, 2012).
Written Opinion for PCT/US2012/041724, 11 pages (dated Oct. 25, 2012).
Written Opinion for PCT/US2013/034602, 4 pages (dated Jun. 17, 2013).
Written Opinion for PCT/US2013/034604, 9 pages (dated Jun. 17, 2013).
Written Opinion for PCT/US2013/044769, 8 pages (dated Nov. 12, 2013).
Written Opinion for PCT/US2013/044771, 7 pages (dated Nov. 1, 2013).
Written Opinion for PCT/US2013/073672, 7 pages (dated Mar. 3, 2014).
Written Opinion for PCT/US2014/027587, 5 pages (dated Jul. 24, 2014).
Written Opinion for PCT/US2014/027422, 6 pages (dated Jul. 31, 2014).
Written Opinion for PCT/US2014/027602, 7 pages (dated Jul. 28, 2014).
Written Opinion for PCT/US2014/027717, 5 pages (dated Jul. 16, 2014).

(56) References Cited

OTHER PUBLICATIONS

Written Opinion for PCT/US2014/028330, 7 pages (dated Jul. 22, 2014).
Written Opinion for PCT/US2014/028441, 6 pages (dated Jul. 22, 2014).
Written Opinion for PCT/US2014/028498, 6 pages (dated Jul. 28, 2014).
Written Opinion for PCT/US2014/028849, 7 pages (dated Jul. 17, 2015).
Written Opinion for PCT/US2014/061786, 5 pages (dated Feb. 6, 2015).
Written Opinion for PCT/US2014/061793, 4 pages (dated Feb. 6, 2015).
Written Opinion for PCT/US2014/061830, 7 pages (dated Feb. 4, 2015).
Written Opinion for PCT/US2014/061841, 8 pages (dated Feb. 24, 2015).
Written Opinion for PCT/US2015/021403, 7 pages (dated Jun. 15, 2015).
Written Opinion for PCT/US2015/027563, 12 pages (dated Sep. 18, 2015).
Written Opinion for PCT/US2015/039004, 8 pages (dated Oct. 6, 2015).
Wu, J. and Zern, M., Modification of liposomes for liver targeting, Journal of Hepatology, 24(6):757-763 (1996).
Wu, J. et al., Cationic lipid polymerization as a novel approach for constructing new DNA delivery agents. Bioconjugate Chemistry 12(2): 251-257 (2001).
Wurdinger, T. et al., A secreted luciferase for ex-vivo monitoring of in vivo processes, Nat. Methods, 5(2):171-173 (2008).
Yamamoto et al., Important Role of the Proline Residue in the Signal Seguence that Directs the Secretion of Human Lysozyme in *Saccharomyces cerevisiae*, Biochemistry, 28:2728-2732 (1989).
Yamamoto, A. et al., Current prospects for mRNA gene delivery, European Journal of Pharmaceutics and Biopharmaceutics, 71:484-489 (2009).
Yasuda et al., Fabry Disease: Novel [alpha]-Galactosidase A 3-terminal Mutations Result in Multiple Transcripts Due to Aberrant 3-End Formation, American Journal of Human Genetics, 73: 162-73 (2003).
Ye, X. et al., Nucleic Acids, Protein Synthesis, and Molecular Genetics: Prolonged Metabolic Correction in Adult Ornithine Transcarbamylase-deficient Mice with Adenoviral Vectors, The Journal of Biological Chemistry, 271:3639-3646 (1996).
Yokoe, H. et al., Spatial dynamics of GFP-tagged proteins investigated by local fluorescence enhancement, Nature Biotechnology, 14(10):1252-1256 (1996).
Yoneda et al., A cell-penetrating peptidic GRP78 ligand for tumor cell-specific prodrug therapy, Bioorg. Med. Chern. Lett., 18(5): 1632-1636 (2008).
Yoshioka, Y. and Calvert, P., Epoxy-based Electroactive Polymer Gels. Experimental Mechanics 42(4): 404-408 (2002).
Zagridullin, P.H. et al., Monobasic amines. II. Cycloalkylation and hydroxyalkylation of cyclic and acyclic di- and polyamines. Journal of Organic Chemistry26(1):184-88. Russian (1990).
Zaugg, H.E. et al., 3-Carboxy-2,5-piperazinedione and Derivatives. Journal of American Chemical Society 78(11):2626-2631 (1956).
Zauner, W.et al., Polylysine-based transfection systems utilizing receptor-mediated delivery. Advanced Drug Delivery Reviews 30(1-3):97-113(1998).
Zintchenko, A. et al., Simple modifications of branched PEI lead to highly efficient siRNA carriers with low toxicity. Bioconjugate Chemistry 19(7): 1448-1455 (2008).
Zou, S. et al., Lipid-mediated delivery of RNA is more efficient than delivery of DNA in non-dividing cells, International Journal of Pharmaceutics, 389(1-2):232-243 (2010).

* cited by examiner

NUCLEASE RESISTANT POLYNUCLEOTIDES AND USES THEREOF

CROSS-REFERENCE TO RELATED APPLICATIONS

This application is a Continuation Application of U.S. patent application Ser. No. 14/406,424, filed on Dec. 8, 2014, which is a National Stage Entry of International Application No. PCT/US2013/044769, filed on Jun. 7, 2013, which claims the benefit of U.S. Provisional Application No. 61/657,465, filed on Jun. 8, 2012, the disclosure of which is incorporated herein by reference.

INCORPORATION-BY-REFERENCE OF SEQUENCE LISTING

The contents of the file named "MRT-1089US2_ST25", which was created on Aug. 19, 2021 and is 2.10 KB in size, are hereby incorporated by reference in their entirety.

BACKGROUND

The administration of exogenous nucleic acids and polynucleotides, for example DNA vectors and plasmids, to a subject for the treatment of protein or enzyme deficiencies represents a significant advance in the treatment of such deficiencies however, the administration of such exogenous nucleic acids to a subject remains especially challenging. For example, gene therapies that rely on viruses to carry and deliver exogenous polynucleotides (e.g., DNA) to host cells and that cause the integration of such polynucleotides into the host cells' genome are capable of eliciting serious immunological and inflammatory responses. Furthermore, in certain Instances the integration of such exogenous polynucleotides into the host cells' genome has the potential of misregulating the expression of the host's endogenous genes and unpredictably impacting cellular activity.

Similarly, plasmid vector expression systems have represented an attractive alternative approach for gene therapy because of their ease of preparation, stability, and relative safety compared to viral vectors. Such plasmids are however, frequently characterized as having highly inefficient cellular uptake in vivo.

To date, the treatment of protein (e.g., enzyme) deficiencies have primarily involved the administration of recombinantly-prepared proteins (e.g., enzymes) to the affected subject. While in some instances, the use of recombinant proteins and enzymes may provide a means of ameliorating the symptoms of the underlying deficiency, the utility of such therapies are often limited and are not considered curative. Furthermore, recombinant proteins or enzymes are often prepared using non-human cell lines and may lack certain post-translational modifications (e.g., human glycosylation) relative to their endogenously produced counterparts. Such differences may contribute to the lower efficacy of such recombinantly-prepared proteins or enzymes and/or may contribute to their immunogenicity and the incidence of adverse reactions (e.g., infusion-related reactions such as fever, pruritus, edema, hives and other allergic-like symptoms). Recombinant protein and enzyme replacement therapies are also associated with great financial expense. For example, the average cost for enzyme replacement therapy in the United States may approach $200,000-$300,000 USD per year depending on the subject's weight and proscribed dose. (Brady, R O., *Annual Review of Medicine* (2006), 57: 283-296.) Since replacement therapies are not curative, the costs associated with, for example, enzyme replacement therapies impose a significant burden on the already taxed healthcare system. Further contributing to the costs associated with such therapies, such therapies often require the administration of multiple weekly or monthly doses, with each such dose being administered by a qualified healthcare professional.

The administration of polynucleotides such as RNA (e.g., mRNA) that do not have to be transcribed may also represent a suitable alternative to protein or enzyme replacement therapies. While the development of exogenous therapeutic mRNA polynucleotides encoding functional proteins or enzymes represents a promising advancement, in practice the utility of such treatments may be limited by the poor stability of such polynucleotides in vivo. In particular, the poor stability of exogenous polynucleotides may result in the inefficient expression (e.g., translation) of such polynucleotides, further resulting in a poor production of the protein or enzyme encoded thereby. Especially detrimental to the ability of mRNA polynucleotides to be efficiently translated into a functional protein or enzyme is the environment to which such polynucleotides are exposed in vivo. Following the administration of a polynucleotide, the polynucleotide may undergo degradation, for example upon exposure to one or more nucleases in vivo. Ribonucleases (e.g., endoribonucleases and exoribonucleases) represent a class of nuclease enzymes that are capable of catalyzing the degradation of RNA polynucleotides into smaller components and thereby render the polynucleotide ineffective. Nuclease enzymes (e.g., RNase) are therefore capable of shortening the circulatory half-life (t½) of, for example, exogenous or recombinantly-prepared mRNA polynucleotides. As a result, the polynucleotide is not translated, the polynucleotide is prevented from exerting an intended therapeutic benefit and its efficacy significantly reduced.

Previous efforts to stabilize polynucleotides have focused on complexing the polynucleotide with, for example, a liposomal delivery vehicle. While such means may positively impact the stability of the encapsulated polynucleotides, many lipids used as a component of such liposomal vehicles (e.g., cationic lipids) may be associated with toxicity. Other efforts have been directed towards the modification of one or more nucleotides that comprise the polynucleotide.

Novel, cost effective and therapeutically efficient approaches and therapies are still needed for the treatment of protein and enzyme deficiencies. Particularly needed are strategies and therapies which overcome the challenges and limitations associated with the administration of exogenous mRNA polynucleotides, including for example, novel methods and compositions relating to the stabilization of exogenous polynucleotides. Also needed are polynucleotides (e.g., RNA) and compositions that exhibit enhanced stability (e.g., increased half-life in vivo) and nuclease resistance and which facilitate the efficient expression or production of functional proteins or enzymes. The development of such stable and/or nuclease resistant compositions are necessary to overcome the limitations of conventional gene therapy and could provide viable treatments or even cures for diseases associated with the aberrant production of proteins or enzymes.

SUMMARY OF THE INVENTION

Disclosed herein are nuclease resistant polynucleotides and related compositions and methods. Such polynucleotides and compositions generally encode functional polypeptides, proteins and/or enzymes (e.g., an mRNA polynucleotide may encode a functional urea cycle enzyme). In certain embodiments, such compositions are characterized as being more resistant to nuclease degradation relative to their unmodified or native counterparts.

Disclosed herein are methods of stabilizing or modulating (e.g., increasing or otherwise improving) the nuclease resistance of a polynucleotide (e.g., an RNA polynucleotide). The polynucleotides that are the subject of the present inventions preferably encode a functional expression product (e.g., a protein or enzyme) and may be generally characterized as comprising both a coding region and a non-coding region. In some embodiments, the methods disclosed herein generally comprise a step of contacting the non-coding region of the polynucleotide (e.g., the poly-A tail of an mRNA polynucleotide) with a complementary (e.g., a perfectly complementary) stabilizing oligonucleotide under suitable conditions, thereby causing the stabilizing oligonucleotide to hybridize to the non-coding region of the polynucleotide. Upon hybridizing of the stabilizing oligonucleotide (e.g., a 15-mer poly-U oligonucleotide) to the polynucleotide, the polynucleotide is rendered more resistant to nuclease degradation. For example, in certain embodiments, provided herein are methods of increasing the nuclease resistance of an mRNA polynucleotide comprising a poly-A tail by contacting the poly-A tail of such polynucleotide with a complementary poly-U stabilizing oligonucleotide. Upon hybridizing to the non-coding region of the polynucleotide (e.g., the poly-A tail) to form a duplexed or double-stranded region, nuclease degradation of the polynucleotide may be reduced, delayed or otherwise prevented. Without wishing to be bound by any particular theories, it is believed that the observed stability and nuclease resistance of the polynucleotides disclosed herein is due in part to the single-stranded specificity of some nuclease enzymes (e.g., ribonucleases).

In certain embodiments, the stabilizing oligonucleotides disclosed herein may hybridize to the non-coding region of the polynucleotide (e.g., the 5' or 3' non-coding regions of an mRNA polynucleotide) so as not to interfere with the message encoded by the coding region of such polynucleotide. Stabilizing oligonucleotides may be prepared such that they are perfectly complementary to a fragment of the non-coding region (e.g., perfectly complementary to a fragment of the poly-A tail of an mRNA polynucleotide). For example, the stabilizing oligonucleotide may be complementary (e.g., at least about 50%, 55%, 60%, 65%, 70%, 75%, 80%, 85%, 87.5%, 90%, 92.5%, 95%, 97%, 98%, 99% or 100% complementary) to one or more non-coding regions of the polynucleotide selected from the group of regions consisting of the 3' untranslated region (UTR), the 5' untranslated region (UTR), the poly-A tail and a terminal cap. Similarly, the stabilizing oligonucleotide may be complementary (e.g., perfectly complementary) to a region spanning discreet structures within the non-coding region. For example, a stabilizing oligonucleotide may be prepared such that it is perfectly complementary to a region (or fragment of a region) that spans either the 3' UTR and the poly-A tail or alternatively the 5' UTR and a 5' cap structure.

While certain embodiments described herein contemplate the hybridization of the stabilizing oligonucleotide to the non-coding region of the polynucleotide, the present inventions are not limited to such embodiments. Rather, also contemplated are methods and compositions in which the stabilizing oligonucleotide hybridizes to a region spanning or comprising both a fragment of the coding region as well as a fragment of the non-coding region of the polynucleotide. In such embodiments (particularly where the non-coding region comprises the poly-A tail of the polynucleotide) hybridization to a region of the polynucleotide comprising fragments of both the coding and non-coding regions may provide a means to direct the hybridization of the stabilizing oligonucleotide to a specific region of the polynucleotide.

Also contemplated by the present invention is the administration of exogenous stabilizing oligonucleotides to a subject, for example, to treat a disease or condition associated with the aberrant expression or under-expression or production of a protein or enzyme. The foregoing may be particularly suitable for the treatment of diseases or conditions characterized as having a suboptimal or sub-therapeutic endogenous production of a protein or enzyme. In such embodiments, an exogenous stabilizing oligonucleotide that is complementary (e.g., perfectly complementary) to a region of the under expressed endogenous polynucleotide (e.g., one or more of the 5' and/or 3' UTR) is administered to a subject. Following administration of the exogenous oligonucleotide, such oligonucleotide may hybridize to the one or more endogenous polynucleotides (e.g., mRNA) encoding an under-expressed polypeptide, protein or enzyme such that the stability (e.g., the nuclease resistance) of the endogenous polynucleotide is modulated (e.g., enhanced or otherwise increased). The stabilized or nuclease resistant endogenous polynucleotide (e.g., mRNA) may be characterized as having an Increased circulatory half-life (t½) and/or an increased translational efficiency relative to its native counterpart, generally causing the amount of the expression product (e.g., a lysosomal enzyme) encoded by such endogenous polynucleotide to be enhanced or otherwise increased. In certain embodiments, the stabilizing oligonucleotide is delivered or administered in a suitable pharmaceutical carrier or composition (e.g., encapsulated in a lipid nanoparticle vehicle).

In some embodiments, the present invention is directed to stable or nuclease resistant polynucleotides (e.g., mRNA) and methods of their preparation. Such polynucleotides (e.g., recombinantly-prepared mRNA) may be prepared by hybridizing one or more complementary (e.g., perfectly complementary) stabilizing oligonucleotides to the coding and/or non-coding regions of the polynucleotide. The polynucleotides disclosed herein may encode a functional polypeptide, protein or enzyme. For example, the polynucleotide (e.g., mRNA) may encode a protein or enzyme selected from the group consisting of erythropoietin, human growth hormone, cystic fibrosis transmembrane conductance regulator (CFTR), alpha-galactosidase A, alpha-L-iduronidase, iduronate-2-sulfatase, N-acetylglucosamine-1-phosphate transferase, N-acetylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, hyaluronidase, galactocerebrosidase, ornithine transcarbamylase (OTC), carbamoyl-phosphate synthetase 1 (CPS1), argininosuccinate synthetase (ASS1), argininosuccinate lyase (ASL), and arginase 1 (ARG1).

Also disclosed herein are methods of treating one or more diseases or conditions associated with a protein or enzyme deficiency or the aberrant expression of one or more nucleic acids. Such methods comprise a step of administering a composition (e.g., a liposomal vehicle) comprising one or more of the nuclease resistant polynucleotides (e.g., mRNA) of the present invention to a subject affected by such disease or condition. Following the administration of such compositions to a subject, one or more targeted host cells are transfected and the contents of such composition delivered intracellularly where it may be translated and the expression product (e.g., a polypeptide, protein or enzyme) produced. In certain instances, the expression product (e.g., a translated protein or enzyme) may be excreted extracellularly by the one or more targeted host cells (e.g., hepatocytes).

Also disclosed herein are stabilized or nuclease resistant polynucleotides (e.g., mRNA) that comprise a complementary stabilizing oligonucleotide hybridized to the coding and/or non-coding regions of such polynucleotide. In certain embodiments, the stabilizing oligonucleotide and/or the polynucleotide (e.g., mRNA) comprise at least one modification. The modification of one or both of the polynucleotide (e.g., mRNA) and/or the stabilizing oligonucleotide to incorporate one or more modifications may be used as a means of further modulating (e.g., enhancing or increasing) the nuclease resistance of the polynucleotide. Without wishing to be bound by a particular theory, it is believed that the incorporation of modifications (e.g., 2'-O-alkyl sugar modifications) to either the stabilizing oligonucleotide and/or the polynucleotide act to sterically block or delay nuclease degradation of the polynucleotide and thereby improve stability. Accordingly, in certain embodiments, the polynucleotide and/or the stabilizing oligonucleotide (e.g., a poly-U oligonucleotide) comprise at least one (e.g., two, three, four, five, six, seven, eight, nine, ten, eleven, twelve, thirteen, fourteen, fifteen or more) modified nucleobase.

Contemplated modifications may include, for example, sugar modifications or substitutions (e.g., one or more of a 2'-O-alkyl modification, a locked polynucleotide (LNA) or a peptide polynucleotide (PNA).) In embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In certain embodiments where the modification is a nucleobase modification, such modification may be selected from the group consisting of a 5-methyl cytidine, pseudouridine, 2-thio uridine, 5-methylcytosine, isocytosine, pseudoisocytosine, 5-bromouracil, 5-propynyluracil, 6-aminopurine, 2-aminopurine, inosine, diaminopurine and 2-chloro-6-aminopurine cytosine, and combinations thereof.

In certain embodiments, the contemplated modification may involve the inter-nucleosidic bonds that comprise the stabilizing oligonucleotide and/or the polynucleotides. For example, contemplated modifications introduced to one or both of the stabilizing oligonucleotide and/or the polynucleotide may include one or more phosphorothioate bonds. In one embodiment, all of the inter-nucleosidic bonds of one or both of the stabilizing oligonucleotide and the polynucleotide are phosphorothioate bonds.

The nuclease resistance of the polynucleotides disclosed herein may be characterized relative to the native or unmodified counterpart polynucleotides (e.g., relative to an un-hybridized polynucleotide that has not been contacted or treated with a stabilizing oligonucleotide). For example, the nuclease resistant polynucleotides disclosed herein may be at least about two, three, four, five, six, seven, eight, nine, ten, twelve, fifteen, twenty, twenty-five, thirty, fifty, one hundred times more stable in vivo relative to their native or un-hybridized counterparts. In certain embodiments, the circulatory half-life (t½) of the polynucleotide in vivo is indicative of such polynucleotide's stability. In other embodiments, the relative amount of expression product (e.g., a polypeptide, protein or enzyme) expressed (e.g., translated) from the polynucleotide is indicative of its stability.

In some embodiments, the present invention relates to methods of increasing the quantity of an expression product (e.g., a functional protein or enzyme) that is or may be expressed (e.g., translated) from a polynucleotide transcript. For example, such methods may generally comprise a step of contacting a portion of the coding and/or non-coding regions of an mRNA polynucleotide transcript with a stabilizing oligonucleotide such that the stabilizing oligonucleotide hybridizes to the mRNA transcript. In certain embodiments, the stabilizing oligonucleotide and the mRNA polynucleotide transcript, are contacted at about a 0.1:1 ratio. In other embodiments, the stabilizing oligonucleotide and the mRNA polynucleotide transcript are contacted at about a 0.25:1 ratio. In yet other embodiments, the stabilizing oligonucleotide and the mRNA polynucleotide transcript are contacted at about a 0.5:1 ratio. In still other embodiments, the stabilizing oligonucleotide and mRNA polynucleotide transcript are contacted at about a 1:1 ratio. In certain embodiments, the stabilizing oligonucleotide and the mRNA polynucleotide transcript are contacted at about a 2:1, 5:1, a 10:1, a 100:1 or a 1,000:1 ratio.

Upon contacting the mRNA polynucleotide transcript with a complementary stabilizing oligonucleotide, the stabilizing oligonucleotide will hybridize to the mRNA polynucleotide (e.g., at a region of complementarity). Upon hybridizing to the mRNA, the stabilizing oligonucleotide will form a duplexed region with, for example, the non-coding region of the mRNA polynucleotide and thereby render the mRNA polynucleotide more resistant to nuclease degradation. As a result of being rendered more resistant to nuclease (e.g., endonuclease) degradation, the amount of the expression product (e.g., a polypeptide) translated from the mRNA polynucleotide transcript may be increased (e.g., increased by at least about 2.5%, 5%, 7.5%, 10%, 15%, 20%, 25%, 30%, 33%, 36%, 40%, 50%, 60%, 70%, 75%, 80%, 90%, 95%, 99%, 100%, 110%, 120%, 125%, 150%, 175%, 200%, 250%, 300%, 400%, 500%, 600%, 700%, 750%, 800%, 900%, 1,000% or more). In certain embodiments, one or both of the mRNA transcript or the stabilizing oligonucleotide may comprise at least one modification (e.g., one or more chemically modified nucleobases or modified inter-nucleotide bonds).

Also provided herein are methods of increasing the translational efficiency of an exogenous mRNA transcript. Such methods may facilitate, for example, an increase in the production of an expression product produced following translation of the mRNA polynucleotides or transcripts of the present inventions. Generally, such methods comprise a step of contacting the mRNA polynucleotide transcript with a stabilizing oligonucleotide that is complementary to the coding and/or non-coding region of the mRNA transcript under suitable conditions (e.g., high stringency conditions), thereby causing the mRNA polynucleotide transcript and the stabilizing oligonucleotide to hybridize to each other. Such methods may be employed to render the mRNA transcript more resistant to nuclease (e.g., exonuclease) degradation while modulating (e.g., increasing) the translational efficiency of the exogenous mRNA transcript by one or more target cells. In certain embodiments, the stabilizing oligonucleotide comprises at least one modified nucleobase. In certain embodiments, the mRNA transcript also comprises one or more modifications (e.g., one or more chemical modifications and/or phosphorothioate inter-nucleosidic bonds).

The above discussed and many other features and attendant advantages of the present invention will become better understood by reference to the following detailed description of the invention when taken in conjunction with the accompanying examples. The various embodiments described herein are complimentary and can be combined or used together in a manner understood by the skilled person in view of the teachings contained herein.

BRIEF DESCRIPTION OF THE DRAWINGS

As illustrated in FIG. 2 relative to the untreated EPO mRNA polynucleotide (designated "Unhybridized"), the stabilized EPO polynucleotide mRNA transcripts generally demonstrated an increase in the amount of EPO protein expressed by the 293T cells that were transfected with the stabilized mRNA transcript, and in certain instances an approximately 160% increase in the amount of EPO protein translated and produced was observed relative to the Unhybridized control.

As illustrated in FIG. 3, the stabilized EPO polynucleotide transcripts generally yielded higher cumulative amounts of EPO protein translated and produced by the 293T cells transfected with the stabilized mRNA transcripts disclosed herein.

As illustrated in FIG. 4, relative to the untreated EPO mRNA polynucleotide (designated "Unhybridized"), the stabilized or nuclease resistant polynucleotide mRNA transcripts generally demonstrated an increase in the amount of EPO protein expressed by the 293T cells transfected with such stabilized mRNA transcripts. In particular, those stabilized or nuclease resistant mRNA transcripts that were prepared by exposure of the mRNA transcript to lower concentrations of stabilizing oligonucleotide (e.g., 0.1 and 0.5) demonstrated higher translational efficiencies relative to their unmodified counterparts.

DETAILED DESCRIPTION

Figure 1:
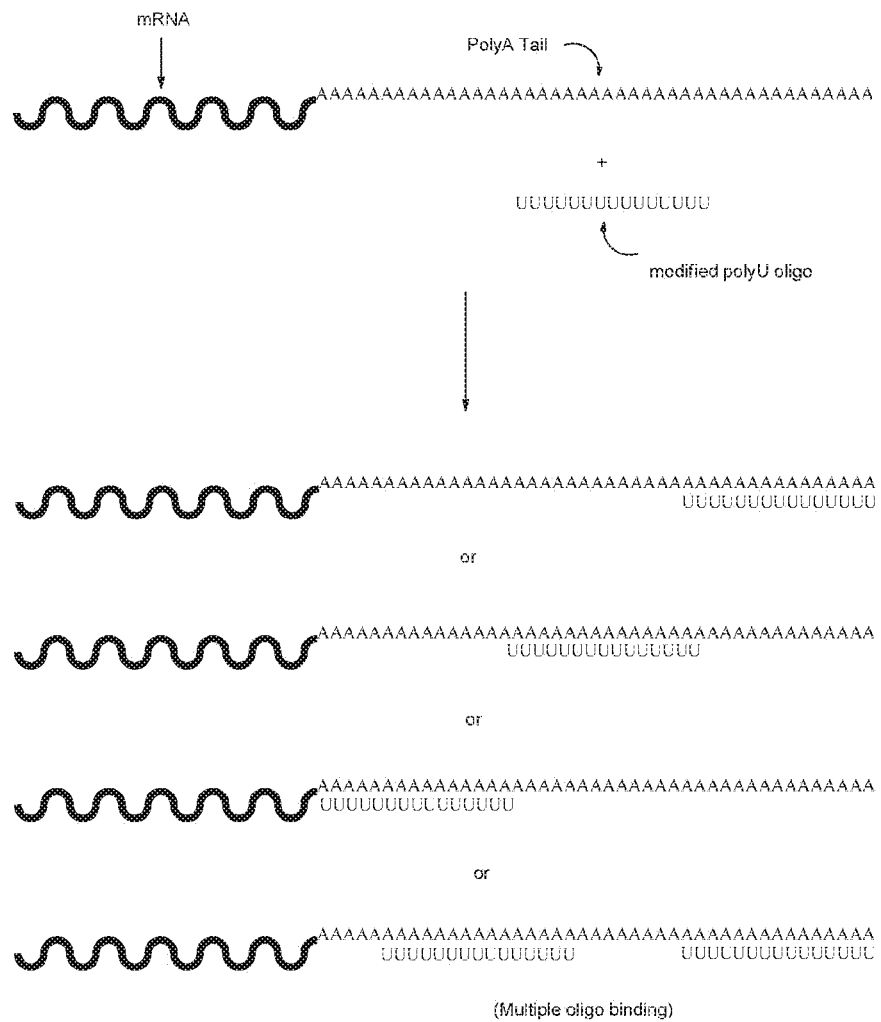
FIG. 1 illustrates one embodiment of the present invention whereby an mRNA polynucleotide transcript (as indicated by ) having a poly-A tail AAAAAAAAAAAAAAAAAAAAAAAAAAAAAAAAAAAAAAAAAA (SEQ ID NO: 6) located downstream (3') of the coding region is contacted with a 15-mer poly (2'O-Me-uracil) stabilizing oligonucleotide having a phosphorothioate backbone UUUUUUUUUUUUUUU (SEQ ID NO: 7). As illustrated, upon contacting the poly-A tail of the mRNA polynucleotide with the fully complementary stabilizing oligonucleotide a duplexed region is formed and thereby stabilizes the mRNA polynucleotide by rendering it more resistant to nuclease degradation. Because the stabilizing oligonucleotide is fully complementary to multiple regions of the depicted poly-A tail, there exist several possible duplexed constructions, only four of which are illustrated in the depicted embodiment.

The present inventions are directed to stabilized or nuclease resistant polynucleotides and compositions (e.g., mRNA polynucleotides) and related methods of their use and preparation. In certain embodiments the polynucleotides and compositions disclosed herein encode one or more functional expression products (e.g., polypeptides, proteins and/or enzymes) and are not subject to some of the limitations that are generally associated with conventional gene or enzyme replacement therapies. For example, in embodiments where the polynucleotide transcripts disclosed herein comprise mRNA, such polynucleotides need not integrate into a host cells' genome to exert their therapeutic effect. Similarly, in certain embodiments, the exogenous polynucleotide transcripts are translated by the host cells and accordingly are characterized by the native post-translational modifications that are present in the native expression product.

While the administration of exogenous polynucleotides (e.g., DNA or RNA) represents a meaningful advancement in the treatment diseases, the administration of such exogenous polynucleotides is often hampered by the limited stability of such polynucleotides, particularly following their in vivo administration. For example, following their administration to a subject, many polynucleotides may be subject to nuclease (e.g., exonuclease and/or endonuclease) degradation. Nuclease degradation may negatively influence the capability of an mRNA polynucleotide transcript to reach a target cell or to be translated, the result of which is to preclude the exogenous polynucleotide from exerting an intended therapeutic effect.

Nucleases represent a class of enzymes that are responsible for the cleavage or hydrolysis of the phosphodiester bonds that hold the nucleotides of DNA or RNA together. Those nuclease enzymes that cleave or hydrolyze the phosphodiester bonds of DNA are called deoxyribonucleases, while the nuclease enzymes that cleave the phosphodiester bonds of RNA are called ribonucleases. As generally used herein, the term "nuclease" refers to an enzyme with the capability to degrade or otherwise digest polynucleotides or nucleic acid molecules (e.g., DNA or RNA). Representative examples of nucleases include ribonucleases (RNase) which digests RNA, and deoxyribonuclease (DNase) which digests DNA. Unless otherwise specified, the term, "nuclease" generally encompasses nuclease enzymes that are capable of degrading single-stranded polynucleotides (e.g., mRNA) and/or double stranded polynucleotides (e.g., DNA).

In certain aspects, the present invention is directed to methods and strategies for stabilizing polynucleotides from nuclease degradation or for improving the resistance of one or more polynucleotides (e.g., mRNA) to nuclease degradation. It should be noted that in certain embodiments, improvements in the stability and/or nuclease resistance of the polynucleotides disclosed herein may be made with reference to a native or unmodified polynucleotide. For example, in certain embodiments, the stability and/or nuclease resistance of a polynucleotide (e.g., an mRNA transcript) is increased by at least about 105%, 110%, 115%, 120%, 125%, 130%, 135%, 140%, 150%, 160%, 170%, 175%, 180%, 190%, 200%, 250%, 300%, 350%, 400%, 450%, 500%, 600%, 700%, 800%, 900%, 1,000%, or more relative to the native or unmodified polynucleotide transcript.

As used herein to characterize a polynucleotide (e.g., an mRNA transcript encoding a functional urea cycle enzyme), the term "stable" generally refers to a reduced susceptibility to degradation or destruction (e.g., a reduced susceptibility to nuclease cleavage in vivo). For example, the term "stable" may be used to refer to a reduction in the rate of nuclease degradation of a polynucleotide in vivo. In certain embodiments, the half-life (t½) of a polynucleotide represents an objective measurement of its stability. Similarly, in certain embodiments, the amount or mass of an expression product that is produced following the expression (e.g., translation) of a stable or nuclease resistant polynucleotide represents an objective measurement of its stability. Preferred are modifications made or otherwise introduced into a polynucleotide that serve to enhance (e.g., increase) the half-life or translational efficiency of such polynucleotide in vivo relative to its unmodified counterpart. For example, in certain embodiments, the t½ of a nuclease resistant polynucleotide (e.g., an mRNA transcript) is increased by at least about 105%, 110%, 115%, 120%, 125%, 130%, 135%, 140%, 150%, 160%, 170%, 175%, 180%, 190%, 200%, 250%, 300%, 350%, 400%, 450%, 500%, 600%, 700%, 800%, 900%, 1,000%, or more relative to its native or unmodified polynucleotide counterpart. In certain embodiments, the stability of hybridized mRNA may be in part due to the inherent single strand specificity of some nuclease enzymes, and in particular RNase enzymes.

The methods disclosed herein generally comprise a step of contacting the non-coding region of the polynucleotide (e.g., the poly-A tail of an mRNA polynucleotide) with a complementary (e.g., a perfectly complementary) stabilizing oligonucleotide under suitable conditions, thereby causing the stabilizing oligonucleotide to hybridize to the non-coding region of the polynucleotide. As used herein, the terms "contact" and "contacting" generally refer to bringing two or more moieties together or within close proximity of one another such that the moieties may react. For example, in certain embodiments of the present invention, a polynucleotide (e.g., an mRNA transcript) may be contacted with one or more stabilizing oligonucleotides (e.g., a stabilizing oligonucleotide that is perfectly complementary to a region or fragment of the polynucleotide) such that the polynucleotide and stabilizing oligonucleotide would be expected to react (e.g., hybridize to one another) under suitable conditions.

Upon hybridizing of the stabilizing oligonucleotide (e.g., a 15-mer poly(2'-O-Me-uracil) oligonucleotide) to the polynucleotide, the polynucleotide is rendered more resistant to nuclease degradation. For example, in certain embodiments, provided herein are methods of increasing the nuclease resistance of an mRNA polynucleotide comprising a poly-A tail by contacting the poly-A tail of such polynucleotide with a complementary poly-U stabilizing oligonucleotide. Upon hybridizing to the non-coding region of the polynucleotide (e.g., the poly-A tail) to form a duplexed or double-stranded region, nuclease degradation of the polynucleotide may be reduced, delayed or otherwise prevented. Without wishing to be bound by any particular theories, it is believed that the observed stability and nuclease resistance of the polynucleotides disclosed herein is due in part to the single-stranded specificity of some nuclease enzymes (e.g., ribonucleases). In those embodiments where one or both of the stabilizing oligonucleotide and/or the polynucleotide comprise a modification (e.g., a chemically-modified nucleobases and/or a phosphorothioate backbone) such modifications may serve to further stabilize the polynucleotide by sterically interfering with nuclease degradation.

It should be noted that while the terms "polynucleotide" and "oligonucleotide" may be generally understood by those of ordinary skill in the art to generally be synonymous with each other, such terms are used herein for convenience to distinguish the targeted sense nucleic acid transcripts (e.g., mRNA) from the shorter (e.g., about 15-50 mer) complementary or anti-sense nucleic acids that are used to modulate the stability of a targeted sense nucleic acid transcript in accordance with the teachings of the present inventions. In particular, the phrase "stabilizing oligonucleotide" is used herein to describe a nucleic acid sequence that is generally complementary' or anti-sense to a region or fragment of a polynucleotide sequence encoding a functional expression product. While such stabilizing oligonucleotides may generally be of any length, in certain embodiments the stabilizing oligonucleotides are less than 500 nucleotides, less than 400 nucleotides, less than 300 nucleotides, less than 250 nucleotides, less than 200 nucleotides, less than 100 nucleotides, or more preferably less than 50 nucleotides, less than 40 nucleotides, less than 30 nucleotides, less than 25 nucleotides, less than 20 nucleotides, less than 19 nucleotides, less than 18 nucleotides, less than 17 nucleotides, less than 16 nucleotides or less than 15 nucleotides in length.

In certain embodiments, the stabilizing oligonucleotides (e.g., a 15-mer poly-U stabilizing oligonucleotide) disclosed herein comprise one or more modifications (e.g., modifications such as 2'-O-alkyl sugar substitutions). For example, in some embodiments the stabilizing oligonucleotide comprises one or more chemical modifications, such as one or more 2'-O-alkyl modified or substituted nucleobases or the inclusion of one or more phosphorothioate inter-nucleobase linkages. Such modifications may further improve the ability of the stabilizing oligonucleotide to hybridize to a complementary polynucleotide or may improve the stability or nuclease resistance of such polynucleotide (e.g., by interfering with recognition of such polynucleotide by nuclease enzymes).

The present inventors have surprisingly discovered that stabilized mRNA polynucleotides that were prepared by exposure of the mRNA polynucleotides to higher concentrations of stabilizing oligonucleotides resulted in the production of lower quantities of the encoded expression product (e.g., erythropoietin protein) by cells transfected with such polynucleotides. Without wishing to be bound by a particular theory, it is suspected that higher degrees of hybridization of the stabilizing oligonucleotides to the polynucleotide may interfere with the ability of the resulting duplexed (i.e., hybridized or stabilized) polynucleotide to form secondary or even tertiary structures (e.g., hairpin loops, bulges, and internal loops) that may also contribute to the stability of such polynucleotide. For example, while higher degrees of hybridization of the poly-A tail region of an mRNA polynucleotide transcript may improve the nuclease resistance of such mRNA transcript, the longer duplexed regions may also interfere with the ability of the duplexed mRNA transcript to properly fold. In certain instances where the proper folding of such mRNA transcript contributes to its stability (e.g., nuclease resistance), it is expected that interference with the ability of such transcript to properly fold may be associated with a corresponding reduction in its stability. Accordingly, in certain embodiments, shorter stabilizing oligonucleotides (e.g., about 75, 70, 60, 65, 50, 45, 40, 35, 30, 25, 24, 23, 22, 21, 20, 19, 18, 17, 16, 15, 14, 13, 12, 11, 10, 9, 8, 7, 6, 5 nucleotides or less) are preferred. Similarly, in certain embodiments the hybridization of a stabilizing oligonucleotide to a polynucleotide does not materially interfere with the ability of the resulting nuclease resistant polynucleotide to form secondary or tertiary structures.

The degree to which the nuclease resistant polynucleotides disclosed herein hybridize may be a direct function of the manner in which such nuclease resistant polynucleotides were prepared. As depicted in FIG. 1, to the extent that an mRNA polynucleotide is contacted with a high concentration of a complementary stabilizing oligonucleotide, the stabilizing oligonucleotide may hybridize to the mRNA polynucleotide at multiple regions. In certain embodiments, the extent to which a polynucleotide hybridizes with a complementary stabilizing oligonucleotide may be manipulated or otherwise controlled by modifying the relative concentrations of stabilizing oligonucleotide to which the polynucleotide is exposed. For example, in certain preferred embodiments, the stabilizing oligonucleotide and the mRNA polynucleotide transcript are contacted at about a 0.1:1 ratio. In other embodiments, the stabilizing oligonucleotide and the mRNA polynucleotide transcript are contacted at about a 0.25:1 ratio. In yet other embodiments, the stabilizing oligonucleotide and the mRNA polynucleotide transcript are contacted at about a 0.5:1 ratio. In still other embodiments, the stabilizing oligonucleotide and mRNA polynucleotide transcript are contacted at about a 1:1 ratio. In certain embodiments, the stabilizing oligonucleotide and the mRNA polynucleotide transcript are contacted at about a 5:1, a 10:1, a 100:1 or a 1,000:1 ratio.

As used herein, the term "polynucleotide" is generally used to refer to a nucleic acid (e.g., DNA or RNA) to be stabilized or rendered more nuclease resistant in accordance with the teachings of the present invention. In certain embodiments, the polynucleotides disclosed herein (or particular regions or fragments thereof) represent the nucleic acid target to which the stabilizing oligonucleotides may hybridize. The polynucleotides (e.g., an mRNA polynucleotide) disclosed herein may also comprise one or more modifications. For example, in some embodiments the mRNA polynucleotide transcripts disclosed herein comprise one or more chemical modifications, which in certain instances may further improve the stability or nuclease resistance of such polynucleotide transcript (e.g., by sterically hindering or otherwise interfering with nuclease degradation).

The polynucleotides may comprise both coding and non-coding regions and in certain embodiments described herein, the stabilizing oligonucleotides hybridize to the non-coding region of the polynucleotide. As used herein, the phrase "non-coding region" generally refers to that portion or region of the polynucleotide or a gene that is not a coding region and that is not expressed, transcribed, translated or otherwise processed into an expression product such as an amino acid, polypeptide, protein or enzyme. In the context of DNA polynucleotides, the non-coding region may comprise intron sequences or other sequences located 5' or 3' (e.g., upstream or downstream) of the coding region (e.g., promoters, enhancers, silencers). In the context of RNA polynucleotides, the non-coding region may comprise sequences located 5' or 3' (e.g., upstream or downstream) of the coding region (e.g., 3' untranslated region (UTR), a 5' untranslated region (UTR), a poly-A tail and a terminal cap). In certain embodiments, the targeted non-coding region may comprise two distinct, but overlapping regions. For example, as briefly depicted below a stabilizing oligonucleotide may be prepared such that it is perfectly complementary to a region of a polynucleotide comprising or spanning a fragment of the 3' untranslated region (UTR) and a fragment of the poly-A tail.

```
mRNA Polynucleotide Fragment: 5'- . . . . AUGGCACAUCCUGUAAAAAAAAAAAAAAAAAAAAA . . . -3'
                                              |||||||||||||||||||
Stabilizing Oligonucleotide:   3'-            CAUUUUUUUUUUUUUUU                    -5'
``` mRNA polynucleotide Fragment: SEQ ID NO: 4; Stabilizing Oligonucleotide: SEQ ID NO: 5

Similarly, a stabilizing oligonucleotide may be prepared such that it is complementary to a region of a polynucleotide comprising or spanning a fragment of a 5' cap structure and a fragment of the 5' UTR. For example, the stabilizing oligonucleotide may be complementary (e.g., at least about 50%, 55%, 60%, 65%, 70%, 75%, 80%, 85%, 87.5%, 90%, 92.5%, 95%, 97%, 98%, 99% or 100% complementary) to one or more non-coding regions of the polynucleotide selected from the group of regions consisting of the 5' UTR, a 5' terminal cap, the 3' UTR and the poly-A tail. In certain embodiments, the hybridization of a complementary stabilizing oligonucleotide to the non-coding region of an mRNA polynucleotide is preferred, in part, due to concerns relating to the ability of the resultant duplexed region (i.e., the hybridized polynucleotide and stabilizing oligonucleotide) to interfere with the translation of the coding region.

As used herein, the phrase "coding region" generally refers to that portion or region of the polynucleotide or a gene that when expressed, transcribed, translated or otherwise processed results in the production of an expression product, such as an amino acid, polypeptide, protein or enzyme. It should be understood that while certain embodiments disclosed herein contemplate the hybridization of complementary stabilizing oligonucleotides to the non-coding region of a polynucleotide transcript, the present invention need not be limited to such embodiments. Rather, the present invention also contemplates the hybridization of the complementary stabilizing oligonucleotides to regions of the polynucleotide transcript (e.g., mRNA) comprising or spanning both the coding and non-coding regions. For example, a stabilizing oligonucleotide may be prepared such that it targets and/or is complementary (e.g., perfectly complementary) to a fragment of the coding region of an mRNA polynucleotide transcript and a fragment of the non-coding 3' UTR located downstream of the coding region. The foregoing therefore provides a means of specifically targeting a particular region of the polynucleotide, such as the region located immediately downstream of the coding region. Additionally, the foregoing also provides means of controlling or otherwise affecting the degree to which a stabilizing oligonucleotide hybridizes to a complementary region of the polynucleotide. In certain embodiments where the stabilizing oligonucleotide targets the coding region (or a fragment thereof) preferably the hybridization of the stabilizing oligonucleotide to such coding region (or fragment thereof) does not interfere with the expression (e.g., transcription or translation) of such polynucleotide. Similarly, in embodiments where the stabilizing oligonucleotide targets the coding region (or a fragment thereof) preferably the hybridization of the stabilizing oligonucleotide to such coding region (or fragment thereof) does not substantially interfere with the expression (e.g., transcription or translation) of such polynucleotide.

In the context of the present invention the term "expression" is used in its broadest sense to refer to either the transcription of a specific polynucleotide (e.g., a gene or nucleic acid) into an RNA transcript, or the translation of at least one mRNA polynucleotide into a polypeptide, protein or enzyme. For example, disclosed herein are compositions which comprise one or more mRNA polynucleotides that encode functional expression products (e.g., proteins or enzymes), and in the context of such mRNA polynucleotides, the term expression refers to the translation of such mRNA polynucleotides to produce a polypeptide, protein or enzyme encoded thereby. Similarly, the phrase "expression product" is used herein in its broadest sense to generally refer to an RNA transcription product that is transcribed from a DNA polynucleotide, or alternatively to a polypeptide, protein or enzyme that is the natural translation product of an mRNA polynucleotide. In certain embodiments, the expression product of the polynucleotide is a functional enzyme (e.g., a urea cycle enzyme). In certain embodiments, the expression product of the polynucleotide is a functional protein (e.g., hormone) or enzyme. In those instances where the polynucleotide is DNA, following expression (i.e., transcription) of such DNA the encoded expression product (i.e., RNA) may be produced. Similarly, in those embodiments where the polynucleotide is mRNA, following expression (i.e., translation) of such mRNA the encoded expression product (e.g., a polypeptide, protein or enzyme) may be produced and/or excreted.

In some embodiments, the present inventions are directed to methods of modulating (e.g., increasing, improving or otherwise enhancing) the translational efficiency of one or more mRNA polynucleotides in a target cell. As used herein, the phrase "translational efficiency" refers to the rate at which an mRNA polynucleotide is translated and the corresponding expression product produced. In certain instances, the stable or nuclease resistant mRNA polynucleotides disclosed herein may be characterized by their increased translational efficiency, resulting in a corresponding increase in the production of the expression product encoded by such mRNA polynucleotide. Such methods generally comprise an initial step of contacting an mRNA polynucleotide with a complementary (e.g., perfectly or partially complementary) stabilizing oligonucleotide under suitable conditions (e.g., high stringency conditions), thereby causing the mRNA polynucleotide and one or more stabilizing oligonucleotides to hybridize to each other. As a result, the mRNA polynucleotide is rendered more resistant to nuclease degradation and the translational efficiency of such polynucleotide in one or more target cells increased. In certain embodiments, one or both of the stabilizing oligonucleotide and/or the mRNA polynucleotide may comprise at least one modified nucleobase (e.g., a 2'-O-alkyl sugar substitution). In certain embodiments, one or both of the stabilizing oligonucleotide and the mRNA polynucleotide also comprise one or more modifications (e.g., one or more nucleobases linked by phosphorothioate bonds).

In certain instances, the nuclease resistant polynucleotides disclosed herein may be recombinantly-prepared (e.g., a recombinantly-prepared codon-optimized mRNA polynucleotide). In such embodiments, such polynucleotides (e.g., a recombinantly-prepared mRNA polynucleotide) may be contacted with a complementary stabilizing oligonucleotide prior to being administered to a subject in a suitable carrier or vehicle (e.g., a lipid nanoparticle).

Also contemplated by the present invention is the direct administration of an exogenous stabilizing oligonucleotide to a subject (e.g., for the treatment of a disease or condition associated with the suboptimal or sub-therapeutic production of an expression product, such as a protein or enzyme). In such embodiments, the present inventions provide a means of modulating (e.g., increasing or otherwise enhancing) the expression, production and/or secretion of an endogenous expression product. For example, the present inventions contemplate the administration of a stabilizing oligonucleotide to a subject, wherein the stabilizing oligonucleotide is complementary (e.g., perfectly- or partially-complementary) to an endogenous polynucleotide (e.g., mRNA). In such embodiments, an exogenously-prepared stabilizing oligonucleotide that is complementary (e.g., perfectly complementary) to a region of an endogenous polynucleotide (e.g., the non-coding region of an endogenous mRNA polynucleotide) is administered to a subject. Following the administration of the exogenous stabilizing oligonucleotide, such oligonucleotide hybridizes to the one or more endogenous polynucleotides (e.g., mRNA) encoding an under-expressed expression product such that the stability or the nuclease resistance of the endogenous polynucleotide is modulated (e.g., enhanced or otherwise increased) and/or its translational efficiency increased. The resulting stabilized or nuclease resistant endogenous polynucleotide (e.g., mRNA) may be characterized as having an increase circulatory half-life ($t\frac{1}{2}$) relative to its native counterpart and, in certain instances an improved translational efficiency. As a result, the amount of the expression product (e.g., a lysosomal enzyme) encoded by such endogenous polynucleotides may be enhanced or otherwise increased and an underlying condition (e.g., a protein or enzyme deficiency) or its symptoms thereby treated or mitigated. The foregoing therefore provides a means of increasing the expression of sub-optimally expressed endogenous mRNA polynucleotides by rendering such polynucleotides more nuclease resistant relative to their native (and under-expressed) counterparts. It should be understood that while the foregoing embodiments (i.e., the direct administration of stabilizing oligonucleotides to a subject) may generally relate to traditional anti-sense or RNAi mechanisms of targeting endogenous nucleic acids (e.g., mRNA), the observed effect of such targeting is an increase, rather than a decrease, in the production of the expression product encoded by the targeted polynucleotide. In certain embodiments, the stabilizing oligonucleotide is delivered or administered to a subject in a suitable pharmaceutical carrier, vehicle or composition (e.g., encapsulated in a lipid nanoparticle vehicle).

The polynucleotides provided herein, and in particular the mRNA polynucleotides provided herein, preferably retain at least some ability to be expressed or translated, to thereby produce a functional expression product (e.g., a protein or enzyme) within a target cell. Accordingly, the present invention also relates to the administration of stabilized or duplexed polynucleotides to a subject (e.g., mRNA which has been stabilized against in vivo nuclease digestion or degradation). In a preferred embodiment of the present invention, the therapeutic activity of the nuclease resistant polynucleotide is prolonged or otherwise evident over an extended period of time (e.g., at least about twelve hours, twenty-four hours, thirty-six hours, seventy-two hours, four days, five days, 1 week, ten days, two weeks, three weeks, four weeks, six weeks, eight weeks, ten weeks, twelve weeks or longer). For example, the therapeutic activity of the nuclease resistant polynucleotides may be prolonged such that the compositions of the present invention are administered to a subject on a semi-weekly or bi-weekly basis, or more preferably on a monthly, bi-monthly, quarterly or even on an annual basis. The extended or prolonged activity of the compositions of the present invention, and in particular of the nuclease resistant mRNA polynucleotides comprised therein, is directly related to the translational efficiency of such polynucleotide and the quantity of the expression product (e.g., a functional protein or enzyme) that can be translated from such mRNA.

In certain embodiments the translational efficiency and the in vivo activity of the nuclease resistant polynucleotides and compositions of the present invention may be further extended or prolonged by the introduction of one or more modifications to such polynucleotides to improve or enhance their half-life (t½). For example, the Kozac consensus sequence plays a role in the initiation of protein translation, and the inclusion of such a Kozac consensus sequence in the mRNA polynucleotides of the present invention may further extend or prolong the activity or translational efficiency of such mRNA polynucleotides. Furthermore, the quantity of functional protein or enzyme translated by the target cell is a function of the quantity of polynucleotide (e.g., mRNA) delivered to the target cells and the stability of such polynucleotide. To the extent that the stability and/or half-life of the nuclease resistant polynucleotides of the present invention may be improved or enhanced, the therapeutic activity of the translated protein or enzyme and/or the dosing frequency of the composition may be further extended.

Accordingly, in a preferred embodiment, one or both of the polynucleotides and/or the stabilizing oligonucleotides disclosed herein comprise at least one modification. As used herein, the terms "modification" and "modified" as they relate to the polynucleotides and/or stabilizing oligonucleotides provided herein, refer to at least one alteration or chemical modification introduced into such polynucleotides and/or stabilizing oligonucleotides and which preferably renders them more stable (e.g., resistant to nuclease digestion) than the wild-type or naturally occurring version of the polynucleotide. For example, the introduction of chemical modifications into one or more of the polynucleotide and the stabilizing oligonucleotide may interfere with, sterically hinder or otherwise delay their recognition and/or degradation by one or more nuclease enzymes (e.g., RNase). Increased stability can include, for example, less sensitivity to hydrolysis or other destruction by endogenous enzymes (e.g., endonucleases or exonucleases) or conditions within the target cell or tissue, thereby increasing or enhancing the circulatory half-life or residence time of such polynucleotides in the target cell, tissue, subject and/or cytoplasm. The stabilized or nuclease resistant polynucleotides provided herein may demonstrate longer half-lives relative to their naturally occurring or un-hybridized counterparts (e.g. the wild-type version of the polynucleotide). Also contemplated by the terms "modification" and "modified", as such terms relate to mRNA polynucleotides and/or stabilizing oligonucleotides of the present invention, are alterations which improve or enhance the translational efficiency of such mRNA polynucleotides, including for example, the inclusion of sequences which affect the initiation of protein translation (e.g., the Kozac consensus sequence). (See, Kozak, M L, Nucleic Acids Res. (1987); 15 (20): 8125-48).

Exemplary modifications to a polynucleotide may also include the depletion of a base (e.g., by deletion or by the substitution of one nucleotide for another) or modification of a base, for example, the chemical modification of a base. The phrase "chemical modifications" as used herein, includes modifications which introduce chemistries that differ from those observed in naturally occurring polynucleotides, for example, covalent modifications such as the introduction of modified bases (e.g., nucleotide analogs, or the inclusion of pendant groups "which are not naturally found in such polynucleotides). In certain embodiments, exemplary chemical modifications that may be introduced into one or both of the polynucleotide and the stabilizing oligonucleotide include pseudouridine, 2-thiouracil, 5-methyl cytidine, 5-methylcytosine, isocytosine, pseudoisocytosine, 5-bromouracil, 5-propynyluracil, 6-aminopurine, 2-aminopurine, inosine, diaminopurine and 2-chloro-6-aminopurine cytosine.

In addition, suitable modifications may include alterations in one or more nucleotides of a codon such that the codon encodes the same amino acid but is more stable relative to the wild-type codon of the polynucleotide found in nature. For example, an inverse relationship between the stability of RNA and a higher number cytidines (C) and/or uridines (U) residues has been demonstrated, and RNA lacking C and U residues have been found to be stable to most RNases. (Heidenreich, et al. j Biol Chem 269, 2131-8 (1994)). In some embodiments, the number of C and/or U residues in an mRNA sequence is reduced. In other embodiments, the number of C and/or U residues is reduced by substitution of one codon encoding a particular amino acid for another codon encoding the same or a related amino acid. Contemplated modifications to the mRNA polynucleotides of the present invention also include the incorporation of pseudouridines. The incorporation of pseudouridines into the mRNA polynucleotides of the present invention may enhance their stability and translational capacity, as well as diminish their immunogenicity in vivo. (See, e.g., Karikó, K., et al., Molecular Therapy 16 (11): 1833-1840 (2008)). Substitutions and modifications to the poly nucleotides of the present invention may be performed by methods readily known to one or ordinary skill in the art.

The constraints on reducing the number of C and U residues in a sequence will likely be greater within the coding region of an mRNA polynucleotide, compared to its untranslated region, (i.e., it will likely not be possible to eliminate all of the C and U residues present in the coding region while still retaining the ability of the message to encode the desired amino acid sequence). The degeneracy of the genetic code, however presents an opportunity to allow the number of C and/or U residues that are present in the sequence to be reduced, while maintaining the same coding capacity (i.e., depending on which amino acid is encoded by a codon, several different possibilities for modification of RNA sequences may be possible). For example, the codons for Gly can be altered to GGA or GGG instead of GGU or GGC.

As previously mentioned, the term modification also includes, for example, the incorporation of non-nucleotide linkages or modified nucleotides into the polynucleotides and/or stabilizing oligonucleotides of the present invention. Such modifications include the addition of bases to a polynucleotide sequence (e.g., the inclusion of a poly-A tail or the lengthening of the poly-A tail), the alteration of the 3' UTR or the 5' UTR, and the inclusion of elements which change the structure of a polynucleotide and/or stabilizing oligonucleotide (e.g., elements which modulate the ability of such polynucleotides or their expression products to form secondary structures).

In certain embodiments the poly-A tail and the region immediately upstream represent suitable regions of a polynucleotide that the stabilizing oligonucleotides (e.g., a 15-mer poly-U stabilizing oligonucleotide) disclosed herein may target and/or hybridize to. The poly-A tail is thought to naturally stabilize natural mRNA polynucleotides and synthetic sense RNA. Therefore, in certain embodiments a long poly-A tail can be added to an mRNA polynucleotide and thus render the mRNA more stable. In other embodiments, the poly-A tail or a particular region thereof may be contacted under suitable condition (e.g., high stringency conditions) with a complementary stabilizing oligonucleotide (e.g., a poly-U stabilizing oligonucleotide) and thereby render the polynucleotide more nuclease resistant. Poly-A tails can be added using a variety of art-recognized techniques. For example, long poly-A tails can be added to synthetic or in vitro transcribed RNA using poly-A polymerase. (Yokoe, et al. Nature Biotechnology. 1996; 14: 1252-1256). In addition, poly-A tails can be added by transcription directly from PCR products or may be ligated to the 3' end of an mRNA polynucleotide with RNA ligase. (See, e.g., Molecular Cloning A Laboratory Manual, 2nd Ed., ed. by Sambrook, Fritsch and Maniatis (Cold Spring Harbor Laboratory Press: 1991 edition)). In certain embodiments, the length of the poly-A tail is at least about 20, 40, 50, 75, 90, 100, 150, 200, 250, 300, 350, 400, 450 or at least 500 nucleotides. In certain embodiments, the length of the poly-A tail is adjusted to control the stability of an mRNA polynucleotide of the invention. For example, since the length of the poly-A tail can influence the half-life of an mRNA polynucleotide, the length of the poly-A tail can be adjusted to modify the level of resistance of the mRNA to nucleases and thereby control its translational efficiency in a target cell. In certain embodiments, the stabilized or nuclease resistant polynucleotides are sufficiently resistant to in vivo degradation (e.g., by nucleases), such that they may be delivered to the target cell without a carrier.

In certain embodiments, a polynucleotide can be modified by the incorporation 3' and/or 5' untranslated (UTR) sequences which are not naturally found in the wild-type polynucleotide. In certain embodiments, 3' and/or 5' flanking sequences which naturally flank an mRNA and encode a second, unrelated protein can be incorporated into the nucleotide sequence of an mRNA polynucleotide in order to further enhance its translational efficiency. For example, 3' or 5' sequences from mRNA polynucleotides which are stable (e.g., globin, actin, GAPDH, tubulin, histone, or citric acid cycle enzymes) can be incorporated into the 3' and/or 5' region of a sense mRNA polynucleotide to increase its stability. To the extent such modifications are incorporated into a polynucleotide, in certain embodiments the regions of the polynucleotide including such modifications (e.g., a 3' UTR) may also represent a suitable target to which the stabilizing oligonucleotides disclosed herein may hybridize to in an effort to further stabilize such modified polynucleotide.

The present inventions also contemplate modifications to the 5' end of the polynucleotides (e.g., mRNA) to include a partial sequence of a CMV immediate-early 1 (IE1) gene, or a fragment thereof (e.g., SEQ ID NO: 1 or SEQ ID NO: 2) to improve the nuclease resistance and/or improve the half-life of the polynucleotide. In addition to increasing the stability of the mRNA polynucleotide sequence, it has been surprisingly discovered that the inclusion of a partial sequence of a CMV immediate-early 1 (IE1) gene enhances the translation of the mRNA and the expression of the functional protein or enzyme. Also contemplated is the inclusion of a sequence encoding human growth hormone (hGH), or a fragment thereof (e.g., SEQ ID NO: 3) to one or both of the 3' and 5' ends of the polynucleotide (e.g., mRNA) to further stabilize the polynucleotide. Generally, preferred modifications improve the stability, translational efficiency, nuclease resistance and/or pharmacokinetic properties (e.g., half-life) of the polynucleotide relative to its unmodified counterpart, and include, for example modifications made to improve such polynucleotide's resistance to in vivo nuclease digestion.

The administration of the compositions, stabilized polynucleotides and stabilizing oligonucleotides disclosed herein may be facilitated by formulating such compositions in a suitable carrier (e.g., a lipid nanoparticle). As used herein, the term "carrier" includes any of the standard pharmaceutical carriers, vehicles, diluents, excipients and the like which are generally intended for use in connection with the administration of biologically active agents, including polynucleotides. The compositions and in particular the carriers described herein are capable of delivering polynucleotides and/or stabilizing oligonucleotides of varying sizes to their target cells or tissues. In certain embodiments of the present invention, the carriers of the present invention are capable of delivering large polynucleotide sequences (e.g., polynucleotides of at least 1 kb, 1.5 kb, 2 kb, 2.5 kb, 5 kb, 10 kb, 12 kb, 15 kb, 20 kb, 25 kb, 30 kb, 35 kb, 40 kb, 45 kb, 50 kb, or more). The polynucleotides can be formulated with one or more acceptable reagents to facilitate the delivery of such polynucleotides to target cells. Appropriate reagents are generally selected with regards to a number of factors, which include, among other things, the biological or chemical properties of the polynucleotides (e.g., charge), the intended route of administration, the anticipated biological environment to which such polynucleotides will be exposed and the specific properties of the intended target cells. In some embodiments, carriers, such as liposomes or synthetically-prepared exosomes, encapsulate the polynucleotides. In some embodiments, the carrier demonstrates preferential and/or substantial binding to a target cell relative to non-target. cells. In a preferred embodiment, the carrier delivers its contents to the target cell such that the polynucleotides are delivered to the appropriate subcellular compartment, such as the cytoplasm.

In certain embodiments, the carriers disclosed herein comprise a liposomal vesicle, or other means to facilitate the transfer of a polynucleotide to target cells and tissues. Suitable carriers include, but are not limited to, liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), nanodendrimers, starch-based delivery systems, micelles, emulsions, niosomes, plasmids, viruses, calcium phosphate nucleotides, aptamers, peptides and other vectorial tags. Also contemplated is the use of bionanocapsules and other viral capsid proteins assemblies as a suitable carrier. (Hum. GeneTher. 2008 September; 19(9):887-95).

In a preferred embodiment of the present invention, the carrier is formulated as a lipid nanoparticle. As used herein, the phrase "lipid nanoparticle" refers to a carrier comprising one or more lipids (e.g., cationic and/or non-cationic lipids).

Preferably, the lipid nanoparticles are formulated to deliver one or more polynucleotides (e.g., mRNA) to one or more target cells or tissues. The use of lipids, either alone or as a component of the carrier, and in particular lipid nanoparticles, is preferred. Examples of suitable lipids include, for example, the phosphatidyl compounds (e.g., phosphatidylglycerol, phosphatidylcholine, phosphatidylserine, phosphatidylethanolamine, sphingolipids, cerebrosides, and gangliosides). Also contemplated is the use of polymers as carriers, whether alone or in combination with other carriers. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins and polyethylenimine. In certain embodiments, the carrier is selected based upon its ability to facilitate the transfection of a target cell with one or more polynucleotides.

In certain embodiments of the present invention, the carrier may be selected and/or prepared to optimize delivery of the polynucleotide to the target cell, tissue or organ. For example, if the target cell is a pneumocyte the properties of the carrier (e.g., size, charge and/or pH) may be optimized to effectively deliver such carrier to the target cell or organ, reduce immune clearance and/or promote retention in that target organ. Alternatively, if the target tissue is the central nervous system (e.g., to facilitate delivery of mRNA polynucleotides to targeted brain or spinal tissue) selection and preparation of the carrier must consider penetration of, and retention within the blood brain barrier and/or the use of alternate means of directly delivering such carrier to such target tissue. In certain embodiments, the compositions of the present invention may be combined with agents that facilitate the transfer of exogenous polynucleotides from the local tissues or organs into which such compositions were administered to one or more peripheral target organs or tissues.

The use of liposomal carriers to facilitate the delivery of polynucleotides to target cells is contemplated by the present invention. Liposomes (e.g., liposomal lipid nanoparticles) are generally useful in a variety of applications in research, industry, and medicine, particularly for their use as carriers of diagnostic or therapeutic compounds in vivo (Lasic, Trends Biotechnol., 16: 307-321, 1998; Drummond et al., Pharmacol. Rev., 51: 691-743, 1999) and are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.).

In the context of the present invention, a liposomal carrier typically serves to transport the polynucleotide and/or stabilizing oligonucleotide to a target cell. For the purposes of the present invention, the liposomal carriers are prepared to contain the desired polynucleotides. The process of incorporating a desired compound (e.g., a stabilized or nuclease resistant polynucleotide and/or a stabilizing oligonucleotide) into a liposome is often referred to as "loading" (basic, et al., FEES Lett., 312: 255-258, 1992). The liposome-incorporated polynucleotides may be completely or partially located in the interior space of the liposome, within the bilayer membrane of the liposome, or associated with the exterior surface of the liposome membrane. The incorporation of a polynucleotide into liposomes is also referred to herein as "encapsulation" wherein the polynucleotide is entirely contained within the interior space of the liposome.

One primary purpose of incorporating a polynucleotide into a carrier, such as a liposome, is to protect the polynucleotide from an environment which may contain enzymes (e.g., nuclease enzymes) or chemicals that degrade or otherwise negatively influence the stability of the polynucleotides encapsulated therein. Accordingly, in a preferred embodiment of the present invention, the selected carrier is capable of further enhancing the stability of the nuclease resistant polynucleotides (e.g., a nuclease resistant mRNA polynucleotide encoding a functional protein) contained therein. For example, a liposomal carrier may allow' the encapsulated polynucleotide to reach the target cell and/or may preferentially allow the encapsulated polynucleotide to reach the target cell, or alternatively limit the delivery of such polynucleotides to other sites or cells where the presence of the administered polynucleotide may be useless or undesirable. Furthermore, incorporating the polynucleotides into a carrier, such as for example, a cationic liposome, also facilitates the delivery of such polynucleotides into a target cell.

Ideally, liposomal carriers are prepared to encapsulate one or more desired polynucleotides (e.g., a nuclease resistant mRNA polynucleotide encoding a urea cycle enzyme) such that the compositions demonstrate a high transfection efficiency, enhanced stability and improved translational efficiency. While liposomes can facilitate the introduction of polynucleotides into target cells, the addition of polycations (e.g., poly L-lysine and protamine), as a copolymer can further facilitate, and in some instances markedly enhance the transfection efficiency of several types of cationic liposomes by 2-28 fold in a number of cell lines both in vitro and in vivo. (See N. J. Caplen, et al., Gene Ther. 1995; 2: 603; S. Li, et al., Gene Ther. 1997; 4, 891.)

The present invention contemplates the use of cationic lipids and liposomes to encapsulate and/or enhance the delivery of the nuclease resistant polynucleotides and/or stabilizing oligonucleotides disclosed herein into their target cells and tissues. As used herein, the phrase "cationic lipid" refers to any of a number of lipid species that carry a net positive charge at a selected pH, such as physiological pH. The contemplated liposomal carriers and lipid nanoparticles may be prepared by including multi-component lipid mixtures of varying ratios employing one or more cationic lipids, non-cationic lipids and PEG-modified lipids. Several cationic lipids have been described in the literature, many of which are commercially available. In some embodiments, the cationic lipid N-[1-(2,3-dioleyloxy)propyl]-N,N,N-trimethylammonium chloride or "DOTMA" is used. (Felgner et al. (Proc. Nat'l Acad. Sci. 84, 7413 (1987); U.S. Pat. No. 4,897,355). DOTMA can be formulated alone or can be combined with a neutral lipid, such as, e.g., dioleoylphosphatidylethanolamine or "DOPE" or other cationic or non-cationic lipids into a liposomal carrier or a lipid nanoparticle, and such liposomes can be used to enhance the delivery of polynucleotides into target cells. Particularly suitable cationic lipids for use in the compositions and methods of the invention include those described in international patent publication WO 2010/053572, incorporated herein by reference, and most particularly, C12-200 described at paragraph [00225] of WO 2010/053572. Another particularly suitable cationic lipid for use in connection with the invention is 2-(2,2-di((9Z, 12Z)-octadeca-9,12-dien-1-yl)-1,3-dioxolan-4-yl)-N,N-dimethyl-ethanamine or "DLin-KC2-DMA" (See, WO 2010/042877; Semple et al., nature Biotech. 28:172-176 (2010). Other suitable cationic lipids include, for example, 5-carboxyspermylglycinedioctadecylamide or "DOGS," 2,3-dioleyloxy-N-[2(spermine-carboxamido)ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP". Contemplated cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylammonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy) propane or "CLinDMA", 2-[5'-(cholest-5-en-3-beta-oxy)-3'-oxapentoxy)-3-dimethy 1-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-DilinoleyIcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethy 1-[1,3]-dioxolane or "DLin-K-DMA", 2,2-dilinoleyl-4-dimethylaminoethyl-[1,3]-dioxolane or "DLin-K-XTC2-DMA", or mixtures thereof. (Heyes, J., et al., J Controlled Release 107: 276-287 (2005); Morrissey, D V., et al., Nat. Biotechnol. 23(8): 1003-1007 (2005); PCT Publication WO2005/T21348A1).

The use of cholesterol-based cationic lipids is also contemplated by the present invention. Such cholesterol-based cationic lipids can be used, either alone or in combination with other cationic or non-cationic lipids. Suitable cholesterol-based cationic lipids include, for example, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335).

In addition, several reagents are commercially available to enhance transfection efficacy. Suitable examples include LIPOFECTIN (DOTMA:DOPE) (Invitrogen, Carlsbad, Calif.), LIPOFECTAMINE (DOSPA:DOPE) (Invitrogen), LIPOFECTAMINE2000. (Invitrogen), FUGENE, TRANSFECTAM (DOGS), and EFFECTENE.

Also contemplated are cationic lipids such as the dialkylamino-based, imidazole-based, and guanidinium-based lipids. For example, certain embodiments are directed to a composition comprising one or more imidazole-based cationic lipids, for example, the imidazole cholesterol ester or "ICE" lipid (3S, LOR, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl(propanoate. In a preferred embodiment, a carrier (e.g., a lipid nanoparticle) for delivery of RNA (e.g., mRNA) or protein (e.g., an enzyme), for example a therapeutic amount of RNA or protein, may comprise one or more imidazole-based cationic lipids, for example, the imidazole cholesterol ester or "ICE" lipid (3S, I0R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate. The imidazole-based cationic lipids are also characterized by their reduced toxicity relative to other cationic lipids. The imidazole-based cationic lipids (e.g., ICE) may be used as the sole cationic lipid in the carrier or lipid nanoparticle, or alternatively may be combined with traditional cationic lipids (e.g., DOPE, DC-Chol), non-cationic lipids, PEG-modified lipids and/or helper lipids. The cationic lipid may comprise a molar ratio of about 1% to about 90%, about 2% to about 70%, about 5% to about 50%, about 10% to about 40% of the total lipid present in the carrier, or preferably about 20% to about 70% of the total lipid present in the carrier.

Similarly, certain embodiments are directed to lipid nanoparticles comprising the HGT4003 cationic lipid 2-((2,3-Bis((9Z,12Z)-octadeca-9,12-dien-1-yloxy)propyl)disulfanyl)-N,N-dimethylethanamine, as further described in U.S. Provisional Application No. 61/494,882 filed Jun. 8, 2011, the entire teachings of which are incorporated herein by reference in their entirety. In other embodiments the compositions and methods described herein are directed to lipid nanoparticles comprising one or more ionizable cationic lipids, such as, for example, one or more of the cationic lipids or compounds (e.g., HGT5001, HGT5002 and HGT5003), as further described in U.S. Provisional Application No. 61/617,468, incorporated herein by reference in their entirety.

In other embodiments the compositions and methods described herein are directed to lipid nanoparticles comprising one or more cleavable lipids, such as, for example, one or more cationic lipids or compounds that comprise a cleavable disulfide (S—S) functional group (e.g., HGT4001, HGT4002, HGT4003, HGT4004 and HGT4005), as further described in U.S. Provisional Application No. 61/494,882, incorporated herein by reference in their entirety.

The use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipid formulations together which comprise the carrier (e.g., a lipid nanoparticle). Contemplated PEG-modified lipids include, but is not limited to, a polyethylene glycol chain of up to 5 kDa in length covalently attached to a lipid with alkyl chain(s) of $C_6$-$C_{20}$ length. The addition of such components may prevent complex aggregation and may also provide a means for increasing circulation lifetime and increasing the delivery of the lipid-polynucleotide composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., $C_{14}$ or $C_{18}$). The PEG-modified phospholipid and derivatized lipids of the present invention may comprise a molar ratio from about 0% to about 20%, about 0.5% to about 20%, about 1% to about 15%, about 4% to about 10%, or about 2% of the total lipid present in the liposomal carrier. In some embodiments, the PEG-modified lipid employed in the compositions and methods of the invention is 1,2-Dimyristoyl-sn-glycerol, methoxypolyethylene Glycol (2000 MW PEG) (DMG-PEG2000).

The present invention also contemplates the use of non-cationic lipids to facilitate delivery of the nuclease resistant polynucleotides or stabilizing oligonucleotides to one or more target cells, organs or tissues. As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distcaroylphosphatidylcholinc (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. Such non-cationic lipids may be used alone, but are preferably used in combination with other excipients, for example, cationic lipids. When used in combination with a cationic lipid, the non-cationic lipid may comprise a molar ratio of 5% to about 90%, or preferably about 10% to about 70% of the total lipid present in the carrier.

Preferably, the carrier (e.g., a lipid nanoparticle) is prepared by combining multiple lipid and/or polymer components. For example, a carrier may be prepared using DSPC/CHOL/DODAP/C8-PEG-5000 ceramide in a molar ratio of about 1 to 50:5 to 65:5 to 90:1 to 25, respectively. A carrier may be comprised of additional lipid combinations in various ratios, including for example, DSPC/CHOL/DODAP/mPEG-5000 (e.g., combined at a molar ratio of about 33:40:25:2), DSPC/CHOL/DODAP/C8 PEG-2000-Cer (e.g., combined at a molar ratio of about 31:40:25:4), POPC/DODAP/C8-PEG-2000-Cer (e.g., combined at a molar ratio of about 75-87:3-14:10) or DSPC/CHOL/DOTAP/C8 PEG-2000-Cer (e.g., combined at a molar ratio of about 31:40:25:4). The selection of cationic lipids, non-cationic lipids and/or PEG-modified lipids which comprise the liposomal carrier or lipid nanoparticle, as well as the relative molar ratio of such lipids to each other, is based upon the characteristics of the selected lipid(s), the nature of the intended target cells or tissues and the characteristics of the polynucleotides to be delivered by the liposomal carrier. Additional considerations include, for example, the saturation of the alkyl chain, as well as the size, charge, pH, pKa, fusogenicity and toxicity of the selected lipid(s).

The liposomal carriers for use in the present invention can be prepared by various techniques which are presently known in the art. Multi-lamellar vesicles (ME V) may be prepared by conventional techniques, for example, by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Unilamellar vesicles (ULV) can then be formed by homogenization, sonication or extrusion of the multi-lamellar vesicles. In addition, unilamellar vesicles can be formed by detergent removal techniques.

In certain embodiments of this invention, the compositions comprise a carrier wherein a nuclease resistant polynucleotide (e.g., mRNA encoding OTC) is associated on both the surface of the carrier (e.g., a liposome) and encapsulated within the same carrier. For example, during preparation of the compositions of the present invention, cationic liposomal carriers may associate with the polynucleotides (e.g., mRNA) through electrostatic interactions with such therapeutic mRNA.

In certain embodiments, the compositions or polynucleotides of the present invention may comprise or be loaded with a diagnostic radionuclide, fluorescent material or other material that is detectable in both in vitro and in vivo applications. For example, suitable diagnostic materials for use in the present invention may include Rhodamine-dioleoylphosphatidylethanolamine (Rh-PE), Green Fluorescent Protein mRNA (GFP mRNA), *Renilla* Luciferase mRNA and Firefly Luciferase mRNA.

During the preparation of liposomal carriers, water soluble carrier agents may be encapsulated in the aqueous interior by including them in the hydrating solution, and lipophilic molecules may be incorporated into the lipid bilayer by inclusion in the lipid formulation. In the case of certain molecules (e.g., cationic or anionic lipophilic polynucleotides), loading of the polynucleotide into preformed liposomes may be accomplished, for example, by the methods described in U.S. Pat. No. 4,946,683, the disclosure of which, is incorporated herein by reference. Following encapsulation of the polynucleotide, the liposomes may be processed to remove un-encapsulated mRNA through processes such as gel chromatography, diafiltration or ultrafiltration. For example, if it is desirous to remove externally bound polynucleotide from the surface of the liposomal earner formulation, such liposomes may be subject to a Diethylaminoethyl SEPHACEL column.

In addition to the encapsulated nuclease resistant polynucleotide, one or more secondary therapeutic or diagnostic agents may be included in the carrier. For example, such additional therapeutic agents may be associated with the surface of the liposome, can be incorporated into the lipid bilayer of a liposome by inclusion in the lipid formulation or loading into preformed liposomes. (See, e.g., U.S. Pat. Nos. 5,194,654 and 5,223,263, which are incorporated by reference herein).

There are several methods for reducing the size, or "sizing", of liposomal carriers, and any of these methods may generally be employed when sizing is used as part of the invention. The extrusion method is a preferred method of liposome sizing. (Hope, M J et al. Reduction of Liposome Size and Preparation of Unilamellar Vesicles by Extrusion Techniques. In: Liposome Technology (G. Gregoriadis, Ed.) Vol. 1. p 123 (1993)). The method comprises a step of extruding liposomes through a small-pore polycarbonate membrane or an asymmetric ceramic membrane to reduce liposome sizes to a relatively well-defined size distribution. Typically, the suspension is cycled through the membrane one or more times until the desired liposome size distribution is achieved. The liposomes may be extruded through successively smaller pore membranes to achieve gradual reduction in liposome size.

A variety of alternative methods known in the art are available for sizing of a population of liposomal carriers. One such sizing method is described in U.S. Pat. No. 4,737,323, the entire teachings of which are incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, Ann. Rev. Biophys. Bioeng., 10:421-450 (1981), incorporated herein by reference. Average liposome diameter may be reduced by-sonication of formed liposomes. Intermittent sonication cycles may be alternated with QELS assessment to guide efficient liposome synthesis.

Selection of the appropriate size of a carrier must take into consideration the site of the target cell or tissue and to some extent the application for which the liposome is being made. For example, to the extent that the compositions are intended for pulmonary administration (e.g., as an inhalable liquid or solid carrier), the ability of the carrier to distribute into the tissues of the lung may be influenced by the size of the carrier particles that comprise such composition. Accordingly, in certain embodiments, it may be desirable to enhance the distribution of such compositions to certain cells or tissues of the lung by appropriately sizing such compositions such that upon administration (e.g., by inhalation), such compositions distribute to one or more targeted cells and tissues.

In some embodiments, the compositions provided herein are generally administered via the pulmonary route of administration. Accordingly, in certain embodiments the carriers and/or compositions disclosed herein are prepared for pulmonary administration. For example, a pulmonary surfactant may be added as an excipient component of a carrier formulation (e.g., a lipid nanoparticle comprising one or more cationic lipids, neutral lipids and pulmonary surfactants). Alternatively, in certain embodiments, the compositions disclosed herein may comprise one or more pulmonary surfactants that may be formulated independently of the carrier. The inclusion of pulmonary surfactants (e.g., lamellar bodies) in the compositions disclosed herein may also serve to loosen, break-up or otherwise facilitate the elimination of mucous from the lungs of the subject, thereby improving the distribution of the compositions into the tissues of the lung. In certain embodiments, such lamellar bodies may also function as a carrier to facilitate the delivery or distribution of one or more polynucleotides to target cells, tissues and/or organs. For example, such lamellar body earners may also be loaded or otherwise prepared such that they also comprise one or more polynucleotides (e.g., mRNA encoding a functional protein or enzyme). In other embodiments, the compositions disclosed herein may comprise synthetically- or naturally-prepared lamellar bodies and lipid nanoparticles.

Where the compositions disclosed herein comprise lamellar bodies, such lamellar bodies may comprise one or more of phosphatidylcholine (PC), phosphatidylethanolamine (PE), phosphatidylserine (PS), phosphatidylinositol (PI), phosphatidylglycerol (PG), sphingomyelin (SM), cholesterol (CHOL) and dipalmitoylphosphatidylcholine (DPPC).

In certain embodiments, the compositions and/or carriers disclosed herein may also comprise one or more exosomes. Exosomes are small micro-vesicles that are shed from the surface membranes of most cell types (e.g., mammalian cell types) and that have been implicated as playing a pivotal role in cell-to-cell communications (e.g., as a vehicle for transferring various bioactive molecules). (See, e.g., Camussi, et al., Kidney Int. (2010); 78(9): 838-48, the contents of which are incorporated herein by reference in their entirety.)

In certain embodiments, the liver represents an important peripheral target organ for the compositions of the present invention in part due to its central role in metabolism and production of proteins and accordingly diseases which are caused by defects in liver-specific gene products (e.g., the urea cycle disorders) may benefit from specific targeting of cells (e.g., hepatocytes). Accordingly, in certain embodiments of the present invention, the structural characteristics of the target tissue may be exploited to direct the distribution of the liposomal carrier and its polynucleotide payload to such target tissues. For example, to target hepatocytes a liposomal carrier may be sized such that its dimensions are smaller than the fenestrations of the endothelial layer lining hepatic sinusoids in the liver; accordingly the liposomal carrier can readily penetrate such endothelial fenestrations to reach the target hepatocytes. Alternatively, a liposomal carrier may be sized such that the dimensions of the liposome are of a sufficient diameter to limit or expressly avoid distribution into certain cells or tissues (e.g., peripheral cells and tissues). For example, a liposomal carrier may be sized such that its dimensions are larger than the fenestrations of the endothelial layer lining hepatic sinusoids to thereby limit distribution of the liposomal carrier to hepatocytes. In such an embodiment, large liposomal carriers will not easily penetrate the endothelial fenestrations, and would instead be cleared by the macrophage Kupffer cells that line the liver sinusoids. Generally, the size of the carrier is within the range of about 25 to 250 nm, preferably less than about 250 nm, 175 nm, 150 nm, 125 nm, 100 nm, 75 nm, 50 nm, 25 nm or 10 nm.

Similarly, the compositions of the present invention may be prepared to preferentially distribute to other local and/or peripheral target tissues, cells or organs, such as the brain, cerebrospinal fluid, muscle, heart, lungs, kidneys and/or spleen. For example, the carriers of the present invention may be prepared to achieve enhanced delivery to the target cells and tissues. Accordingly, the compositions of the present invention may be enriched with additional cationic, non-cationic and PEG-modified lipids to further target tissues or cells.

In certain embodiments, one or more peripheral target cells and tissues may function as a biological reservoir or depot capable of expressing or otherwise producing and systemically excreting a functional protein or enzyme, as disclosed for example, in International Application No. PCT/US2010/058457 and in U.S. Provisional Application No. 61/494,881, the teachings of which are both incorporated herein by reference in their entirety. Accordingly, in certain embodiments of the present invention the liposomal carrier may target cells and/or preferentially distribute to one or more target cells and tissues (e.g., target cells and tissues of the liver) following their delivery to a subject. Following transfection of the target cells (e.g., local endothelial cells of the lung), the nuclease resistant mRNA polynucleotides loaded in the carrier are translated and a functional expression product expressed, excreted and systemically distributed.

In some embodiments, the compositions of the present invention comprise one or more additional molecules (e.g., proteins, peptides, aptamers or oliogonucleotides) which facilitate the transfer of the polynucleotides (e.g., mRNA, miRNA, snRNA and snoRNA) from the carrier into an intracellular compartment of the target cell. In certain embodiments, the additional molecule facilitates the delivery of the polynucleotides into, for example, the cytosol, the lysosome, the mitochondrion, the nucleus, the nucleolae or the proteasome of a target cell. Such agents may facilitate the transport of the translated protein of interest from the cytoplasm to its normal intercellular location (e.g., in the mitochondrion) to treat deficiencies in that organelle. In some embodiments, the agent is selected from the group consisting of a protein, a peptide, an aptamer, and an oligonucleotide. Similarly, in certain embodiments where such agents may exploit the presence of one or more endogenous receptors or mechanisms to actively transport such expressed proteins or enzymes into the plasma. In other embodiments, the compositions described herein may comprise one or more excipients that facilitate the distribution of such compositions into the plasma, where such compositions may further distribute to one or more additional target organs, tissues or cells.

In certain embodiments, the compositions of the present invention facilitate a subject's endogenous production of one or more functional proteins and/or enzymes. The endogenous production or translation of exogenous nuclease resistant mRNA polynucleotides by a subject to produce one or more expression products (e.g., proteins and/or enzymes) may, in certain instances demonstrate less immunogenicity relative to their recombinantly-prepared counterparts that often lack native post-translational modifications (e.g., glycosylation). Similarly, the endogenously produced or translated proteins and/or enzymes may demonstrate more biological activity relative to their recombinantly-prepared counterparts. In a preferred embodiment of the present invention, the carriers comprise nuclease resistant mRNA polynucleotides which encode a deficient expression product (e.g., a protein or enzyme). The administration of an mRNA polynucleotide (e.g., a nuclease resistant mRNA polynucleotide) encoding a deficient protein or enzyme avoids the need to deliver the polynucleotides to specific organelles within a target cell (e.g., mitochondria). Rather, upon transfection of a target cell and delivery of the polynucleotides to the cytoplasm of the target cell, the mRNA polynucleotide contents of a carrier may be translated and a functional protein or enzyme expressed.

The present invention also contemplates the discriminatory targeting of target cells and tissues by both passive and active targeting means. The phenomenon of passive targeting exploits the natural distributions patterns of a carrier in vivo without relying upon the use of additional excipients or means to enhance recognition of the carrier by target cells. For example, carriers which are subject to phagocytosis by the cells of the reticulo-endothelial system are likely to accumulate in the liver or spleen, and accordingly may provide means to passively direct the delivery of the compositions to such target cells.

The present invention also contemplates active targeting, which involves the use of additional excipients, referred to herein as "targeting ligands" that may be bound (either covalently or non-covalently) to the carrier to encourage localization of such carrier at certain target cells or target tissues. For example, targeting may be mediated by the inclusion of one or more endogenous targeting ligands (e.g., apolipoprotein E) in or on the carrier to encourage distribution to the target cells or tissues. Recognition of the targeting ligand by the target tissues actively facilitates tissue distribution and cellular uptake of the carrier and/or its polynucleotide contents in the target cells and tissues (e.g., the inclusion of an apolipoprotein-E targeting ligand in or on the carrier may encourage recognition and binding of the carrier to endogenous low density lipoprotein receptors expressed by hepatocytes). As provided herein, the composition can comprise a ligand capable of enhancing affinity of the composition to the target cell. Targeting ligands may be linked to the outer bilayer of the lipid particle during formulation or post-formulation. These methods are well known in the art. In addition, some lipid particle formulations may employ fusogenic polymers such as PEAA, hemagluttinin, other lipopeptides (see U.S. patent application Ser. Nos. 08/835,281, and 60/083,294, which are incorporated herein by reference) and other features useful for in vivo and/or intracellular delivery. In other some embodiments, the compositions of the present invention demonstrate improved transfection efficacies, and/or demonstrate enhanced selectivity towards target cells or tissues of interest. Contemplated therefore are compositions which comprise one or more ligands (e.g., peptides, aptamers, oligonucleotides, a vitamin or other molecules) that are capable of enhancing the affinity of the compositions and their polynucleotide contents for the target cells or tissues. Suitable ligands may optionally be bound or linked to the surface of the carrier. In some embodiments, the targeting ligand may span the surface of a carrier or be encapsulated within the carrier. Suitable ligands and are selected based upon their physical, chemical or biological properties (e.g., selective affinity and/or recognition of target cell surface markers or features.) Cell-specific target sites and their corresponding targeting ligand can vary widely. Suitable targeting ligands are selected such that the unique characteristics of a target cell are exploited, thus allowing the composition to discriminate between target and non-target cells. For example, compositions of the present invention may bear surface markers (e.g., apolipoprotein-B or apolipoprotein-E) that selectively enhance recognition of, or affinity to hepatocytes (e.g., by receptor-mediated recognition of and binding to such surface markers). Additionally, the use of galactose as a targeting ligand would be expected to direct the compositions of the present invention to parenchymal hepatocytes, or alternatively the use of mannose containing sugar residues as a targeting ligand would be expected to direct the compositions of the present invention to liver endothelial cells (e.g., mannose containing sugar residues that may bind preferentially to the asialoglycoprotein receptor present in hepatocytes). (See Hillery A M, et al. "Drug Delivery and Targeting: For Pharmacists and Pharmaceutical Scientists" (2002) Taylor & Francis, Inc.) The presentation of such targeting ligands that have been conjugated to moieties present in the carrier (e.g., a lipid nanopartide) therefore facilitate recognition and uptake of the compositions of the present, invention in target cells and tissues. Examples of suitable targeting ligands include one or more peptides, proteins, aptamers, vitamins and oligonucleotides.

In certain embodiments, the carriers disclosed herein may also comprise one or more opsonization-inhibiting moieties, which are typically large hydrophilic polymers that are chemically or physically bound to a carrier or vehicle such as a lipid nanoparticle (e.g., by the intercalation of a lipid-soluble anchor into the membrane itself, or by binding directly to active groups of membrane lipids). These opsonization-inhibiting hydrophilic polymers form a protective surface layer which significantly decreases the uptake of the pharmaceutical carrier or vehicle (e.g., liposomes) by the macrophage-monocyte system and reticulo-endothelial system, as described for example, in U.S. Pat. No. 4,920,016, the entire disclosure of which is herein incorporated by reference. Carriers modified with opsonization-inhibition moieties thus remain in the circulation much longer than their unmodified counterparts.

As used herein, the term "subject" refers to any animal (e.g., a mammal), including, but not limited to, humans, non-human primates, rodents, and the like, to which the compositions and methods of the present invention are administered. Typically, the terms "subject" and "patient" are used interchangeably herein in reference to a human subject.

As used herein, the term "target cell" refers to a cell to which a composition, nuclease resistant polynucleotide and/or stabilizing oligonucleotide of the invention are to be directed or targeted. In some embodiments, the target cells are deficient in a protein or enzyme of interest. In some embodiments, cells are targeted based on their ability to secrete one or more expression products extracellularly. The compositions and methods of the present invention may be prepared to preferentially target a variety of target cells, which include, but are not limited to, pulmonary epithelial cells (e.g., Type I and II pneumocytes), alveolar cells, hepatocytes, hematopoietic cells, epithelial cells, endothelial cells, lung cells, bone cells, stem cells, mesenchymal cells, neural cells (e.g., meninges, astrocytes, motor neurons, cells of the dorsal root ganglia and anterior horn motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells. In certain embodiments, the target cells comprise Type I pneumocytes, Type II pneumocytes, alveolar cells and combinations thereof. Following transfection of one or more target cells by the compositions and nuclease resistant polynucleotides of the present invention, expression of the polypeptide, protein or enzyme encoded by such polynucleotide may be preferably stimulated and the capability of such target cells to express the protein of interest enhanced. For example, transfection of a target cell with a stabilized or duplexed mRNA polynucleotide encoding the OTC enzyme may facilitate the enhanced expression of the corresponding expression product (OTC) following translation of the mRNA polynucleotide.

Also contemplated by the present inventions are methods of treating a subject having or otherwise affected by a protein or enzyme deficiency. Such methods generally comprise administering to the subject (e.g., parenterally) a composition comprising a nuclease resistant mRNA polynucleotide and a suitable carrier, wherein the mRNA encodes an enzyme or protein in which the subject is deficient.

The compositions and methods of the present invention may be suitable for the treatment of diseases or disorders relating to the deficiency of proteins and/or enzymes. In certain embodiments, the stabilized or nuclease resistant polynucleotides of the present invention encode functional proteins or enzymes that are excreted or secreted by the target cell into the surrounding extracellular fluid (e.g., mRNA encoding hormones and neurotransmitters). Alternatively, in other embodiments, the polynucleotides (e.g., mRNA encoding urea cycle metabolic disorders) of the present invention encode functional proteins or enzymes that remain in the cytosol of the target cell. Other disorders for which the present invention are useful include disorders such as Duchenne muscular dystrophy, blood clotting disorders, such as e.g., hemophelia, SMN1-related spinal muscular atrophy (SMA); amyotrophic lateral sclerosis (ALS); GALT-related galactosemia; Cystic Fibrosis (CF); SLC3A1-related disorders including cystinuria; COL4A5-related disorders including Alport syndrome; galactocerebrosidase deficiencies; X-linked adrenoleukodystrophy and adrenomyeloneuropathy; Friedreich's ataxia; Pelizaeus-Merzbacher disease; TSC1 and TSC2-related tuberous sclerosis; Sanfilippo B syndrome (MPS IIIB); CTNS-related cystinosis; the FMRI-related disorders which include Fragile X syndrome. Fragile X-Associated Tremor/Ataxia Syndrome and Fragile X Premature Ovarian Failure Syndrome; Prader-Willi syndrome; hereditary hemorrhagic telangiectasia (AT); Niemann-Pick disease Type C1; the neuronal ceroid lipofuscinoses-related diseases including Juvenile Neuronal Ceroid Lipofuscinosis (JNCL), Juvenile Batten disease, Santavuori-Haltia disease, Jansky-Bielschowsky disease, and PTT-1 and TPP1 deficiencies; E1F2B1, E1F2B2, E1F2B3, E1F2B4 and EIF2B5-related childhood ataxia with central nervous system hypomyelination/vanishing white matter; CACNA1A and CACNB4-related Episodic Ataxia Type 2; the MECP2-related disorders including Classic Rett Syndrome, MECP2-related Severe Neonatal Encephalopathy and PPM-X Syndrome; CDKL5-related Atypical Rett Syndrome; Kennedy's disease (SBMA); Notch-3 related cerebral autosomal dominant arteriopathy with subcortical infarcts and leukoencephalopathy (CADAS1L); SCN1A and SCN1 B-related seizure disorders; the Polymerase G-related disorders which include Alpers-Huttenlocher syndrome, POLG-related sensory ataxic neuropathy, dysarthria, and ophthalmoparesis, and autosomal dominant and recessive progressive external ophthalmoplegia with mitochondrial DNA deletions; X-Linked adrenal hypoplasia: X-linked agammaglobulinemia; and Wilson's disease. In certain embodiments, the polynucleotides, and in particular mRNA, of the present invention may encode functional proteins or enzymes. For example, the compositions of the present invention may include mRNA encoding erythropoietin, al-antitrypsin, carboxypeptidase N, human growth hormone, Factor VII, Factor III, Factor IX, or cystic fibrosis transmembrane conductance regulator (CFTR).

Alternatively the nuclease resistant polynucleotides disclosed herein may encode full length antibodies or smaller antibodies (e.g., both heavy and light chains) to confer immunity to a subject. While certain embodiments of the present invention relate to methods and compositions useful for conferring immunity to a subject (e.g., via the translation of mRNA polynucleotides encoding functional antibodies), the inventions disclosed herein and contemplated hereby are broadly applicable. In an alternative embodiment the compositions of the present invention encode antibodies that may be used to transiently or chronically affect a functional response in subjects. For example, the nuclease resistant mRNA polynucleotides of the present invention may encode a functional monoclonal or polyclonal antibody, which upon translation (and as applicable, systemic excretion from the target cells) may be useful for targeting and/or inactivating a biological target (e.g., a stimulatory cytokine such as tumor necrosis factor). Similarly, the nuclease resistant mRNA polynucleotides of the present invention may encode, for example, functional anti-nephritic factor antibodies useful for the treatment of membranoproliferative glomerulonephritis type II or acute hemolytic uremic syndrome, or alternatively may encode anti-vascular endothelial growth factor (VEGF) antibodies useful for the treatment of VEGF-mediated diseases, such as cancer.

The compositions of the present invention may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement, by those of skill in the art. For example, a suitable amount and dosing regimen is one that causes at least, transient expression of the stable or nuclease resistant polynucleotide in the target cell.

Suitable routes of administration of the compositions disclosed herein may include, for example, pulmonary, oral, rectal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

In certain embodiments, the compositions of the present invention are formulated such that they are suitable for extended-release of tire stabilized or nuclease resistant polynucleotides contained therein. Such, extended-release compositions may be conveniently administered to a subject at extended dosing intervals. For example, in certain embodiments, the compositions of the present invention are administered to a subject twice day, daily or every other day. In a preferred embodiment, the compositions of the present invention are administered to a subject twice a week, once a week, every ten days, every two weeks, every three weeks, or more preferably every four weeks, once a month, every six weeks, every eight weeks, every other month, every three months, every four months, every six months, every eight months, every nine months or annually. Also contemplated are compositions and liposomal carriers which are formulated for depot administration (e.g., intramuscularly, subcutaneously, intravitreally) to either deliver or release a polynucleotides (e.g., mRNA) over extended periods of time. Preferably, the extended-release means employed are combined with modifications made to the polynucleotide to enhance stability.

Also contemplated herein are lyophilized pharmaceutical compositions comprising one or more of the compounds disclosed herein and related methods for the use of such lyophilized compositions as disclosed for example, in U.S. Provisional Application No. 61/494,882 filed Jun. 8, 2011, the teachings of which are incorporated herein by reference in their entirety. For example, the lyophilized pharmaceutical compositions according to the invention may be reconstituted prior to their administration to a subject (e.g., reconstituted using purified water or normal saline and inhaled by a subject using a device such as a nebulizer). In certain embodiments, the lyophilized compositions can be reconstituted in vivo, for example by lyophilizing such composition in an appropriate dosage form (e.g., an intradermal dosage form such as a disk, rod or membrane) and administering such composition such that it is rehydrated overtime in vivo by the individual's bodily fluids.

While certain compounds, compositions and methods of the present invention have been described with specificity in accordance with certain embodiments, the following examples serve only to illustrate the compounds of the invention and are not intended to limit the same. Each of the publications, reference materials, accession numbers and the like referenced herein to describe the background of the invention and to provide additional detail regarding its practice are hereby incorporated by reference in their entirety.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXAMPLES

Example 1

The present example illustrates the ability of stabilizing oligonucleotides of the present invention to enhance the production of protein when co-administered with non-denatured in vitro transcribed mRNA. Without wishing to be bound by any theory, it is contemplated that the stabilizing oligonucleotides modulate the nuclease resistance and increases the translational efficiency of mRNA polynucleotide transcripts.

To perform the instant studies, a 15-mer (2'O-Me-uracil) stabilizing oligonucleotide having a phosphorothioate backbone (MW=4965.8 g/mol) was prepared and which was designed to be complementary to the poly-A tail of an mRNA polynucleotide (MW=299605 g/mol) encoding human erythropoietin (EPO) protein. The EPO mRNA transcript was contacted with the stabilizing oligonucleotide at 0.001:1, 0.01:1, 0.1:1, 0.25:1, 1:1, 10:1 and 100:1 parts stabilizing oligonucleotide to mRNA polynucleotide. The resultant stabilized mRNA transcripts (designated "0.001", "0.01", "0.1", "0.25", "1", "10" or "100") or the untreated, non-denatured EPO polynucleotide control transcript (designated "Unhybridized") were then transiently transfected into 293T cells. The cumulative amounts of EPO protein produced and expressed by the transfected 293T cells were then measured at 6, 24 and 72 hour intervals.

Figure 2:
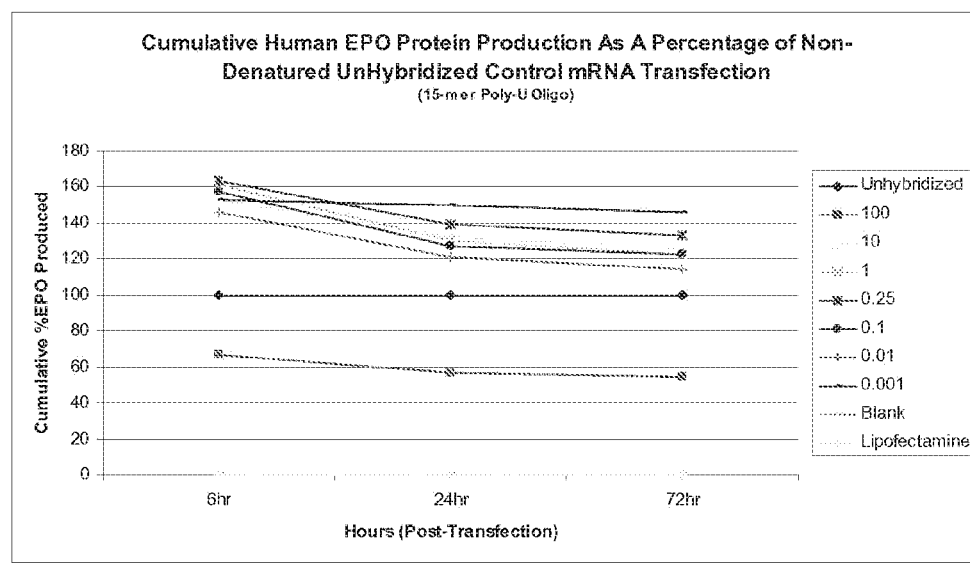
FIG. 2 depicts the cumulative amount of erythropoietin protein (EPO) produced in vitro over a seventy-two hour period by 293T cells transfected with various nuclease resistant polynucleotides of the present invention. Non-denatured human EPO mRNA was hybridized with a 15-mer of fully phosphorothioated 2-OMe-uridine oligonucleotides in the ratios listed (oligo:mRNA). The depicted plot is represented as a percentage of the protein produced from the unhybridized native EPO mRNA.

As illustrated in FIG. 2 and Table 1, with the exception of the stabilized EPO mRNA transcript prepared using 100:1 parts stabilizing oligonucleotide to mRNA (designated "100"), the cumulative amount of EPO protein produced and secreted by the 293T cells that were transfected with the stabilized mRNA transcripts exceeded the cumulative amount of EPO protein produced by the cells transfected with the Unhybridized mRNA transcript. In particular, the stabilized EPO mRNA transcripts designated 0.001, 0.01, 0.1, 0.25, 1 and 10 each resulted in the production of more EPO protein relative to the Unhybridized EPO control and, in certain instances exceeded the amount of EPO protein produced by the control by over 160% at the 6 hour time point.

TABLE 1

|  | Cumulative Amount EPO Produced (%) | | |
| --- | --- | --- | --- |
|  | 6 hr | 24 hr | 72 hr |
| Unhybridized | 100 | 100 | 100 |
| 100 | 66.5257 | 57.06707 | 54.53366 |
| 10 | 153.1145 | 132.3777 | 125.6762 |
| 1 | 161.0291 | 130.1917 | 122.7891 |
| 0.25 | 163.0904 | 139.4457 | 133.4223 |
| 0.1 | 157.012. | 127.0178 | 122.2577 |
| 0.01 | 146.0027 | 121.2735 | 114.2745 |
| 0.001 | 152.7725 | 150.0675 | 145.8507 |
| Blank | 0 | 0 | 0 |
| Lipofectamine | 0 | 0 | 0 |

Example 2

The present example further illustrates the ability of the stabilizing oligonucleotides of the present invention to enhance the protein production by first hybridizing to a denatured single-stranded mRNA to form a stabilized mRNA before administering into cells for protein production As described in Example 1 above, a 15-mer (2'O-Me-uracil) stabilizing oligonucleotide having a phosphorothioate backbone was prepared and which was designed to be complementary to the poly-A tail of an mRNA polynucleotide encoding human erythropoietin (EPO) protein. The EPO mRNA transcript was first denatured at 65° C. for 10 minutes, and then contacted with the stabilizing oligonucleotide at 0.001:1, 0.01:1, 0.1:1, 0.25:1, 1:1, 10:1 and 100:1 parts stabilizing oligonucleotide to mRNA polynucleotide. The resultant stabilized mRNA transcripts (designated "0.001", "0.01", "0.1", "0.25", "1", "10" or "100") or the untreated, denatured EPO polynucleotide control transcript (designated "Unhybridized") were then transiently transfected into 293T cells. The cumulative amounts of EPO protein produced and expressed by the transfected 293T cells were then measured at 6, 24 and 72 hour intervals.

Figure 3:
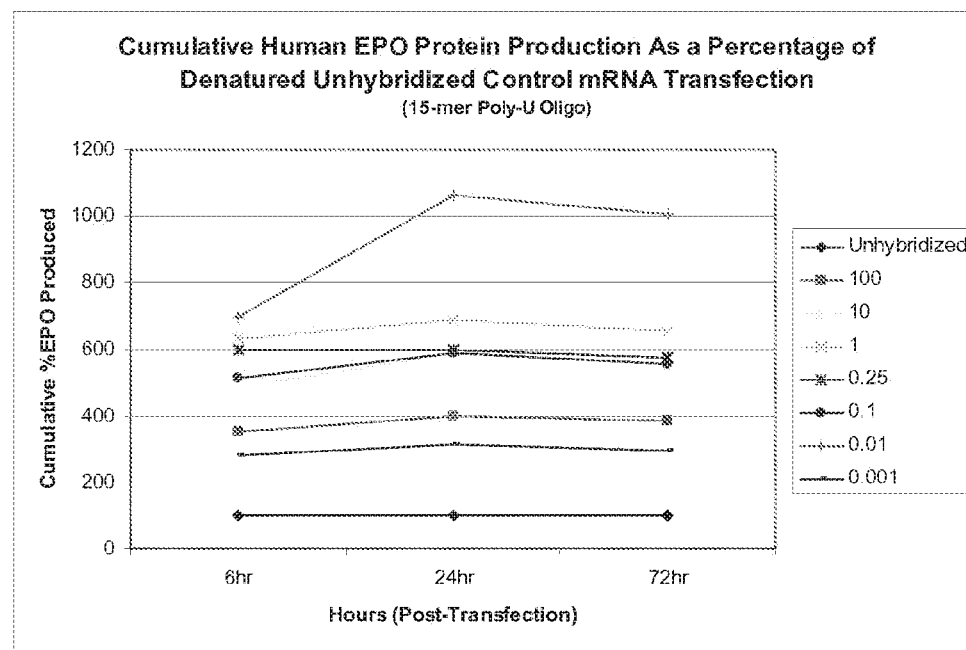
FIG. 3 illustrates the quantification of cumulative human erythropoietin (EPO) protein produced in vitro over a seventy-two hour period by 2.93 T cells transfected with various stabilized mRNA transcripts of the present invention. Denatured human EPO mRNA was hybridized with a 15-mer of fully phosphorothioated 2-OMe-uridine oligonucleotides in the ratios listed (oligo:mRNA). The depicted plot is represented as a percentage of the protein produced from the unhybridized denatured EPO mRNA.

As illustrated in FIG. 3 and in Table 2 below, relative to the denatured Unhybridized control mRNA, the percentage of the cumulative amount of EPO protein produced and secreted by the 293T cells transfected with the stabilized mRNA polynucleotide consistently exceeded the percentage of the cumulative amount of EPO protein produced and secreted by the Unhybridized mRNA polynucleotide at each time point evaluated.

TABLE 2

|  | Cumulative Amount EPO Produced (%) | | |
| --- | --- | --- | --- |
|  | 6 hr | 24 hr | 72 hr |
| Unhybridized | 100 | 100 | 100 |
| 100 | 351.0201 | 398.7672 | 383.0498 |
| 10 | 482.7039 | 586.7506 | 555.2077 |

TABLE 2-continued

|  | Cumulative Amount EPO Produced (%) | | |
| --- | --- | --- | --- |
|  | 6 hr | 24 hr | 72 hr |
| 1 | 633.1448 | 685.7419 | 656.1553 |
| 0.25 | 597.5827 | 598.553 1 | 572,3968 |
| 0.1 | 512.6893 | 587.4839 | 554.1234 |
| 0.01 | 697.0948 | 1062.025 | 1003.248 |
| 0.001 | 281.3981 | 314.8646 | 296.2899 |

For example, the stabilized EPO transcript designated 0.01 demonstrated an approximately 700% increase in the cumulative amount of EPO protein produced relative to the Unhybridized control transcript at the 6 hour time point and in excess of 1,000% at both the 24 hour and 72 hour time points. Each of the stabilized mRNA transcripts evaluated were characterized by an increase in the cumulative amount of EPO protein produced relative to the Unhybridized control.

Example 3

The instant study was performed to investigate optimal length of the stabilizing oligonucleotides of the present invention.

A 30-mer (2'O-Me-uracil) stabilizing oligonucleotide having a phosphorothioate backbone was prepared and which was designed to be complementary to the poly-A tail of an mRNA polynucleotide encoding human erythropoietin (EPO) protein. A non-denatured EPO mRNA transcript was contacted with the stabilizing oligonucleotide at 0.001:1, 0.01:1, 0.1:1, 0.25:1, 0.5:1, 1:1 and 2:1 parts stabilizing oligonucleotide to mRNA polynucleotide. The resultant stabilized mRNA transcripts (designated "0.001", "0.01", "0.1", "0.25", "0.5", "1" or "2") or the untreated, non-denatured EPO polynucleotide control transcript (designated "Unhybridized") were then transiently transfected into 293T cells. The cumulative amounts of EPO protein produced and expressed by the transfected 293T cells were then measured at 24, 48, 72 and 96 hour intervals.

Figure 4:
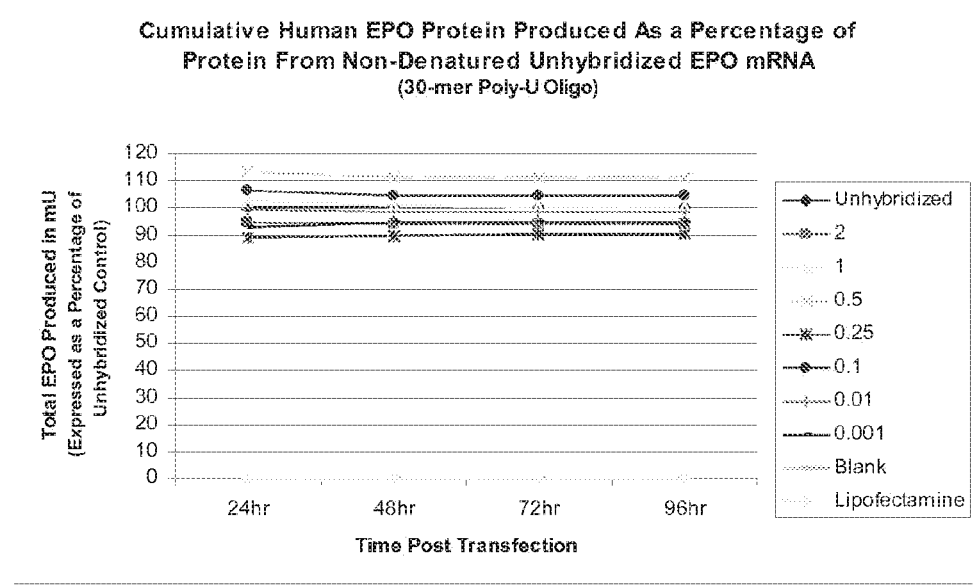
FIG. 4 depicts the cumulative amount of erythropoietin (EPO) protein produced in vitro by 293T cells transfected with various nuclease resistant polynucleotides of the present invention at different time points over a ninety-six hour period. Human EPO mRNA was hybridized with a 30-mer of folly phosphorothioated 2-OMe-uridine oligonucleotides in the ratios listed (oligo:mRNA). The depicted plot is represented as a percentage of the protein produced from the respective unhybridized native EPO mRNA.

As illustrated in FIG. 4, those stabilized mRNA polynucleotides prepared using 0.1:1 and 0.5:1 parts stabilizing oligonucleotide to mRNA polynucleotide (designated "0.1" and "0.5"), cumulatively produced and secreted more EPO protein relative to the Unhybridized control polynucleotide. Interestingly, an approximately 10% reduction of the cumulative amount of EPO protein produced relative to the Unhybridized control polynucleotide was observed with several of the stabilized mRNA transcripts evaluated (e.g., the stabilized mRNA transcript designated "0.25"). In general, the cumulative amount of EPO protein produced using the 30-mer stabilizing oligonucleotide appeared to be less than that observed using shorter stabilizing oligonucleotides (e.g., a 15-mer stabilizing oligonucleotide). Without wishing to be bound by any particular theory, such reduction may be due in part to the greater degree of hybridization observed with longer stabilizing oligonucleotides, or the interference with the ability of the mRNA transcript to form stable secondary structures.

The foregoing examples demonstrate that the stabilized mRNA transcripts that were prepared by exposure of the mRNA polynucleotides to stabilizing oligonucleotides produced more protein and demonstrated improved translational efficiencies relative to those stabilized mRNA transcripts that were prepared by exposure to the highest ratios of stabilizing oligonucleotide to mRNA polynucleotide. In particular, those stabilized mRNA polynucleotides prepared by exposure to about 0.001:1, 0.01:1, 0.1: 1, 0.25:1, 0.5:1, 1:1, 2:1, 10:1 parts stabilizing oligonucleotide to mRNA polynucleotide appeared result in more protein being produced and secreted by the transfected cells relative to the native or un-stabilized mRNA transcript.

Without wishing to be bound by any particular theories, it is believed that a greater degree of hybridization of the stabilizing oligonucleotide to the mRNA transcript may interfere (e.g., sterically interfere) with the ability of the mRNA transcript to form secondary structures (e.g., hairpin loops) that may serve to further protect and stabilize the mRNA transcript from nuclease degradation. Similarly, a greater degree of hybridization of the mRNA transcript may negatively impacting endogenous cellular function, for example, by interfering with the ability of cells or of organelles within such cells to translate the mRNA polynucleotide transcript. The present inventors have also observed that hybridization of the stabilizing oligonucleotides to the mRNA polynucleotide transcript at lower concentrations (in particular at 0.01:1, 0.1:1, 0.25:1, 0.5:1, 1:1, 2:1, 10:1 parts stabilizing oligonucleotide to mRNA polynucleotide) appear to have stabilized the mRNA polynucleotide from nuclease degradation, while not materially impacting or negatively interfering with the ability of such stabilized mRNA transcript to form secondary structures. The exposure of an mRNA transcript to lower concentrations or ratios of the stabilizing oligonucleotide (e.g., about 0.01:1, 0.1:1, 0.25:1, 0.5:1, 1:1, 2:1, 10:1 parts stabilizing oligonucleotide to mRNA polynucleotide) therefore appears to provide optimum, stabilization of mRNA polynucleotide transcript. Similarly, in certain embodiments, upon hybridizing to an mRNA transcript, the stabilizing oligonucleotides of shorter lengths (e.g., about 15-mer) appear to demonstrate optimal stabilization of the mRNA transcript. Accordingly, the foregoing evidences the methods of modulating the nuclease resistance of polynucleotides and the improved translational efficiencies observed when polynucleotides are stabilized with one or more stabilizing oligonucleotides.

We claim:

1. A method of modulating the nuclease resistance of a polynucleotide having a coding region and a non-coding region, the method comprising a step of contacting the polynucleotide with a stabilizing oligonucleotide, wherein the stabilizing oligonucleotide and polynucleotide are contacted at a ratio of between 0.01 and 1, thereby modulating the nuclease resistance of the polynucleotide, wherein the stabilizing oligonucleotide is about 5-20 nucleotides in length and is complementary to the non-coding region of the polynucleotide and comprises at least one modified nucleobase.

2. The method of claim 1, wherein the polynucleotide is mRNA.

3. The method of claim 1, wherein the non-coding region of the polynucleotide is selected from the group of regions consisting of a 3' untranslated region (UTR), a 5' untranslated region (UTR), a poly-A tail, a terminal cap, and combination thereof.

4. The method of claim 1, wherein the non-coding region of the polynucleotide comprises a poly(A) tail.

5. The method of claim 4, wherein the stabilizing oligonucleotide comprises a poly-U sequence.

6. The method of claim 1, wherein the stabilizing oligonucleotide is about 3 to about 20 nucleotides in length.

7. The method of claim 2, wherein the mRNA encodes a protein selected from the group consisting of erythropoietin, human growth hormone, cystic fibrosis transmembrane conductance regulator (CFTR), alpha-galactosidase A, alpha-L-iduronidase, iduronate-2-sulfatase, N-acetylglucosamine-1-phosphate transferase, N-acetylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, hyaluronidase, galactocerebrosidase, ornithine transcarbamylase (OTC), carbamoyl-phosphate synthetase 1 (CPS1), argininosuccinate synthetase (ASS1), argininosuccinate lyase (ASL), and arginase 1 (ARG1).

8. The method of claim 1, wherein the stabilizing oligonucleotide and polynucleotide are contacted at a ratio ranging between about 0.001:1 and about 0.5:1.

9. A method of increasing translation of polypeptide from an mRNA transcript having a coding region and a non-coding region, the method comprising a step of hybridizing a stabilizing oligonucleotide to a portion of the non-coding region of the mRNA transcript, wherein the stabilizing oligonucleotide and mRNA transcript are hybridized at a ratio of between 0.01-1, thereby increasing amount of the polypeptide translated from the mRNA transcript; and wherein the stabilizing oligonucleotide is about 5-20 nucleotides in length and comprises at least one modified nucleobase.

10. The method of claim 9, wherein the non-coding region of the mRNA transcript is selected from the group of regions consisting of a 3' untranslated region (UTR), a 5' untranslated region (UTR), a poly-A tail and a terminal cap.

11. A method of increasing translation of an exogenous mRNA transcript having a coding region and a non-coding region, the method comprising a step of co-administering the exogenous mRNA transcript with a stabilizing oligonucleotide into a cell; wherein the stabilizing oligonucleotide and the exogenous mRNA transcript are co-administered at a ratio of between 0.01-1; wherein the stabilizing oligonucleotide is about 5-20 nucleotides and is complementary to the non-coding region of the mRNA transcript; wherein the co-administering results in increased translation of the exogenous mRNA transcript; and wherein the stabilizing oligonucleotide comprises at least one modified nucleobase.

* * * * *

```
                           SEQUENCE LISTING

<160> NUMBER OF SEQ ID NOS: 5

<210> SEQ ID NO 1
<211> LENGTH: 140
<212> TYPE: RNA
<213> ORGANISM: Artificial Sequence
<220> FEATURE:
<223> OTHER INFORMATION: CMV Polynucleotide Sequence

<400> SEQUENCE: 1
ggacagaucg ccuggagacg ccauccacgc uguuuugacc uccauagaag acaccgggac      60
cgauccagcc uccgcggccg ggaacggugc auuggaacgc ggauuccccg ugccaagagu     120
gacucaccgu ccuugacacg                                                 140

<210> SEQ ID NO 2
<211> LENGTH: 157
<212> TYPE: RNA
<213> ORGANISM: Artificial Sequence
<220> FEATURE:
<223> OTHER INFORMATION: CMV Polynucleotide Sequence

<400> SEQUENCE: 2
uaauacgacu cacuauagga cagaucgccu ggagacgcca uccacgcugu uuugaccucc      60
auagaagaca ccgggaccga uccagccucc gcggccggga acggugcauu ggaacgcgga     120
uuccccgugc caagagugac ucaccguccu ugacacg                              157

<210> SEQ ID NO 3
<211> LENGTH: 100
<212> TYPE: RNA
<213> ORGANISM: Homo sapiens

<400> SEQUENCE: 3
cggguggcau cccugugacc ccuccccagu gccucuccug gcccuggaag uugccacucc      60
agugcccacc agccuugucc uaauaaaauu aaguugcauc                           100

<210> SEQ ID NO 4
<211> LENGTH: 35
<212> TYPE: RNA
<213> ORGANISM: Artificial Sequence
<220> FEATURE:
<223> OTHER INFORMATION: chemically synthesized oligonucleotide
```

```
<400> SEQUENCE: 4
auggcacauc cuguaaaaaa aaaaaaaaaa aaaaa                          35

<210> SEQ ID NO 5
<211> LENGTH: 17
<212> TYPE: RNA
<213> ORGANISM: Artificial Sequence
<220> FEATURE:
<223> OTHER INFORMATION: chemically synthesized oligonucleotide

<400> SEQUENCE: 5
uuuuuuuuuu uuuuuac                                              17
```